(12) United States Patent
Riggins et al.

(10) Patent No.: US 7,927,826 B2
(45) Date of Patent: *Apr. 19, 2011

(54) METHOD FOR DISTINGUISHING FOLLICULAR THYROID ADENOMA (FTA) FROM FOLLICULAR THYROID CARCINOMA (FTC)

(75) Inventors: Gregory J. Riggins, Baltimore, MD (US); Janete Cerruti, Sao Paulo (BR)

(73) Assignee: Duke University, Durham, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/648,771

(22) Filed: Dec. 29, 2009

(65) Prior Publication Data

US 2010/0184055 A1 Jul. 22, 2010

Related U.S. Application Data

(62) Division of application No. 11/954,661, filed on Dec. 12, 2007, now Pat. No. 7,645,590, which is a division of application No. 11/100,640, filed on Apr. 7, 2005, now Pat. No. 7,319,011.

(60) Provisional application No. 60/560,243, filed on Apr. 8, 2004.

(51) Int. Cl.
*G01N 33/574* (2006.01)
*G01N 33/53* (2006.01)
*C12Q 1/68* (2006.01)

(52) U.S. Cl. ............................. 435/7.23; 435/6; 435/7.1

(58) Field of Classification Search .................... None
See application file for complete search history.

(56) References Cited

U.S. PATENT DOCUMENTS

| | | | |
|---|---|---|---|
| 6,066,449 | A | 5/2000 | Ditkoff et al. |
| 6,436,642 | B1 | 8/2002 | Gould-Rothberg et al. |
| 2002/0102531 | A1 | 8/2002 | Horrigan |

OTHER PUBLICATIONS

Barden et al., Clinical Cancer Research 9:1792-1800, 2003.
Marques et al., The Journal of Clinical Endocrinology & Metabolism 87:3947-52, 2002.
Nagasaka et al., Metabolism 36:388-391, 1987.
Gimm et al., Journal of Clinical Endocrinology & Metabolism 86:1801-1805, 2001.
Hirai et al., Pathology International 49:264-265, 2001.
Brennan et al., (journal of Autoimmunity, 1989, vol. 2 Suppl., pp. 177-186).
Zimmer (Cell Motility and the Cytoskeleton, 1991, vol. 20, pp. 325-337).
Hell et al., (Laboratory Investigation, 1995, vol. 73, pp. 492-496).
Powell et al., (Pharmacogenesis, 1998, vol. 8, pp. 411-421).
Carrere et al., (Gut, 1999, vol. 44, pp. 54-551).
Vallejo et al., (Biochimie, 2000, vol. 82, pp. 1129-1133).
Guo et al., (Journal of Pharmacology and Experimental Therapeutics, 2002, vol. 3000, pp. 206-212).
Jang et al., (Clinical and Experimental Metastasis, 1997, vol. 15, pp. 469-483).
Greenbaum et al., (Genome Biology, 2003, vol. 4, Issue 9, pp. 117. 1-117.8).
NCBI Aceview for "STT3A," p. 1-2.
NCBI Aceview for "FAM129A," p. 1-2.
Cerutti et al., Clinical Cancer Research, 2006, 12:3311-3318.
Tockman et al., Cancer Research, 1992, 52:2711s-2718s.

*Primary Examiner* — Laura B Goddard
(74) *Attorney, Agent, or Firm* — Banner & Witcoff, Ltd.

(57) ABSTRACT

Follicular thyroid adenoma (FTA) is distinguished from follicular thyroid carcinoma (FTC) by comparing amount of an expression product of at least one gene selected from the group consisting of DDIT3, ARG2, ITM1, C1orf24, TARSH, and ACO1 in a test follicular thyroid specimen to a normal control thyroid specimen. The test follicular thyroid specimen is identified as FTA if the amount of expression product of TARSH is equal to or greater in the test follicular thyroid specimen than in the normal control thyroid specimen. The test follicular thyroid specimen is identified as FTC if the amount of expression product of DDIT3, ARG2, ITM1, C1orf24, or ACO1 is greater in the test follicular thyroid specimen than in the normal control thyroid specimen.

36 Claims, 3 Drawing Sheets

US 7,927,826 B2

METHOD FOR DISTINGUISHING FOLLICULAR THYROID ADENOMA (FTA) FROM FOLLICULAR THYROID CARCINOMA (FTC)

The U.S. Government retains certain rights to this invention due to funding by the National Institutes of Health contract number NIH 98X-S146A.

FIELD OF THE INVENTION

The invention relates to the field of distinguishing thyroid diseases, and more particularly to the field of distinguishing follicular thyroid adenoma from follicular thyroid carcinoma.

BACKGROUND OF THE INVENTION

The incidence of thyroid cancer is increasing, with a global estimate of one-half million new cases this year. Thyroid carcinoma is usually first suspected by a physician when a solitary nodule is palpated on physical exam. Thyroid nodules, however, can be the result of a wide spectrum of causes, and a major concern is to accurately differentiate between benign and malignant nodules.

Cytology of a fine-needle aspiration (FNA) biopsy is the most widely used and cost-effective pre-operative test for initial thyroid nodule diagnosis (1). When FNA findings are diagnostic of papillary thyroid carcinoma, the specificity for malignancy approaches 95% (2). A common problem in clinical practice, however, is evaluation and management of thyroid tumors with a follicular pattern. FNA cytology cannot differentiate between follicular thyroid adenoma (FTA) and follicular thyroid carcinoma (FTC). Since cytology cannot distinguish between FTA and FTC they are often grouped together as indeterminate or follicular-patterned thyroid lesions. Surgical biopsy is needed to confirm FTA or FTC. Invasion through the tumor capsule or the blood vessels is an indicator of FTC. To provide an accurate diagnosis, most guidelines recommend surgical removal of a nodule diagnosed as having a follicular pattern. Complete thyroid resection and subsequent radioiodine therapy is indicated for those patients who ultimately have findings indicating carcinoma. Overall, only 8%-17% of these cytologically suspicious nodules are indeed malignant on histological examination (3).

Several genes have been reported to be associated with thyroid tumors. LGALS3 expression was proposed as a potential marker for pre-operative diagnosis of thyroid carcinoma (4-6). Subsequent findings, however, showed LGALS3 expression in benign lesions such as multinodular goiter and FTA (7,8). Recently, a chromosomal translocation t(2;3)(q13;p25) was reported in five of eight cases with FTC, but not in twenty cases with FTA (9). The authors suggested that the resulting PAX8/PPARG fusion gene could be useful in the diagnosis and treatment of thyroid cancer (9). This rearrangement, however, was found in 13%-30% of follicular adenomas (10-12). In addition, several molecular markers have been analyzed for their ability to discriminate between benign and malignant follicular tumors. The molecular markers include TPO, TP53, telomerase, and HMBE-1. Nonetheless, these candidate markers have not proved to have practical value for FNA pre-operative diagnosis of FTC (13-15). More recently cDNA array technology has been used to identify potentially important thyroid cancer-associated genes (16). Although many of the gene or gene patterns expressed in thyroid tumors have been described, the clinical problem of distinguishing FTC from FTA remains.

A large percentage of patients would, therefore, benefit greatly from improved diagnosis of FNA material. Improved diagnosis could reduce the number of surgeries, long-term health costs and post surgical complications. In particular, in many areas of the world where health care systems are overburdened, limited resources for surgery could be directed more rapidly towards those with the highest risk of having carcinoma. Accurate molecular markers based on differential gene expression between FTA and FTC would be one means of improving the accuracy of diagnoses made from FNA.

BRIEF SUMMARY OF THE INVENTION

In one embodiment of the invention a method for distinguishing follicular thyroid adenoma (FTA) from follicular thyroid carcinoma (FTC) is provided. Amount of an expression product of at least one gene selected from the group consisting of DDIT3, ARG2, ITM1, C1orf24, TARSH, and ACO1 in a test follicular thyroid specimen is compared to the amount in a normal control thyroid specimen. The expression product is selected from the group consisting of protein and RNA. The test follicular thyroid specimen is identified as FTA if the amount of expression product of TARSH is equal to or greater in the test follicular thyroid specimen than in the normal control thyroid specimen or the test follicular thyroid specimen is identified as FTC if the amount of expression product of DDIT3, ARG2, ITM1, C1orf24, or ACO1 is greater in the test follicular thyroid specimen than in the normal control thyroid specimen.

In another embodiment of the invention a method for distinguishing follicular thyroid adenoma (FTA) from follicular thyroid carcinoma (FTC) is provided. Amount of an expression product of DDIT3, ARG2, and ITM1 in a test follicular thyroid specimen is compared to the amount in a normal control thyroid specimen. The expression product is selected from the group consisting of protein and RNA. The test follicular thyroid specimen is identified as FTC if the amount of expression product of DDIT3, ARG2, or ITM1 is increased in the test follicular thyroid specimen relative to the normal control thyroid specimen. The invention thus provides the art with methods for distinguishing follicular thyroid adenoma from follicular thyroid carcinoma.

DETAILED DESCRIPTION OF THE INVENTION

Figure 1:
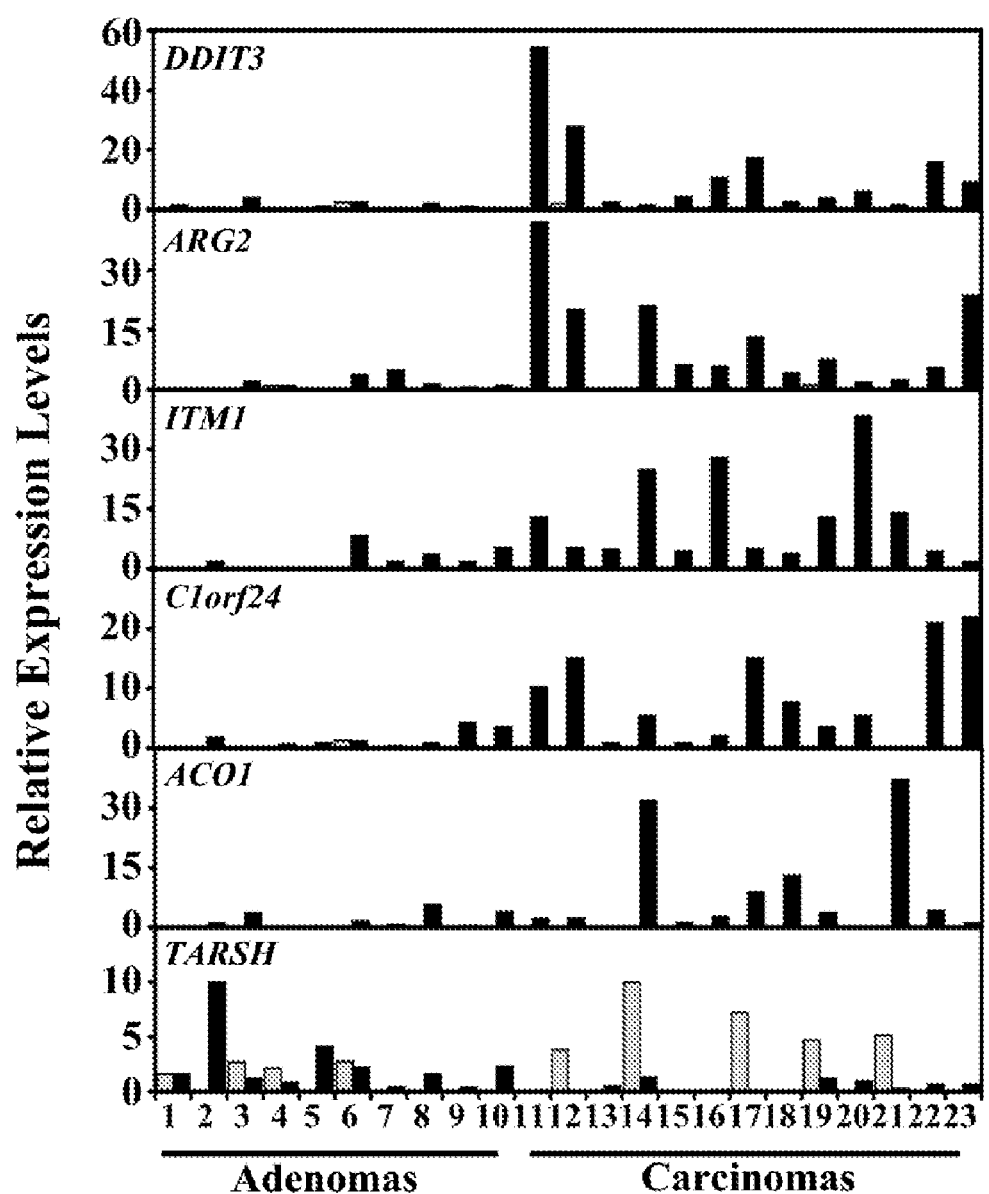
FIG. 1 shows relative expression level determined by quantitative RT-PCR in twenty three samples of FTA and FTC (black bars) and in normal thyroid tissues (gray bars). Transcript levels were normalized to the average of ribosomal protein 8 and t-complex 1, which were uniformly expressed in all three thyroid SAGE libraries. Numbers 1-10 correspond to FTA and 11-23 to FTC as described in Table 2. The statistical analysis of RT-PCR values revealed that expression of genes DDIT3, ARG2, and ITM1 were significantly different at the 0.05 level, and C1orf24 was significant at the 0.10 level. Genes ACO1 and TARSH may be involved in pathogenesis of thyroid tumor as well.

It is a discovery of the present inventors that follicular thyroid adenoma (FTA) can be distinguished from follicular thyroid carcinoma (FTC) without removing the thyroid or obtaining a surgical sample of the thyroid. In particular, the inventors have discovered that FTA can be distinguished from FTC by comparing the amount of expression product of one or more of DDIT3[1], ARG2[2], ITM1[3], C1orf24[4], ACO1[5], and TARSH[6] in a test follicular thyroid specimen to the amount of expression product in a normal control thyroid specimen.
[1]DNA-damage-inducible transcript 3D (SEQ ID NOS:1 and 2)
[2]arginase type 2D (SEQ ID NOS:3 and 4)
[3]integral membrane protein 1D (SEQ ID NOS:5 and 6)
[4]chromosome 1 open reading frame 24 (SEQ ID NOS:7 and 8)
[5]soluble aconitase 1 (SEQ ID NOS:9 and 10)
[6]NESH binding protein (SEQ ID NOS:11 and 12)

TARSH expression is indicative of FTA, while expression of DDIT3, ARG2, ITM1, C1orf24, and ACO1 is indicative of FTC. Thus, if the amount of TARSH expression product is equal to or greater in the test follicular thyroid specimen than in the normal control thyroid specimen then the test follicular thyroid specimen can be identified as FTA. If the amount of any one, or more of DDIT3, ARG2, ITM1, C1orf24, and ACO1 expression product is greater in the test follicular thyroid specimen than in the normal control thyroid specimen then the test follicular thyroid specimen can be identified as FTC.

The amount of RNA expression in a test follicular thyroid specimen or a normal control thyroid specimen can be determined by methods well known in the art for measuring RNA expression. Examples of such methods include, but are not limited to, reverse transcriptase-polymerase chain reaction (RT-PCR), microarray analysis, northern blot analysis, differential hybridization, and ribonuclease protection assay. Such methods are well known in the art and are described in Sambrook et al., MOLECULAR CLONING: A LABORATORY MANUAL, Second Edition, Cold Spring Harbor Laboratory, Cold Spring Harbor, N.Y., 1989 and Ausubel et al., CURRENT PROTOCOLS IN MOLECULAR BIOLOGY, John Wiley & Sons, New York, N.Y., 1989.

The amount of protein expression in a test follicular thyroid specimen or a normal control thyroid specimen can be determined by methods well known in the art for measuring protein expression. Such methods include, but are not limited to, immunohistochemical staining, ELISA, immunoprecipitation, western blot (immunoblot), radioimmuno assay (RIA), and fluorescence-activated cell sorting (FACS). Such methods are described in Sambrook (1989) and Ausubel (1989).

Follicular thyroid specimens are obtained from a thyroid of a human and determined histologically to have a follicular pattern, if a precise diagnosis is not achievable. The specimen can be obtained by any method known in the art for obtaining a thyroid specimen. Fine-needle aspiration (FNA) biopsy sampling is an exemplary method. The test follicular thyroid specimen can be obtained prior to removal of the thyroid. However, the specimen can also be surgically removed thyroid tissue. A normal control thyroid specimen can be, for example, an FNA biopsy from a patient with a normal thyroid. Alternatively universal reference total human RNA or normal thyroid total RNA can be used as the normal human control thyroid specimen. Similarly universal reference total human protein or normal human thyroid total protein can be used as a control.

Differential expression between test and control samples are used to make a diagnostic determination. The amount of difference observed will depend on the particular gene, or the type of expression product, or the assay method, and on sample preparation. Generally, however, a difference which is reproducible or statistically significant can be used. Differences of at least 2-fold, 5-fold, 10-fold, 20-fold, 25-fold, have been observed and can be used to make a diagnosis. Genes which are not observably expressed in one of the two forms of follicular thyroid specimen may be compared without precise quantitation, for example visually.

DDIT3, also named GADD153 (growth arrest and DNA-damage inducible 153 gene), encodes a transcription factor that is induced in response to a large spectrum of genotoxic agents such as UV light, hypoxia, nutrient deprivation, environmental toxicants, and certain DNA-damaging agents (32, 33). When induced, DDIT3 inhibits cell proliferation and promotes repair and/or apoptosis. The induction of DDIT3 leads to distinct biologic effects, such as growth stimulation, differentiation, invasiveness, and migration (34).

ITM1 encodes a highly conserved protein that contains ten to fourteen membrane-spanning domains. The protein does not have any identifiable domains with enzymatic activity and is probably not involved in direct transmembrane signaling. In addition, the transmembrane domain of ITM1 does not present any features of a transporter protein, such as an ATP binding cassette. However, Hong et al. hypothesize that ITM1 is a novel type of permease/transporter membrane protein (42). In humans, the ITM1 gene was mapped to human chromosome 11q23.3 (43,44). Interestingly, loss of heterozygosity was found in follicular adenomas at 11q (45,46).

ARG2 encodes an enzyme that catalyzes the hydrolysis of arginine to ornithine plus urea. At least two isoforms of mammalian arginase exists (ARG1 and ARG2). The two isoforms differ in their tissue distribution, subcellular localization, immunologic crossreactivity, and physiologic function (38). The type II isoform is located in the mitochondria and is expressed in extra-hepatic tissues, especially in the kidney (39). The physiologic role of this isoform is poorly understood, but it may play a role in nitric oxide and polyamine metabolism (40). Since polyamines are vital for cell proliferation, it is possible that the increased level of ornithine, due to the elevated arginase activity, may be linked to carcinogenesis development (41).

C1orf24 was described as a candidate marker for renal tumor, especially in early-stage renal carcinogenesis. The pattern of gene expression showed that C1orf24 is expressed in normal muscle, pancreas, colon, and prostate. The gene is very conserved in humans and rats, but the protein function is still unknown. A similarity with the DNAJ-1 motif, part of a chaperone system, has been described (47).

TARSH encodes a protein containing an Src-homology 3 (SH3) biding motif, a nuclear target sequence with no catalytic domain. Its biochemical and physiologic role has not been identified. TARSH is thought to be a binding partner of NESH-SH3, a member of the E3B1/ArgBP/Avi2/NESH family (48). Members of this family are involved in membrane ruffling and lamellipodia formation, which suggests that the loss of their expression could be involved in the mechanism of cell motility and metastasis. Re-expression of NESH suppresses motility and metastasis dissemination in the U-87 MG malignant glioma cell line (49). Although the binding activity between NESH and TARSH is yet to be confirmed, the loss of TARSH expression in FTCs might be a mechanism by which the follicular cells acquire motility and promote invasion. Another fact that supports this hypothesis is that the TARSH gene was mapped at 3q12, where loss of heterozygosity was found in FTC but not in FTA (50,51). Loss of heterozygosity in 3q was also correlated with survival in FTC (52).

Aconitase 1 (ACO1), also known as iron regulatory element binding protein 1 (IREB1), is a cytosolic protein which binds to iron-responsive elements (IREs). IREs are stem-loop structures found in the 5' untranslated region (UTR) of ferritin mRNA, and in the 3' UTR of transferrin receptor mRNA. The iron-induced binding of ACO1 to the IRE results in a repression of ferritin mRNA translation. Transferrin receptor mRNA is rapidly degraded, however, iron-induced binding of ACO1 to the IRE results in an inhibition of this rapid degradation. Thus, ACO1 plays a central role in cellular iron homeostasis.

All patents patent applications and references cited in this application are incorporated herein by reference in their entirety.

The following examples are offered by way of illustration and do not limit the invention disclosed herein.

EXAMPLES

Example 1

Identification of Diagnostic Markers by Sage Analysis to Distinguish FTA from FTC To directly address the problem of finding diagnostic markers that would distinguish FTA from FTC, gene expression was quantified in FTA tissues, FTC tissues, and normal thyroid tissues using serial analysis of gene expression (SAGE) (17). SAGE counts cDNA transcript tags in large numbers. Thus, SAGE analysis makes it possible to identify a restricted set of genes that are highly expressed in one tissue and not detectable in another. Transcript counts from FTC, FTA, and normal thyroid libraries were generated and compared.

SAGE Libraries.

One follicular thyroid adenoma, one follicular thyroid carcinoma, and one normal thyroid were chosen for SAGE (17). SAGE libraries were constructed using a microSAGE procedure (19) and were sequenced through the SAGE portion of the Cancer Genome Anatomic Project (20). Tags were extracted from automated sequence text files; and duplicate ditags, linker sequences, and repetitive tags were removed using SAGE 2000 software version 4.12. The Monte-Carlo simulation function (26) of the SAGE 2000 program was used to determine P values of differentially expressed genes. The full set of tag counts for all three libraries are available for downloading or analysis at the Cancer Genome Anatomy Project SAGE Genie Web site (21).

SAGE Analysis.

SAGE analysis of gene expression in FTA tissues, FTC tissues, and normal thyroid tissues resulted in a total of 359,478 tags. This represented 116,037 unique transcript tags. A SAGE tag sequence error rate of 6.8% (26) was used and we estimated that a total of 108,146 unique transcripts were detected. Of those, 10,048 were detected at least five times and 32,748 were detected at least two times.

Two comparisons were performed using SAGE 2000 software version 4.12: one between normal thyroid and FTA and one between FTA and FTC. Using SAGE software to perform Monte Carlo simulations (26), the expression level of 305 genes were found to be statistically significant if P value $\leq 0.0001$. Of those 305 genes, seventy-three genes were found to be expressed only in FTC or only in FTA and normal thyroid tissue. Thirty-seven of these 305 transcripts were highly expressed in FTC tissues and not expressed in FTA or normal tissues. Thirty-six of the 305 genes were highly expressed in FTA and normal tissues and not expressed in FTC tissues.

Among the seventy-three candidates genes, those with the greatest fold-induction or fold-repression in FTC were first considered. Accordingly, seventeen transcripts were selected for RT-PCR validation. Twelve transcripts were highly expressed in the FTC library and five were expressed only in FTA and normal thyroid libraries. The expression levels of these genes in FTA and FTC libraries ranged from 43- to 10-fold. Table 1 lists the seventeen genes. For comparison, the transcript levels for well-characterized genes for normal thyroid physiology are also presented.

TABLE 1

Validated FTA and FTC differentially expressed genes and thyroid specific genes

| Tag sequence | Normal[7] | Adenoma[7] | Carcinoma[7] | Transcript description[8] | GenBank Accession (SEQ ID NOS: nucleotide/ amino acid) | Gene Location | ontology[9] |
|---|---|---|---|---|---|---|---|
| Transcripts up regulated in FTC | | | | | | | |
| AACAATTGGG (SEQ ID NO: 79) | 0 | 0 | 19 | DDIT3 - DNA-damage-inducible transcript 3D[10] | NM_004083.2 (SEQ ID NOS: 1/2) | 12q13.1 | Regulation cell cycle |
| TTTCACAACA (SEQ ID NO: 80) | 2 | 0 | 21 | ARG2 - arginase, type II D[10] | NM_001172.2 (SEQ ID NOS: 3/4) | 14q24 | Urea cycle |

TABLE 1-continued

Validated FTA and FTC differentially expressed genes and thyroid specific genes

| Tag sequence | Normal[7] | Adenoma[7] | Carcinoma[7] | Transcript description[8] | GenBank Accession (SEQ ID NOS: nucleotide/ amino acid) | Location | Gene ontology[9] |
|---|---|---|---|---|---|---|---|
| TATTTACTCT (SEQ ID NO: 81) | 1 | 0 | 15 | C1orf24, Chromosome 1 open reading frame 24 | NM_052966 (SEQ ID NOS: 5/6) | 1q25 | ND |
| TTGTAAATTA (SEQ ID NO: 82) | 0 | 0 | 19 | PCSK2 -proprotein convertase subtisilin/ kexin type 2 | NM_002594 (SEQ ID NOS: 13/14) | 20p11.2 | Cell-cell signaling |
| CTGTAAATAT (SEQ ID NO: 83) | 0 | 0 | 12 | ODZ1 (odd Oz/tenascin-M *Drosophila melanogaster*) homolog 1 | NM_014253 (SEQ ID NOS: 15/16) | Xq25 | Proteolysis and Peptidolysis |
| GATAGGTCGG (SEQ ID NO: 84) | 0 | 0 | 27 | ACO1, aconitase 1, soluble | NM_002197 (SEQ ID NOS: 7/8) | 9p22 | Negative regulation of translation |
| AGCTGAGCTA (SEQ ID NO: 85) | 3 | 0 | 11 | DNASE2, deoxyribonu- clease II, lysosomal | NM_001375 (SEQ ID NOS: 17/18) | 19p13 | DNA metabolism |
| TAATGTATTC (SEQ ID NO: 86) | 1 | 0 | 23 | Hypothetical protein FLJ13576 | NM_022484 (SEQ ID NOS: 19/20) | 7q31.32 | ND |
| GCTTTACTTT (SEQ ID NO: 87) | 5 | 0 | 27 | ITM1- Integral membrane protein ID[10] | NM_152713 (SEQ ID NOS: 9/10) | 11q23 | Protein amino acid glycosylation |
| TAAATACTTG (SEQ ID NO: 88) | 1 | 0 | 43 | PDK4 -Pyruvate dehydro- genase kinase 4 | NM_002612 (SEQ ID NOS: 21/22) | 7q21.3 | Signal transduction |
| GCGCATCAAA (SEQ ID NO: 49) | 0 | 0 | 15 | LOC92196, EST weakly similar to death- associated protein 1 | XM_043500 (SEQ ID NOS: 23/24) | 2q24 | Apoptosis |
| AGCAGGGCTC (SEQ ID NO: 90) | 4 | 0 | 17 | PPP1R14B - protein phosphatase 1, regula- tory subunit 14B | XM_370630 (SEQ ID NOS: 25/26) | 11q13 | Cell-cell signaling |
| Transcripts up regulated in FTA | | | | | | | |
| CAGATAAGTT (SEQ ID NO: 91) | 3 | 12 | 0 | COL14A1, collagen, type XIV, α1 (undulin) | XM_044622 (SEQ ID NOS: 27/28) | 8q23 | Cell-cell adhesion |
| CTTCAATCTT (SEQ ID NO: 92) | 7 | 37 | 0 | TARSH - target of NESH- SH3 protein | NM_015429 (SEQ ID NOS: 11/12) | 3q12 | ND |
| GAGAGGAAGG (SEQ ID NO: 93) | 3 | 34 | 0 | Putative Emu 1 | NM_133455.1 (SEQ ID NOS: 29/30) | 22q12.2 | ND |
| TGATCAATAT (SEQ ID NO: 94) | 3 | 10 | 0 | NID2 | NM_007361.1 (SEQ ID NOS: 31/32) | 14q21 | Cell adhesion |
| GGTATGCTGT (SEQ ID NO: 95) | 2 | 10 | 0 | EDNRB, Endothelial receptor type B | NM_000115.1 (SEQ ID NOS: 33/34) | 13q22 | G-protein coupled receptor pathway |
| Genes involved in thyroid function | | | | | | | |
| GATGAATAAA (SEQ ID NO: 96) | 75 | 38 | 0 | TPO, Thyroid peroxidase | M17755 (SEQ ID NOS: 35/36) | 2p25 | Thyroid hormone generation |
| CGGTGAAGCA (SEQ ID NO: 97) | 134 | 67 | 130 | TG, Thyroglobulin | NM_003235 (SEQ ID NOS: 37/38) | 8q24.2 | Thyroid hormone generation |

TABLE 1-continued

Validated FTA and FTC differentially expressed genes and thyroid specific genes

| Tag sequence | Normal[7] | Adenoma[7] | Carcinoma[7] | Transcript description[8] | GenBank Accession (SEQ ID NOS: nucleotide/ amino acid) | Gene Location | Gene ontology[9] |
|---|---|---|---|---|---|---|---|
| ATGCTAAGAG (SEQ ID NO: 98) | 30 | 13 | 63 | DIO2, Deiodinase, iodothyronine, type II | NM_000793 (SEQ ID NOS: 39/40) | 14q24.2 | Thyroid hormone generation |

[7]SAGE tags counts shown are after normalization to 100,000.
[8]Tag sequences were mapped to transcript sequence, confirmed by PCR and used to determine gene name and accession number.
[9]Gene classification was by biological process, ND- gene classification not defined.
[10]Genes differentially expressed in this study.

Four genes, DDIT3, ARG2, ITM1, and C1orf24, were found to have significant differential expression on an independent set of tumors. Interestingly, DDIT3, ARG2, and ACO1 can be modulated by hypoxia (33,55). Thus, we looked for CA9 expression in thyroid cancer since it is a hypoxia marker in other tumors (56). A higher expression of CA9 was found in 2 cases of FTCs which had a higher level of DDIT3 and ARG expression, but was not found in FTAs and normal tissues. Further testing is needed to determine whether hypoxia detected by CA9 is a marker for survival in thyroid carcinomas as it is in other tumors (57).

In addition to the markers of the present invention, SAGE also allowed identification of new genes, which mapped to a chromosome region that has already been described as important in thyroid carcinogenesis. A new hypothetical protein, FLJ13576, mapped to 7q31-32, and was over-expressed in 70% of FTC and the 2 FTA cases (cases 6 and 8, Table 2). This hypothetical protein contains a fibronectin type III domain, one of three types of internal repeats within the plasma protein fibronectin. The 7q31-32 locus contains other genes involved in thyroid carcinogenesis, such as the MET oncogene (53,54). Other genes mapped in this region were found such as SLC26A4 (solute carrier family 26, member 4) and NRCAM (neuronal cell adhesion molecule) and were found overexpressed in the FTC SAGE library. These results, in agreement with those obtained from comparative genomic hybridization analysis, where the observed gain of 7q31 and 7q21.1-q21.2 was the most frequent chromosomal imbalance in FTC, suggest that this locus duplication could be involved in thyroid carcinogenesis (51).

Since follicular cell interaction and differentiation is guided by a variety of factors, such as extracellular matrix glycoprotein and receptor and cell adhesion molecules, we also expected to find genes involved in this process to be differentially expressed between FTC and FTA. In fact, ODZ1 (tenascin M), ANXA1 (annexin 1), LAMB1 (laminin beta 1), MYL6 (myosin, light polypeptide 6), MSN (moesin), CLU (clusterin), TMSB4X (thymosin, beta 4), SPARC (osteonectin), CLDN1 (claudin 1), NID2 (nidogen 2), Emu 1, CANX (calnexin), SDC2 (syndecan 2), FMOD (fibromodulin), CDH1 (cadherin 1) and COL14A1 (undulin) were found differentially expressed in thyroid SAGE libraries. Some of these genes were described previously as being involved in thyroid tumor genesis, but they were not used to discriminate between FTA and FTC (30,58).

Example 2

RT-PCR Analysis of Genes Identified by Sage Analysis to Confirm Expression Level To validate the differential gene expression profile predicted by SAGE, seventeen genes with the highest fold-induction were tested and analyzed for gene expression by quantitative real-time RT-PCR.

Tissue Samples.

For RT-PCR analysis, twenty-three primary tumors were obtained from patients initially diagnosed with follicular thyroid tumor. The tumors were frozen immediately after surgical biopsy. All samples were obtained from patients followed at Hospital São Paulo, Universidade Federal de São Paulo, and Hospital Helópolis, São Paulo, Brazil. The study was approved by the Ethics and Research Committees of the Universidade Federal de São Paulo and Hospital Heliópolis and was in agreement with the 1975 Helsinki statement, revised in 1983. A signed letter of informed consent was obtained from each patient. All patients received post-surgical radioiodine ablation and suppressive thyroxine therapy. Tumor recurrence was observed in three cases of FTC (Table 2). Tissue histology confirmed the initial diagnoses, as summarized in Table 2. Samples included ten FTA and thirteen FTC biopsies. In addition, eight patient-matched normal tissues obtained from patients with FTC (n=5) and FTA (n=3) were analyzed. Universal human reference total RNA (Stratagene, La Jolla, Calif., USA) was used as a control.

TABLE 2

Clinical and histologic data of patients tested by real time RT-PCR

| Case No. | Diagnosis | Sex | Age at diagnosis (years) | Nodule size (mm) | Recurrence | PAX8-PPARG Rearrangement |
|---|---|---|---|---|---|---|
| 1 | FTA | F | 70 | 34 | No | Yes |
| 2 | FTA | F | 31 | 35 | No | Yes |
| 3 | FTA | F | 29 | 40 | No | Yes |
| 4 | FTA | F | 39 | 40 | No | NF[11] |
| 5 | FTA | F | 44 | 80 | No | NF |
| 6 | FTA | F | 51 | 40 | No | NF |
| 7 | FTA | M | 45 | 30 | No | NF |
| 8 | FTA | F | 52 | 30 | No | NF |
| 9 | FTA | F | 12 | 7 | No | NF |
| 10 | FTA | F | 22 | 15 | No | NF |
| 11 | FTC | F | 38 | 35 | No | Yes |
| 12 | FTC | M | 28 | 48 | No | Yes |
| 13 | FTC | F | 25 | 32 | No | Yes |
| 14 | FTC | F | 76 | 62 | Yes | Yes |
| 15 | FTC | F | 40 | 19 | Yes | NF |
| 16 | FTC | F | 38 | 32 | No | NF |
| 17 | FTC | F | 48 | 16 | No | NF |
| 18 | FTC | F | 36 | 20 | No | NF |
| 19 | FTC | F | 45 | 45 | No | NF |
| 20 | FTC | F | 24 | 23 | No | NF |
| 21 | FTC | M | 68 | 100 | Yes | NF |

TABLE 2-continued

Clinical and histologic data of patients tested by real time RT-PCR

| Case No. | Diagnosis | Sex | Age at diagnosis (years) | Nodule size (mm) | Recurrence | PAX8-PPARG Rearrangement |
|---|---|---|---|---|---|---|
| 22 | FTC | F | 33 | 30 | No | NF |
| 23 | FTC | M | 66 | 90 | No | NF |

[11]Not found in patient.

Cell Lines.

The human follicular thyroid carcinoma cell line UCLA RO-82W-1 (WRO), the papillary thyroid carcinoma line UCLA NPA-87-1 (NPA), and an undifferentiated thyroid carcinoma cell line UCLA RO-81A-1 (ARO) were grown in DMEM (Invitrogen, Carlsbad, Calif., USA) supplemented with 10% FCS (Invitrogen) in a 5% $CO_2$ environment at 37° C., as previously reported (18).

RNA Isolation, cDNA Synthesis, and Quantitative RT-PCR.

Total RNA was isolated using RNAgents (Promega, Madison, Wis., USA), according to the manufacture's recommendation. One microgram of total RNA was treated with DNA-free (AMBION, Austin, Tex., USA) and was reverse-transcribed to cDNA using the Omniscript Reverse Transcriptase kit (QIAGEN, Germantown, Md., USA) with oligo(dT)$_{12-18}$ primer and ten units of RNase inhibitor (Invitrogen). Reverse transcriptase-negative samples were prepared for each individual reaction and were used as controls for detection of assay contamination. The cDNA was then diluted 5-fold, and 1.5 μl aliquots were used in 20-μl PCR reactions containing 10-μM of each specific primer, 1× IQ Supermix (BioRad, Hercules, Calif., USA), and SYBR-Green (Sigma, St. Louis, Mo., USA). The PCR reaction was performed for 40 cycles of a 4-step program: 94° C. for 30 seconds, annealing temperature for 15 seconds, 72° C. for 15 seconds, and a fluorescence-read step for 10 seconds. After PCR, a melting curve analysis was performed and the read temperature of each assay was set above the melting point of short primer-dimers and below that of the target PCR product. Quantitative PCR reactions were performed twice in triplicate. The threshold cycles (Ct) were obtained using iCycler software version 3.0 (BioRad) and were averaged (SD≦1). Gene expression was normalized using the average of two control genes (ribosomal protein S8 and t-complex 1), shown by SAGE to be at equivalent levels in all three SAGE libraries. A relative expression amount was calculated according to the formula $2^{(Rt-Et)}/2^{(Rn-En)}$. Rt is the Ct cycle number observed in the experimental sample for the two control genes. Et is the Ct cycle number observed in the experimental sample for the reference gene. Rn is the average Ct cycle number observed in ten adenomas for the two control genes. En is the average Ct cycle number observed in ten adenomas for the reference gene (22). FIG. 1 shows the relative expression levels of DDIT3, ARG2, ITM1, C1orf24, ACO1, and TARSH in normal tissue samples, ten FTA biopsy samples and thirteen FTC biopsy samples. The results obtained from fourteen of the seventeen relative expression levels in twenty-three samples and normal tissues were used for statistical analysis. Fourteen genes were used because three genes showed no difference by PCR. The PCR-specific primers, annealing temperatures, and fluorescence-read temperatures are summarized in Table 3. The PCR products were resolved by electrophoresis in a 3% agarose/ethidium gel.

TABLE 3

Primers and PCR conditions of selected genes and controls up regulated and down regulated in FTC

| Gene | Primer[12] | Annealing temp. | Read temp.[13] | Size (bp)[14] |
|---|---|---|---|---|
| Controls | | | | |
| RS8 | F: 5' AACAAGAAATACCGTGCCC 3' (SEQ ID NO: 41) R: 5' GTACGAACCAGCTCGTTATTAG 3' (SEQ ID NO: 42) | 55 | 83 | 125 |
| TCP1 | F: 5' CACTAGCAGTTAATGCTGCC 3' (SEQ ID NO: 43) R: 5' TGCTCAAATCAAGACCAATCC 3' (SEQ ID NO: 44) | 57 | 81 | 123 |
| Up regulated | | | | |
| DDIT3 | F: 5' GCGACAGAGCCAAAATCAGAG 3' (SEQ ID NO: 45) R: 5' AGTCAGCCAAGCCAGAGAAG 3' (SEQ ID NO: 46) | 55 | 84 | 316 |
| ARG2 | F: 5' GAAGGCATGTATATTGCTGAGG 3' (SEQ ID NO: 47) R: 5' TGAACTGGGAGTAGGAAGTTG 3' (SEQ ID NO: 48) | 54 | 84 | 204 |
| C1orf24 | F: 5' GCTTGATGAAACTCTGAAAGTG 3' (SEQ ID NO: 49) R: 5' AGAACTCCTGGCAGAATGG 3' (SEQ ID NO: 50) | 57 | 86 | 180 |

TABLE 3-continued

Primers and PCR conditions of selected genes and controls up regulated and down regulated in FTC

| Gene | Primer[12] | Annealing temp. | Read temp.[13] | Size (bp)[14] |
|---|---|---|---|---|
| PCSK2 | F: 5' CATCCCAGCCCCAATTTTC 3'<br>(SEQ ID NO: 51)<br>R: 5' AATACTCCTGTCGCCTCTC 3'<br>(SEQ ID NO: 52) | 54 | 86 | 183 |
| ODZ1 | F: 5' CGGCTTCAGACAAAAACTCAAG 3'<br>(SEQ ID NO: 53)<br>R: 5' AGAAGGGACAGCAGCAAAC 3'<br>(SEQ ID NO: 54) | 57 | 83 | 180 |
| ACO1 | F: 5' TTTGAGAAAGAGCCATTGGGAG 3'<br>(SEQ ID NO: 55)<br>R: 5' TAGCAGCACATAGGCATCCAC 3'<br>(SEQ ID NO: 56) | 54 | 83 | 300 |
| DNASE2 | F: 5' TTCCCTTCGCTCAGTTCTC 3'<br>(SEQ ID NO: 57)<br>R: 5' ATGCCTACAGTTTTGTGCC 3'<br>(SEQ ID NO: 58) | 54 | 87 | 301 |
| FLJ13576 | F: 5' ATTTCAGAGCAGTTGGTGTT 3'<br>(SEQ ID NO: 59)<br>R: 5' GTTACCCAATTCATGGAAGA 3'<br>(SEQ ID NO: 60) | 51.8 | 82.5 | 153 |
| ITM1 | F: 5' AGGCCTCACTGGGTATTCT 3'<br>(SEQ ID NO: 61)<br>R: 5' TATCCTGACCAGCCAATGTTC 3'<br>(SEQ ID NO: 62) | 56 | 85 | 324 |
| PDK4 | F: 5' CGCCTGTGATGGATAATTCC 3'<br>(SEQ ID NO: 63)<br>R: 5' AGCATCTGTTCCATATCCTGA 3'<br>(SEQ ID NO: 64) | 54 | 81 | 120 |
| DAP1 | F: 5' GAAAACAAGTGCCATTGCAAA 3'<br>(SEQ ID NO: 65)<br>R: 5' GCTAAGCTGTCAGATATTT 3'<br>(SEQ ID NO: 66) | 53 | 83 | 243 |
| PPP1R14B[15] | F: 5' CAGCAGGCCAGAAATGAAG 3'<br>(SEQ ID NO: 67)<br>R: 5' CGTCAAGTATGACCGCAAG 3'<br>(SEQ ID NO: 68) | 54 | 87 | 226 |
| Down regulated | | | | |
| COL14A1 | F: 5' CTGCCATCCTCAACCAGATT 3'<br>(SEQ ID NO: 69)<br>R: 5' AACGCCTGGATTTCCTTTTT 3'<br>(SEQ ID NO: 70) | 55 | 88 | 211 |
| TARSH | F: 5' TACTAGGCCCAAACCCAGTG 3'<br>(SEQ ID NO: 71)<br>R: 5' CCTGGCTTTCCAGTGACATT 3'<br>(SEQ ID NO: 72) | 54 | 81 | 213 |
| Emu1 | F: 5' TAAGGGAGACCCTGGTGAGAAG 3'<br>(SEQ ID NO: 73)<br>R: 5' ACCCCAGCTCTGGTTCATAG 3'<br>(SEQ ID NO: 74) | 54 | 83 | 131 |
| NID2 | F: 5' GTGCCGGAGTGGTTATGAGT 3'<br>(SEQ ID NO: 75)<br>R: 5' TAGCTGCAGGGTGACATCTG 3'<br>(SEQ ID NO: 76) | 54 | 86 | 233 |

TABLE 3-continued

Primers and PCR conditions of selected genes and controls up regulated and down regulated in FTC

| Gene | Primer[12] | Annealing temp. | Read temp.[13] | Size (bp)[14] |
|---|---|---|---|---|
| EDNRB[16] | F: 5' TCCCGTTCAGAAGACAGCTT 3' (SEQ ID NO: 77) R: 5' CACGAGGGCAAAGACAAGGAC 3' (SEQ ID NO: 78) | 57 | 83 | 231 |

[12]Specific primers that corresponded to exon-intron boundaries and were designed using Seq Web version 2.
[13]Fluorescence-read temperature.
[14]PCR product size.
[15]Not confirmed by RT-PCR.
[16]Not confirmed by RT-PCR.

The results obtained from SAGE were compared with those obtained from RT-PCR analysis for the samples used to generate FTA and FTC libraries (cases 5 and 12, respectively). When RT-PCR and the original samples were used, fourteen of seventeen genes showed the predicted difference between FTA and FTC, and three did not.

Using the full panel of samples, nine of twelve FTC samples over-expressed transcripts maintained high expression in 50%-100% of FTCs tested, compared with the expression of same transcript in FTA and patient-matched normal tissue. DDIT3 (DNA-damage-inducible transcript 3) and ARG2 (arginase type II) were expressed at higher levels in FTCs. The increased average of expression was ≧5-fold in nearly all FTCs and some exhibited at least 11-fold higher levels as predicted by SAGE. The gene ITM1 (integral membrane protein 1) was expressed in all FTCs, with low levels of expression in six FTAs. The genes C1orf24 (niban) and ACO1 (aconitase 1) were expressed in 76% of FTCs, with low but detectable expression in 40% of FTAs. The hypothetical protein FLJ13576 was expressed in 67% of FTCs and in two cases of FTAs (cases 6 and 8). Six genes did not distinguish well: ODZ1, PCSK2 (proprotein convertase subtilisin/kexin type 2), DNASE2 (deoxyribonuclease II, lysosomal), LOC92196 (EST weakly similar to death-associated protein-1), PDK4 (pyruvate dehydrogenase kinase-4), and PPP1R14B (protein phosphatase-1, regulatory subunit-14B) were expressed in 30%-69% FTCs and in about 30%-40% of FTAs.

Of the fine genes predicted to be FTA specific, the TARSH gene was the only gene expressed at high levels in normal thyroid tissue and FTA tissue and not expressed in FTC tissue. Therefore, TARSH is a marker for diagnosing FTA. The genes putative Emu1, NID2, COL14A1, and endothelial receptor type B were expressed in about 60%-80% of FTCs and were not discriminatory between FTA and FTC. The RT-PCR results from the six genes that appeared to discriminate between FTC and FTA are summarized in FIG. 1. Although DDIT3 and ITM1 transcripts were elevated in most FTC cases, use of DDIT3 independently, for example, to identify tumors, could misclassify the case 14, which have low levels of DDIT3 but express ITM1 and ARG2 at higher levels (FIG. 1).

In addition, the expression levels of selected genes were analyzed in three well-characterized thyroid cell lines from different types of thyroid tumors (18, 27, 28). All the transcripts elevated in FTCs (see Table 1) were expressed in all thyroid cell lines. The expression of the candidate markers in the pure populations of cultured carcinoma cells indicates that the expression is due to the malignant component of the tumor. Conversely, the genes down regulated in the FTC library were present at lower levels or absent in the cell lines.

PPARG-PAX8 Rearrangement

All patient tissue samples tested by RT-PCR were concomitantly tested for the presence of PPARG-PAX8. Analysis revealed that the rearrangement between PPARG-PAX8, previously identified as a FTC marker (9), was found in about 33% of FTAs, and in 33% of FTC (Nakabashi et al., manuscript in preparation) and did not distinguish between adenoma and carcinoma (Table 2). The clinical and pathologic information was compared with the results obtained from quantitative RT-PCR analysis. Using the cross validation procedure, the prediction accuracy was estimated to be 83%. Four of the cases were misclassified (cases 6, 8, 13 and 21—Table 2). Case 6, which exhibited DDIT3, ARG2, and ITM1 expression, was re-evaluated by an experienced pathologist and showed no evidence of either capsule or blood vessel invasion. However, Hashimoto's thyroiditis and positive staining for both ERBB2 and P53 was reported. In case 8, Hashimoto's thyroiditis was also related. A longer follow-up for both cases will reveal whether they are true FTAs. Case 13 is a FTC that was diagnosed as minimally invasive. Case 21, however, is a FTC where both blood and capsule invasion were present.

Example 3

Analysis of Gene Expression by Immunohistochemical Staining

The expression levels of two genes (DDIT3 and ARG2) were confirmed by immunohistochemistry. For the immunohistochemical study pathologic materials were retrieved from specimens diagnosed with FTC (n=27) and FTA (n=32) at Hospital São Paulo, Federal University of São Paulo in an eight-year period from 1996-2003. Hematoxylin and eosin-stained sections were reviewed by an experienced pathologist.

Immunohistochemical Analysis.

Immunohistochemical staining was performed on paraffin-embedded tissue sections (3 µm) placed on 0.1% poly-lysine-coated slides (Sigma), deparaffinized with xylene and rehydrated through a series of graded alcohols. The endogenous alkaline phosphatase activity was blocked by 3% hydrogen peroxide. After pressure-cooking retrieval (10 mmol/L citrate buffer, pH 7.4 for 2 minutes), the sections were blocked in 1×PBS/0.1% BSA for 1 hour at room temperature and incubated with the first antibody for at least 16 hours at 4° C. The labelled streptavidin biotin reagents complex was used (DAKO LSAB+ kit, HRP; Dako Corp, Carpinteria, Calif., USA) with DAB as a substrate (Sigma). Hematoxylin was used as the nuclear counterstain. The slides were mounted in DAKO Faramount mounting medium (Dako Corp) and were examined by light microscopy. The immunopositivity was evaluated by two independent observers in a semiquantitative fashion in which the relative abundance of each antigen was evaluated by counting 1000 cells in at least five randomly chosen fields of the tissue sections at ×400 magnification and scored as follows: negative (−), weak (+), moderately abundant (++), and strong (+++). For two of the genes, DDIT3 and ARG2, antibodies were commercially available. Polyclonal antiserum GADD153, originated against a peptide mapping at the C-terminus of DDIT3 of human origin, was used at 1:200 dilution (R-20; Santa Cruz Biotechnologies Inc., Santa Cruz, Calif., USA). Polyclonal antiserum arginase II, raised against a recombinant protein to amino acids 291-354 mapping at the C-terminus of arginase II of human origin, was used at 1:100 dilution (H-64; Santa Cruz Biotechnologies Inc). Monoclonal mouse anti-human von Willebrand factor VIII was used at 1:25 dilution (M0616; Dako Corp). CA9 mouse monoclonal G250 antibody (gift of E. Oosterwijk, University Medical Center, Nijmegen, The Netherlands) was used at 1:400 dilution. The control for antibody specificity included incubation with rat IgG, used in the same concentration as the first antibody (Vector Laboratories). Positive and negative controls were included in each run.

Figure 3:
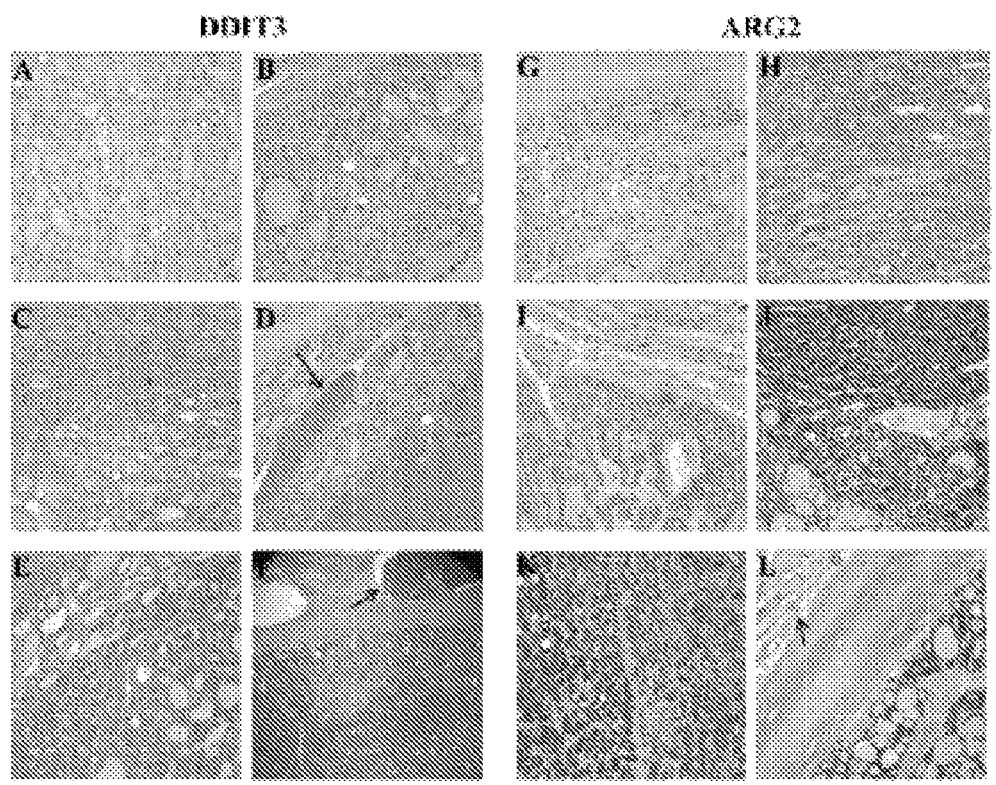
FIGS. 3A to 3L show immunohistochemical analysis of DDIT3 (FIGS. 3A-3F) and ARG2 (FIGS. 3G-3L) in paraffin embedded sections of FTA tissue and FTC tissue. FTC tissue exhibited strong brown immunostaining for DDIT3 (FIGS. 3D, 3E and 3F) and ARG2 (FIGS. 3J, 3K and 3L). In contrast, FTA tissue (FIGS. 3A, 3B, 3C, 3G, 3H and 3I) exhibited no immunoreactivity. The arrow in FIGS. 3D and 3F shows the vascular invasion in the FTC tissue and the follicular cells that are positive for DDIT3. The arrow in FIG. 3L shows normal thyroid tissue that was negative for ARG2 adjacent to a tumor area that was positive for ARG2. Hematoxylin was used as a nuclear counter stain. Original magnification is ×100 for FIGS. 3A-3E and 3G-3L, ×40 for FIG. 3F.

The results are summarized in table 4 (to details see Table 5). Staining for DDIT3 expression (GADD153 antibody) showed a moderate to strong (++/+++) expression in twenty-three FTCs (85.2%). The staining was detected in both the nucleus and the cytoplasm of neoplastic follicular cells (FIGS. 3D, 3E and 3F). Adjacent nonneoplastic thyroid tissue did not stain. Three of four FTCs negative for DDIT3 staining were FTC minimally invasive (focal capsular and vascular invasion) and one was moderately differentiated. No nuclear and cytoplasmic staining in epithelial cells was observed in twenty nine (90.6%) sections from FTAs (FIGS. 3A, 3B and 3C) and IgG-negative controls. A weak or moderate staining for DDIT3 was found in 3 (9.4%) of FTAs. Two of three were diagnosed as hürthle cell adenoma (HCA) and one was an atypical adenoma (data not shown). Immunohistochemistry analysis revealed the expression of DDIT3 in three FTAs, which were diagnosed as atypical adenoma and hürthle cell adenoma (Table 5). This results support the idea that some follicular hürthle tumors should be considered a separate thyroid cancer class and few FTAs are early in situ carcinomas with malignant potential. Longer follow-up will be needed to determine whether these tumors are a less benign variant. In addition, both follicular lesions coexisted with Hashimoto's thyroiditis, which is a possible source of diagnostic error (9). Immunohisotchemistry analysis in a large set of hürthle adenomas would be necessary to better understand whether the use of additional class predicted gene in combination with DDIT3 and ARG2 can better classify these type of follicular lesions or if additional profiling is necessary to find new markers for the hürthle subtype.

TABLE 4

Immunoreactivity for DDIT3 and ARG2 in FTA and FTC.

| Immunoexpression[17] | Follicular Thyroid Adenoma (n = 32) | Follicular Thyroid Carcinoma (n = 27) |
|---|---|---|
| DDIT3 | | |
| − | 29 (90.6%) | 4 (14.8%) |
| + | 2 (6.3%) | 0 |
| ++ | 1 (3.1%) | 5 (18.5%) |
| +++ | 0 | 18 (66.7%) |
| ARG2 | | |
| − | 29 (90.6%) | 4 (14.8%) |
| + | 1 (3.1%) | 0 |
| ++ | 2 (6.3%) | 2 (7.4%) |
| +++ | 0 | 21 (77.8%) |
| DDIT3/ARG2 (−/−) | 29 | 3 |
| DDIT3/ARG2 (−/+) | 0 | 1 |
| DDIT3/ARG2 (+/−) | 0 | 1 |
| DDIT3/ARG2 (+/+) | 3 | 23 |

TABLE 5

Clinical and Pathological features of FTA and FTC analyzed by immunohistochemistry to DDIT3 and ARG2.

| Case No. | FNA[18] | SEX[19] | AGE | DDIT3[20] | ARG2[20] |
|---|---|---|---|---|---|
| FTA (n = 32) | | | | | |
| 1 | SUS | F | 23 | (−) | (−) |
| 2 | BNG | F | 54 | (−) | (−) |
| 3 | SUS | F | 30 | (−) | (−) |
| 4 | SUS | F | 42 | (−) | (−) |
| 5 | SUS | F | 39 | (−) | (−) |
| 6 | SUS | F | 39 | (−) | (−) |
| 7 | SUS | F | 27 | (−) | (−) |
| 8 | SUS | F | 39 | (−) | (−) |
| 9[21] | SUS | F | 16 | (++) | (+) |
| 10 | BNG | F | 47 | (−) | (−) |
| 11 | SUS | F | 51 | (−) | (−) |
| 12 | SUS | F | 17 | (−) | (−) |
| 13 | SUS | M | 42 | (−) | (−) |
| 14 | NA | F | 54 | (−) | (−) |
| 15 | SUS | M | 74 | (−) | (−) |
| 16 | NA | F | 22 | (−) | (−) |
| 17 | NA | M | 51 | (−) | (−) |
| 18 | SUS | M | 53 | (−) | (−) |
| 19 | SUS | F | 38 | (−) | (−) |
| 20 | NA | M | 55 | (−) | (−) |
| 21 | SUS | F | 37 | (−) | (−) |
| 22 | SUS | F | 38 | (−) | (−) |
| 23 | SUS | F | 49 | (−) | (−) |
| 24 | SUS | F | 62 | (−) | (−) |
| 25 | NA | F | 34 | (−) | (−) |
| 26 | BNG | F | 43 | (−) | (−) |
| 27 | NA | F | 29 | (−) | (−) |
| 28 | NA | F | 72 | (−) | (−) |
| 29 | NA | F | NA | (−) | (−) |
| 30 | NA | M | 38 | (−) | (−) |
| 31[22] | SUS | F | 34 | (+) | (++) |
| 32[22] | SUS | F | 29 | (+) | (++) |
| FTC (n = 27) | | | | | |
| 33 | SUS | F | 68 | (+++) | (+++) |
| 34 | SUS | F | 17 | (++) | (+++) |
| 35 | SUS | F | 49 | (+++) | (+++) |
| 36 | SUS | F | 61 | (+++) | (+++) |
| 37[23] | SUS | F | 33 | (−) | (−) |
| 38 | SUS | F | 61 | (+++) | (+++) |
| 39 | NA | F | 21 | (++) | (++) |
| 40[24] | | M | 75 | (−) | (++) |
| 41[23] | | F | 23 | (−) | (−) |
| 42 | | M | 62 | (+++) | (+++) |
| 43[23] | CA | M | 66 | (−) | (−) |
| 44 | CA | M | 75 | (+++) | (++) |
| 45 | NA | F | 60 | (+++) | (+++) |
| 46 | NA | F | 52 | (++) | (++) |
| 47 | NA | F | 76 | (++) | (++) |
| 48 | | F | 47 | (+++) | (+++) |
| 49 | NA | F | 75 | (+++) | (+++) |
| 50 | | M | 36 | (+++) | (+++) |
| 51 | NA | F | NA | (+++) | (+++) |
| 52[23] | | F | 24 | (++) | (−) |
| 53 | NA | F | 59 | (+++) | (+++) |
| 54 | | F | 69 | (+++) | (++) |

TABLE 5-continued

Clinical and Pathological features of FTA and FTC analyzed by immunohistochemistry to DDIT3 and ARG2.

| Case No. | FNA[18] | SEX[19] | AGE | DDIT3[20] | ARG2[20] |
|---|---|---|---|---|---|
| 55 | NA | F | 38 | (++) | (+++) |
| 56 | NA | M | 31 | (+++) | (+++) |
| 57 |    | F | 66 | (++) | (+++) |
| 58 |    | F | 59 | (+++) | (++) |
| 59 |    | F | 34 | (+++) | (+++) |

[17]Negative (−), Positive (+). The intensity was scored into three categories: weak (+), moderate (++), strong (+++)
[18]Results obtained from FNA biopsy. (SUS) suspicious, non-available (NA), cancer (CA) and benign (BNG).
[19]Female (F) and Male (M).
[20]Negative (−), Positive (+). The intensity was scored into three categories: weak (+), moderate (++), strong (+++)
[21]Atypical adenoma.
[22]Hürthle cell adenoma.
[23]Minimally invasive.
[24]Moderately differentiated In this study, over expression of DDIT3 transcript was found in FTCs and thyroid cancer cell lines Immunohistochemistry showed DDIT3 protein expression was moderate to strong in twenty three (82.5%) of FTCs, and specific for the follicular cells of the tumor (FIGS. 3A-3F). No expression of DDIT3 was found in four FTCs, three of which were diagnosed as minimally invasive. This observation suggested a correlation with DDIT3 expression and capsular and vascular invasion. Barden et al. (16), by oligonucleotide array, found the gene DDIT3 up regulated in FTC and the genes putative Emu1 and NID2 up regulated in FTA. The investigators did not validate the expression of these genes in a set of samples. Interestingly, Nikiforova et al. (35) reported that 85% of FTC could develop through non-overlapping RAS or PAX8-PPARG pathways. The authors suggested that RAS activation by itself appears insufficient to determine malignant growth but may predispose to acquisition of additional genetic or epigenetic alteration that lead to a fully transformed phenotype. Brenner et al. showed a signaling cascade from FAS receptor via the G proteins RAS and RAC to JNK/p38-K and the transcription factor DDIT3 (36). Expression of DDIT3 was also elevated after induction with thiazolidinedione via PPARG1 (37). It is therefore possible that either or both of these pathways activate DDIT3 expression.

ARG2 staining was consistently negative in twenty nine of FTAs (90.6%,) and adjacent nonneoplastic thyroid tissue, whereas specific staining was found in the cytoplasm of neoplastic follicular thyroid cells in twenty three of FTCs (85.2%) analyzed (FIGS. 3G, 3H, 3I, 3J, 3K and 3L). All four FTCs, negative for ARG2 were diagnosed as minimally invasive.

Overall, a moderate/strong expression of ARG2 and DDIT3 were observed in 85.2% of FTCs, whereas 90.6% of FTAs were negative, indicating the utility of these antibody to discriminate FTC from FTA. In addition, the immunoreactivity with both antibodies in FTCs were more often diffuse than focal and stronger intensity in comparison with those observed in the four cases of FTAs.

Staining with von Willebrand factor VIII was used to distinguish endothelial cells in all tissues. Moderate expression of CA9 was observed in 2 FTCs (cases 11 and 12), but not in FTAs and normal tissues (data not shown).

Example 4

Statistical Analysis for a Class Predictor to Differentiate FTA from FTC

To identify genes for which expression levels were statistically significant between FTA and FTC, the relative expression data obtained from RT-PCR analysis on fourteen of seventeen genes (FIG. 1) were used. The initial comparison of expression levels was carried out using rank based (Wilcoxon rank sum) and mean based (Student's t) tests. Data were log transformed before applying the Student's t test. A comparison was designated as statistically significant if either the rank-sum statistic or the corresponding t-statistic was found to be significant, using an alpha level that had been adjusted (using a Bonferroni adjustment) to keep the family wise error rate at 0.10. Next, development of an expression-based model that could be used to predict class of diagnosis for the tumor (FTA or FTC) was investigated. The framework outlined by Radmacher et al. (23) was followed, and the prediction method we used was the compound covariate predictor for gene expression data (23, 24). The performance of the predictor was tested using leave-one-out cross-validation for all steps of the prediction procedure (i.e., selection of differentially expressed genes as well as creation of the prediction rule) (23, 25). The significance of the performance of the predictor using the permutation based test outlined in Radmacher et al. (23) was assessed, in which the class labels are randomly permuted and the proportion of data sets that have a cross validated error rate as small as observed in the data set was calculated. Because it was prohibitive to compute all possible permutations, 2000 random permutations were used to estimate the achieved significance level. The concordance of the results of the immunohistochemistry staining and the pathological identification of class (FTC vs. FTA) was estimated using a kappa statistic and constructing a 95% confidence interval (Kramer and Feinstein 1981). The use of kappa corrects for agreements between the two methods (immunohistochemistry and pathology) expected by chance. The maximum value of kappa, corresponding to perfect agreement, is 1.0. Kramer and Feinstein (1981) suggested guidelines to assess the significance of the magnitude of the statistic.

Genes were declared different between the 2 groups if the P value was less than the family-wise error rate of 0.10. The Wilcoxon test showed that the difference in gene expression of DDIT3, ARG2, and ITM1 was statistically significantly at the 0.05 level. Expression of an additional gene (C1orf24) was statistically significant at the 0.10 level. The Student's t test showed that genes DDIT3 and ITM1 were significant at the 0.05 level. No additional genes were significant at the 0.10 level. Thus, expression levels of four genes (DDIT3, ARG2, ITM1, and C1orf24) were declared significantly different between the two groups; expression levels of DDIT3 and ITM1 were declared significantly different by both analyses.

The class predictor used genes in which expression levels were found significantly different at the 0.10 level using the t test. The sample t statistics were used as weights in the compound covariate predictor. To evaluate the predictor, the leave-one-out cross-validation was used: for each sample, in turn, one sample was left out, and the predictor was developed on the remaining twenty two samples. The left-out sample was predicted. All the steps of the prediction procedure were used including selection of differentially expressed genes, as well as creation of the prediction rule (23, 25). Using leave-one-out cross validation, nineteen of the twenty three (83%) samples were correctly predicted. To assess the significance of these prediction results, a permutation test (23, 25) was implemented. The proportion of random permutations with four or fewer misclassifications was 0.007. Thus, the results of the prediction analysis were found significant. Two of the genes, DDIT3 and ITM1, were always selected in each step of the cross validation procedure (i.e., each time a sample was left out). In the Wilcoxon test, ARG2 was statistically significantly at the 0.05 level. An additional gene, C1orf24, expressed in most of the FTCs, can be a predictor. Even when starting with only one SAGE library per tumor to predict candidate markers, and faced with heterogeneous gene expression in FTA and FTC, we were still able to find consistent and statistically significant markers. However, future studies using this simple SAGE-based method to identify tumor markers would likely benefit from using two or more libraries of each representative tumor type. SAGE has been previously used for a shallower transcript sampling of thyroid tissue, but not specifically directed toward distinguishing between FTA and FTC (29-31). Using deep sampling of representative FTC and FTA cases allowed application of selection criteria for candidate genes that were likely to have large differences in expression that could be easily detected by immunohistochemistry.

Figure 2:
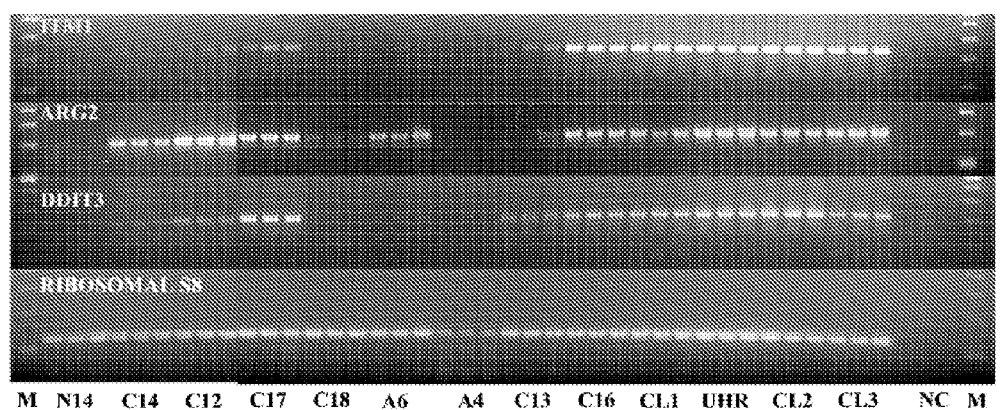
FIG. 2 shows quantitative RT-PCR products of three statistically significant genes (ITM1, ARG2, and DDIT3). The samples shown are FTAs (A), FTCs (C), normal thyroid tissues (N), thyroid carcinoma cell lines (CL) and negative control (NC). Genes DDIT3, ARG2, and ITM1 are expressed in most of the FTCs, the thyroid follicular carcinoma cell line (CL1), the papillary thyroid carcinoma cell line (CL2), and the undifferentiated thyroid carcinoma cell line (CL3), but not in normal and most FTAs. Case 6 (A6) expressed ARG2 and ITM1 and was misclassified according to our class-predicted genes. Universal human RNA (HUR) was used as a control. Ribosomal protein 8 is shown as a calibrator gene. The 100-bp DNA ladder (M) is shown in the far left and far right lanes. The results are shown in triplicate, and the numbers correspond to cases analyzed (Table 2). The product sizes are summarized in Table 3.

FIG. 2 shows the final products for three genes, the differential expression of which was shown to be statistically significant at the 0.05 level, after running forty cycles of PCR using templates from FTC, FTA, normal thyroid, and cell lines.

The concordance between the results of the immunohistochemistry staining on an independent set of tumors and the diagnosis by histopathology was estimated by kappa. The estimated kappa was 0.76 with a 95% confidence interval of [0.59, 0.93]. The value of 0.76 corresponds to a substantial strength of agreement based on previously developed guidelines (Kramer and Feinstein 1981).

Example 5

TARSH and its Binding Partner NESH can Repress Cell Invasion Phenotype In Vitro

To investigate whether TARSH and its partner NESH could repress cell invasion in vitro, TARSH and NESH full-length cDNAs were re-expressed in two thyroid carcinoma cell lines ARO and WRO. These cell lines have an invasive phenotype (27, 28).

In Vitro Invasion Assay.

A neomycin-selectable expression vector pcDNA3.1 (Invitrogen) containing a full-length wildtype (wt) human TARSH was stably transfected into ARO and WRO thyroid carcinoma cell lines. Additionally, a full-length cDNA of NESH, TARSH partner, was transfected into ARO and WRO cell lines (gift of S. Matsuda, Nagoya University School of Medicine, Nagoya, Japan). Cells ($5 \times 10^6$) were transfected using Bio-Rad Gene Pulser according to the manufacturer's instruction (Bio-Rad). Neomycin resistant colonies were initially selected on plates containing 800 µg/mL geneticin (G418; Gibco-BRL, Gaithersburg, Md., USA) and maintained in culture medium containing 600 µg/mL geneticin. As a control, cells were transfected with pcDNA3.1 and selected as described above. Two stable transfected clones for TARSH, NESH and a control were selected and used for an invasion assay using a BD Biocoat Matrigel Invasion Chamber as described by the manufacture (Becton Dickson Labware, Bedford, Mass., USA). Briefly, the invasion chamber (with Matrixgel matrix) and control chamber (without Matrixgel matrix) were rehydrated and $2.5 \times 10^4$ cells were plated to the chambers containing Matrigel matrix and control chamber wells without matrix. Twenty-four hours later, the cells on the lower side of the chambers were fixed and stained with Baxter Diff-Quik stain kit (Dade Behring, Newark, Del., USA) and random fields were counted under the light microscopy with a standardized grid. The plates were done in triplicates and the invasion index was expressed by the percent of cells that invade through occluded membrane (Invasion Chamber) divided by the percent of cells that migrated trough the uncoated membrane (control insert).

The invasion index observed was 7.5 and 5.1 respectively for control chambers compared to invasion chambers. An elevated migratory response was observed in control chamber, compared to the invasion chamber. Additionally, the number of invading cells from clones with vector only were compared to the number of invading cells from clones that re-expressed TARSH or NESH. The results obtained were similar to those obtained with control vs. invasion chamber. Even though these are preliminary results, it suggests that TARSH and NESH re-expression in thyroid carcinoma cell lines suppress cell motility and invasion. It is perhaps not too surprising that expression of some of the genes differing between adenoma and carcinoma might be involved in tumor invasion, a main distinguishing feature between benign and malignant tumors.

REFERENCES

1. Gharib, H. 1994. Fine-needle aspiration biopsy of thyroid nodules: advantages, limitations, and effect. *Mayo Clin Proc.* 69:44-49.
2. Mazzaferri, E. L. 1993. Management of a solitary thyroid nodule. *N Engl J Med.* 328:553-559.
3. Goellener, J. R., Gharib, H., Grant, C. S., Johnson, D. A. 1987. Fine-needle aspiration cytology of the thyroid, 1980 to 1986. *Acta Cytol.* 31:587-590.
4. Inohara, H., Honjo, Y., Yoshii, T., Akahani, S., Yoshida, J., Hattori, K., Okamoto, S., Sawada, T., Raz, A., and Kubo, T. 1999. Expression of ga lectin-3 in fineneedle aspirates as a diagnostic marker differentiating benign from malignant thyroid neoplasms. *Cancer.* 85:2475-2484.
5. Bartolazzi, A., et al. 2001. Application of an immunodiagnostic method for improving pre-operative diagnosis of nodular thyroid lesions. *Lancet.* 357:1644-1650.
6. Xu, X. C., el-Naggar, A. K., and Lotan, R. 1995. Differential expression of galectin-1 and galectin-3 in thyroid tumors. Potential diagnostic implications. *Am J Pathol.* 147:815-822.
7. Cvejic, D., Savin, S., Paunovic, I., Tatic, S., Havelka, M., and Sinadinovic, J. 1998. Immunohistochemical localization of galectin-3 in malignant and benign human thyroid tissue. *Anticancer Res.* 18:2637-2641.
8. Bernet, V. J., Anderson, J., Vaishnav, Y., Solomon, B., Adair, C. F., Saji, M., Burman, K. D., Burch, H. B., and Ringel, M. D. 2002. Determination of galectin-3 messenger ribonucleic Acid overexpression in papillary thyroid cancer by quantitative reverse transcription-polymerase chain reaction. *J Clin Endocrinol Metab.* 87:4792-4796.
9. Kroll, T. G., Sarraf, P., Pecciarini, L., Chen, C. J., Mueller, E., Spiegelman, B. M., and Fletcher, J. A. 2000. PAX8-PPARgamma1 fusion oncogene in human thyroid carcinoma [corrected]. *Science.* 289:1357-1360.
10. Marques, A. R., Espadinha, C., Catarino, A. L., Moniz, S., Pereira, T., Sobrinho, L. G., and Leite, V. 2002. Expression of PAX8-PPAR gamma 1 rearrangements in both follicular thyroid carcinomas and adenomas. *J Clin Endocrinol Metab.* 87:3947-3952.
11. Nikiforova, M. N., Biddinger, P. W., Caudill, C. M., Kroll, T. G., and Nikiforov, Y. E. 2002. PAX8-PPARgamma rearrangement in thyroid tumors: RT-PCR and immunohistochemical analyses. *Am J Surg Pathol.* 26:1016-1023.
12. Cheung, L., Messina, M., Gill, A., Clarkson, A., Learoyd, D., Delbridge, L., Wentworth, J., Philips, J., Clifton-Bligh, R., and Robinson, B. G. 2003. Detection of the PAX8-

PPAR gamma fusion oncogene in both follicular thyroid carcinomas and adenomas. *J Clin Endocrinol Metab.* 88:354-357.

13. Fagin, J. A. 1995. Tumor suppressor genes in human thyroid neoplasms: p 53 mutations are associated undifferentiated thyroid cancers. *J Endocrinol Invest.* 18:140-142.

14. Haugen, B. R., Nawaz, S., Markham, N., Hashizumi, T., Shroyer, A. L., Werness, B., and Shroyer, K. R. 1997. Telomerase activity in benign and malignant thyroid tumors. *Thyroid.* 7:337-342.

15. Sack, M. J., Astengo-Osuna, C., Lin, B. T., Battifora, H., and LiVolsi, V. A. 1997. HBME-1 immunostaining in thyroid fine-needle aspirations: a useful marker in the diagnosis of carcino ma. *Mod Pathol.* 10:668-674.

16. Barden, C. B., Shister, K. W., Zhu, B., Guiter, G., Greenblatt, D. Y., Zeiger, M. A., and Fahey, T. J., 3rd. 2003. Classification of follicular thyroid tumors by molecular signature: results of gene profiling. *Clin Cancer Res.* 9:1792-1800.

17. Velculescu, V. E., Zhang, L., Vogelstein, B., and Kinzler, K. W. 1995. Serial analysis of gene expression. *Science.* 270:484-487.

18. Pang, X. P., Hershman, J. M., Chung, M., and Pekary, A. E. 1989. Characterization of tumor necrosis factor-alpha receptors in human and rat thyroid cells and regulation of the receptors by thyrotropin. *Endocrinology.* 125:1783-1788.

19. St Croix, B., et al. 2000. Genes expressed in human tumor endothelium. *Science.* 289:1197-1202.

20. Lal, A., et al. 1999. A public database for gene expression in human cancers. *Cancer Res.* 59:5403-5407.

21. Boon, K., et al. 2002. An anatomy of normal and malignant gene expression. *Proc Natl Acad Sci USA.* 99:11287-11292.

22. Buckhaults, P., Rago, C., St Croix, B., Romans, K. E., Saha, S., Zhang, L., Vogelstein, B., and Kinzler, K. W. 2001. Secreted and cell surface genes expressed in benign and malignant colorectal tumors. *Cancer Res.* 61:6996-7001.

23. Radmacher, M. D., McShane, L. M., and Simon, R. 2002. A paradigm for class prediction using gene expression profiles. *J Comput Biol.* 9:505-511.

24. Tukey, J. W. 1993. Tightening the clinical trial. *Control Clin Trials.* 14:266-285.

25. Simon, R., Radmacher, M. D., Dobbin, K., and McShane, L. M. 2003. Pitfalls in the use of DNA microarray data for diagnostic and prognostic classification. *J Nat Cancer Inst.* 95:14-18.

26. Zhang, L., Zhou, W., Velculescu, V. E., Kern, S. E., Hruban, R. H., Hamilton, S. R., Vogelstein, B., and Kinzler, K. W. 1997. Gene expression profiles in normal and cancer cells. *Science.* 276:1268-1272.

27. Cerutti, J., Trapasso, F., Battaglia, C., Zhang, L., Martelli, M. L., Visconti, R., Berlingieri, M. T., Fagin, J. A., Santoro, M., and Fusco, A. 1996. Block of c-myc expression by antisense oligonucleotides inhibits proliferation of human thyroid carcinoma cell lines. *Clin Cancer Res.* 2:119-126.

28. Visconti, R., et al. 1997. Expression of the neoplastic phenotype by human thyroid carcinoma cell lines requires NFκB p 65 protein expression. *Oncogene.* 15:1987-1994.

29. Pauws, E., Moreno, J. C., Tijssen, M., Baas, F., de Vijlder, J. J., and Ris-Stalpers, C. 2000. Serial analysis of gene expression as a tool to assess the human thyroid expression profile and to identify novel thyroidal genes. *J Clin Endocrinol Metab.* 85:1923-1927.

30. Takano, T., Hasegawa, Y., Matsuzuka, F., Miyauchi, A., Yoshida, H., Higashiyama, T., Kuma, K., and Amino, N. 2000. Gene expression profiles in thyroid carcinomas. *Br J Cancer.* 83:1495-1502.

31. Pauws, E., van Kampen, A. H., van de Graaf, S. A., de Vijlder, J. J., and Ris-Stalpers, C. 2001. Heterogeneity in polyadenylation cleavage sites in mammalian mRNA sequences: implications for SAGE analysis. *Nucleic Acids Res.* 29:1690-1694.

32. Nozaki, S., Sledge Jr, G. W., and Nakshatri, H. 2001. Repression of GADD153/CHOP by NF-κB: a possible cellular defense against endoplasmic reticulum stress-induced cell death. *Oncogene.* 20:2178-2185.

33. Jin, K., Mao, X. O., Eshoo, M. W., del Rio, G., Rao, R., Chen, D., Simon, R. P., and Greenberg, D. A. 2002. cDN A microarray analysis of changes in gene expression induced by neuronal hypoxia in vitro. *Neurochem Res.* 27:1105-1112.

34. Talukder, A. H., Wang, R. A., and Kumar, R. 2002. Expression and transactivating functions of the bZIP transcription factor GADD153 in mammary epithelial cells. *Oncogene.* 21:4289-4300.

35. Nikiforova, M. N., Lynch, R. A., Biddinger, P. W., Alexander, E. K., Dorn, G. W., 2nd, Tallini, G., Kroll, T. G., and Nikiforov, Y. E. 2003. RAS point mutations and PAX8-PPARgamma rearrangement in thyroid tumors: evidence for distinct molecular pathways in thyroid follicular carcinoma. *J Clin Endocrinol Metab.* 88:2318-2326.

36. Brenner, B., Koppenhoefer, U., Weinstock, C., Linderkamp, O., Lang, F., and Gulbins, E. 1997. Fas- or ceramide-induced apoptosis is mediated by a Rac1-regulated activation of Jun N-terminal kinase/p38 kinases and GADD153. *J Biol Chem.* 272:22173-22181.

37. Satoh, T., Toyoda, M., Hoshino, H., Monden, T., Yamada, M., Shimizu, H., Miyamoto, K., and Mori, M. 2002. Activation of peroxisome proliferatoractivated receptor-gamma stimulates the growth arrest and DNA-damage inducible 153 gene in non-small cell lung carcinoma cells. *Oncogene.* 21:2171-2180.

38. Gotoh, T., Araki, M., and Mori, M. 1997. Chromosomal localization of the human arginase II gene and tissue distribution of its mRNA. *Biochem Biophys Res Commun.* 233:487-491.

39. Morris, S. M., Jr., Bhamidipati, D., and Kepka-Lenhart, D. 1997. Human type II arginase: sequence analysis and tissue-specific expression. *Gene.* 193:157-161.

40. Russell, D. H., and McVicker, T. A. 1972. Polyamine biogenesis in the rat mammary gland during pregnancy and lactation. *Biochem J.* 130:71-76.

41. Tian, W., Boss, G. R., and Cohen, D. M. 2000. Ras signaling in the inner medullary cell response to urea and NaCl. *Am J Physiol Cell Physiol.* 278:C372-380.

42. Hong, G., Deleersnijder, W., Kozak, C. A., Van Marck, E., Tylzanowski, P., and Merregaert, J. 1996. Molecular cloning of a highly conserved mouse and human integral membrane protein (Itm1) and genetic mapping to mouse chromosome 9. *Genomics.* 31:295-300.

43. Van Hul, W., Hong, G., Wauters, J., Van Hul, E., Nowak, N., Shows, T. B., Willems, P. J., and Merregaert, J. 1996. Assignment of the human integral transmembrane protein 1 gene (ITM1) to human chromosome band 11q23.3 by in situ hybridization and YAC mapping. *Cytogenet Cell Genet.* 74:218-219.

44. Meerabux, J. M., Cotter, F. E., Kearney, L., Nizetic, D., Dhut, S., Gibbons, B., Lister, T. A., and Young, B. D. 1994. Molecular cloning of a novel 11q23 breakpoint associated with non-Hodgkin's lymphoma. *Oncogene.* 9:893-898.

45. Matsuo, K., Tang, S. H., and Fagin, J. A. 1991. Allelotype of human thyroid tumors: loss of chromosome 11q13 sequences in follicular neoplasms. *Mol Endocrinol.* 5:1873-1879.
46. Ward, L. S., Brenta, G., Medvedovic, M., and Fagin, J. A. 1998. Studies of allelic loss in thyroid tumors reveal major differences in chromosomal instability between papillary and follicular carcinomas. *J Clin Endocrinol Metab.* 83:525-530.
47. Sood, R., et al. 2001. Cloning and characterization of 13 novel transcripts and the human RGS8 gene from the 1q25 region encompassing the hereditary prostate cancer (HPC1) locus. *Genomics.* 73:211-222.
48. Matsuda, S., Iriyama, C., Yokozaki, S., Ichigotani, Y., Shirafuji, N., Yamaki, K., Hayakawa, T., and Hamaguchi, M. 2001. Cloning and sequencing of a novel human gene that encodes a putative target protein of Nesh-SH3. *J Hum Genet.* 46:483-486.
49. Ichigotani, Y., Yokozaki, S., Fukuda, Y., Hamaguchi, M., and Matsuda, S. 2002. Forced expression of NESH suppresses motility and metastatic dissemination of malignant cells. Cancer Res. 62:2215-2219.
50. Zedenius, J., Wallin, G., Svensson, A., Grimelius, L., Hoog, A., Lundell, G., Backdahl, M., and Larsson, C. 1995. Allelotyping of follicular thyroid tumors. *Hum Genet.* 96:27-32.
51. Roque, L., Rodrigues, R., Pinto, A., Moura-Nunes, V., and Soares, J. 2003. Chromosome imbalances in thyroid follicular neoplasms: a comparison between follicular adenomas and carcinomas. *Genes Chromosomes Cancer.* 36:292-302.
52. Grebe, S. K., McIver, B., Hay, I. D., Wu, P. S., Maciel, L. M., Drabkin, H. A., Goellner, J. R., Grant, C. S., Jenkins, R. B., and Eberhardt, N. L. 1997. Frequent loss of heterozygosity on chromosomes 3p and 17p without VHL or p53 mutations suggests involvement of unidentified tumor suppressor genes in follicular thyroid carcinoma. *J Clin Endocrinol Metab.* 82:3684-3691.
53. Di Renzo, M. F., et al. 1995. Overexpression of the c-MET/HGF receptor in human thyroid carcinomas derived from the follicular epithelium. *J Endocrinol Invest.* 18:134-139.
54. Ippolito, A., Vella, V., La Rosa, G. L., Pellegriti, G., Vigneri, R., and Belfiore, A. 2001. Immunostaining for Met/HGF receptor may be useful to identify malignancies in thyroid lesions classified suspicious at fine-needle aspiration biopsy. *Thyroid.* 11:783-787.
55. Hanson, E. S., and Leibold, E. A. 1998. Regulation of iron regulatory protein 1 during hypoxia and hypoxia/reoxygenation. *J Biol Chem.* 273:7588-7593.
56. Lal, A., Peters, H., St Croix, B., Haroon, Z. A., Dewhirst, M. W., Strausberg, R. L., Kaanders, J. H., van der Kogel, A. J., and Riggins, G. J. 2001. Transcriptional response to hypoxia in human tumors. *J Natl Cancer Inst.* 93:1337-1343.
57. Chia, S. K., Wykoff, C. C., Watson, P. H., Han, C., Leek, R. D., Pastorek, J., Gatter, K. C., Ratcliffe, P., and Harris, A. L. 2001. Prognostic significance of a novel hypoxia-regulated marker, carbonic anhydrase IX, in invasive breast carcinoma. *J Clin Oncol.* 19:3660-3668.
58. Fonseca, E., Soares, P., Rossi, S., and Sobrinho-Simoes, M. 1997. Prognostic factors in thyroid carcinomas. *Verh Dtsch Ges Pathol.* 81:82-96.

---

The invention claimed is:

1. A method for distinguishing follicular thyroid adenoma (FTA) from follicular thyroid carcinoma (FTC) comprising the steps of:
determining amount of an expression product of at least one gene selected from the group consisting of DDIT3, ARG2, ITM1, C1orf24, TARSH, and ACO1 in a test follicular thyroid specimen;
comparing the amount in the test specimen to the amount in a normal control thyroid specimen, wherein the expression product is selected from the group consisting of protein and RNA;
identifying the test follicular thyroid specimen as FTA if the amount of expression product of TARSH is equal to or greater in the test follicular thyroid specimen than in the normal control thyroid specimen, or identifying the test follicular thyroid specimen as FTC if the amount of expression product of DDIT3, ARG2, ITM1, C1orf24, or ACO1 is greater in the test follicular thyroid specimen than in the normal control thyroid specimen.

2. The method of claim 1 wherein the at least one gene comprises DDIT3.

3. The method of claim 1 wherein the at least one gene comprises ARG2.

4. The method of claim 1 wherein the at least one gene comprises ITM1.

5. The method of claim 1 wherein the at least one gene comprises C1orf24.

6. The method of claim 1 wherein the at least one gene comprises TARSH.

7. The method of claim 1 wherein the at least one gene comprises ACO1.

8. The method of claim 1 wherein the test follicular thyroid specimen is a fine-needle aspiration biopsy.

9. The method of claim 1 wherein the test follicular thyroid specimen is a pre-operative specimen.

10. The method of claim 1 wherein the amount of RNA is compared.

11. The method of claim 10 wherein the amount of RNA is determined by reverse transcriptase-polymerase chain reaction (RT-PCR).

12. The method of claim 1 wherein the amount of protein is compared.

13. The method of claim 12 wherein the amount of protein is determined using an antibody.

14. The method of claim 13 wherein the antibody is contacted with a histological preparation of the test follicular thyroid specimen.

15. The method of claim 1 wherein the follicular thyroid specimen is identified as FTC if the amount of at least two of said expression products of DDIT3, ARG2, ITM1, C1orf24, and ACO1 is greater in the test follicular thyroid specimen than in the normal control thyroid specimen.

16. The method of claim 1 wherein the follicular thyroid specimen is identified as FTC if the amount of at least three of said expression products of DDIT3, ARG2, ITM1, C1orf24, and ACO1 is greater in the test follicular thyroid specimen than in the normal control thyroid specimen.

17. The method of claim 1 wherein the follicular thyroid specimen is identified as FTC if the amount of at least four of said expression products of DDIT3, ARG2, ITM1, C1orf24, and ACO1 is greater in the test follicular thyroid specimen than in the normal control thyroid specimen.

18. The method of claim 1 wherein the follicular thyroid specimen is identified as FTC if the amount of at least five of said expression products of DDIT3, ARG2, ITM1, C1orf24, and ACO1 is greater in the test follicular thyroid specimen than in the normal control thyroid specimen.

19. The method of claim 1 wherein the step of determining employs a technique selected from the group consisting of: microarray analysis, northern blot analysis, differential hybridization, ribonuclease protection, enzyme-linked immunosorbent assay (ELISA), immunoprecipitation, western blot, radioimmunoassay, and fluorescence activated cell sorting.

20. The method of claim 1 further comprising the step of aspirating using a fine needle to form the test follicular thyroid specimen.

21. The method of claim 1 further comprising the step of obtaining a test follicular thyroid specimen prior to surgery.

22. A method for distinguishing follicular thyroid adenoma (FTA) from follicular thyroid carcinoma (FTC) comprising the steps of:
determining amount of an expression product of DDIT3, ARG2, and ITM1 in a test follicular thyroid specimen;
comparing the amount in the test sample to the amount in a normal control thyroid specimen wherein the expression product is selected from the group consisting of protein and RNA;
identifying the test follicular thyroid specimen as FTC if the amount of expression product of DDIT3, ARG2, or ITM1 is increased in the test follicular thyroid specimen relative to the normal control thyroid specimen.

23. The method of claim 22 wherein the test follicular thyroid specimen is a fine-needle aspiration biopsy.

24. The method of claim 22 wherein the test follicular thyroid specimen is a pre-operative specimen.

25. The method of claim 22 wherein the amount of RNA is compared.

26. The method of claim 25 wherein the amount of RNA is determined by reverse transcriptase-polymerase chain reaction (RT-PCR).

27. The method of claim 22 wherein the amount of protein is compared.

28. The method of claim 27 wherein the amount of protein is determined using an antibody.

29. The method of claim 28 wherein the antibody is contacted with a histological preparation of the test follicular thyroid specimen.

30. The method of claim 22 wherein the follicular thyroid specimen is identified as FTC if DDIT3 and ARG2 are increased.

31. The method of claim 22 wherein the follicular thyroid specimen is identified as FTC if DDIT3 and ITM1 are increased.

32. The method of claim 22 wherein the follicular thyroid specimen is identified as FTC if ITM1 and ARG2 are increased.

33. The method of claim 22 wherein the follicular thyroid specimen is identified as FTC if DDIT3, ARG2, and ITM1 are increased.

34. The method of claim 22 wherein the step of determining employs a technique selected from the group consisting of: microarray analysis, northern blot analysis, differential hybridization, ribonuclease protection, enzyme-linked immunosorbent assay (ELISA), immunoprecipitation, western blot, radioimmunoassay, and fluorescence activated cell sorting.

35. The method of claim 22 further comprising the step of aspirating using a fine needle to form the test follicular thyroid specimen.

36. The method of claim 22 further comprising the step of obtaining a test follicular thyroid specimen prior to surgery.

* * * * *

SEQUENCE LISTING

```
<160> NUMBER OF SEQ ID NOS: 98

<210> SEQ ID NO 1
<211> LENGTH: 510
<212> TYPE: DNA
<213> ORGANISM: human

<400> SEQUENCE: 1
atggcagctg agtcattgcc tttctccttt gggacactgt ccagctggga gctggaagcc      60
tggtatgagg acctgcaaga ggtcctgtct tcagatgaaa atgggggtac ctatgtttca     120
cctcctggaa atgaagagga agaatcaaaa atcttcacca ctcttgaccc tgcttctctg     180
gcttggctga ctgaggagga gccagaacca gcagaggtca caagcacctc ccagagccct     240
cactctccag attccagtca gagctccctg gctcaggagg aagaggagga agaccaaggg     300
agaaccagga aacggaaaca gagtggtcat tccccagccc gggctggaaa gcagcgcatg     360
aaggagaaag aacaggagaa tgaaaggaaa gtggcacagc tagctgaaga gaatgaacgg     420
ctcaagcagg aaatcgagcg cctgaccagg gaagtagagg cgactcgccg agctctgatt     480
gaccgaatgg tgaatctgca ccaagcatga                                      510

<210> SEQ ID NO 2
<211> LENGTH: 169
<212> TYPE: PRT
<213> ORGANISM: human

<400> SEQUENCE: 2

Met Ala Ala Glu Ser Leu Pro Phe Ser Phe Gly Thr Leu Ser Ser Trp
```

```
1               5                  10                 15
Glu Leu Glu Ala Trp Tyr Glu Asp Leu Gln Glu Val Leu Ser Ser Asp
                20                 25                 30

Glu Asn Gly Gly Thr Tyr Val Ser Pro Pro Gly Asn Glu Glu Glu Glu
                35                 40                 45

Ser Lys Ile Phe Thr Thr Leu Asp Pro Ala Ser Leu Ala Trp Leu Thr
 50                 55                 60

Glu Glu Glu Pro Glu Pro Ala Glu Val Thr Ser Thr Ser Gln Ser Pro
 65                 70                 75                 80

His Ser Pro Asp Ser Ser Gln Ser Ser Leu Ala Gln Glu Glu Glu Glu
                85                 90                 95

Glu Asp Gln Gly Arg Thr Arg Lys Arg Lys Gln Ser Gly His Ser Pro
                100                105                110

Ala Arg Ala Gly Lys Gln Arg Met Lys Glu Lys Glu Gln Glu Asn Glu
                115                120                125

Arg Lys Val Ala Gln Leu Ala Glu Glu Asn Glu Arg Leu Lys Gln Glu
                130                135                140

Ile Glu Arg Leu Thr Arg Glu Val Glu Ala Thr Arg Arg Ala Leu Ile
145                 150                155                160

Asp Arg Met Val Asn Leu His Gln Ala
                165

<210> SEQ ID NO 3
<211> LENGTH: 1065
<212> TYPE: DNA
<213> ORGANISM: human

<400> SEQUENCE: 3
atgtccctaa ggggcagcct ctcgcgtctc ctccagacgc gagtgcattc catcctgaag      60
aaatccgtcc actccgtggc tgtgatagga gccccgttct cacaagggca gaaaagaaaa     120
ggagtggagc atggtcccgc tgccataaga gaagctggct gatgaaaag gctctccagt     180
ttgggctgcc acctaaaaga ctttggagat tgagttttta ctccagtccc caagatgat     240
ctctacaaca acctgatagt gaatccacgc tcagtgggtc ttgccaacca ggaactggct     300
gaggtggtta gcagagctgt gtcagatggc tacagctgtg tcacactggg aggagaccac     360
agcctggcaa tcggtaccat tagtggccat gcccgacact gcccagacct tgtgttgtc     420
tgggttgatg cccatgctga catcaacaca ccccttacca cttcatcagg aaatctccat     480
ggacagccag tttcatttct cctcagagaa ctacaggata aggtaccaca actcccagga     540
ttttcctgga tcaaaccttg tatctcttct gcaagtattg tgtatattgg tctgagagac     600
gtggaccctc ctgaacattt tatttaaag aactatgata tccagtattt ttccatgaga     660
gatattgatc gacttggtat ccagaaggtc atggaacgaa catttgatct gctgattggc     720
aagagacaaa gaccaatcca tttgagtttt gatattgatg catttgaccc tacactggct     780
ccagccacag gaactcctgt tgtcggggga ctaacctatc gagaaggcat gtatattgct     840
gaggaaatac acaataccgg gttgctatca gcactggatc ttgttgaagt caatcctcag     900
ttggccacct cagaggaaga ggcgaagact acagctaacc tggcagtaga tgtgattgct     960
tcaagctttg gtcagacaag agaaggaggg catattgtct atgaccaact tcctactccc    1020
agttcaccag atgaatcaga aaatcaagca cgtgtgagaa tttag                    1065

<210> SEQ ID NO 4
<211> LENGTH: 354
<212> TYPE: PRT
```

<213> ORGANISM: human

<400> SEQUENCE: 4

```
Met Ser Leu Arg Gly Ser Leu Ser Arg Leu Leu Gln Thr Arg Val His
1               5                   10                  15

Ser Ile Leu Lys Lys Ser Val His Ser Val Ala Val Ile Gly Ala Pro
            20                  25                  30

Phe Ser Gln Gly Gln Lys Arg Lys Gly Val Glu His Gly Pro Ala Ala
        35                  40                  45

Ile Arg Glu Ala Gly Leu Met Lys Arg Leu Ser Ser Leu Gly Cys His
    50                  55                  60

Leu Lys Asp Phe Gly Asp Leu Ser Phe Thr Pro Val Pro Lys Asp Asp
65                  70                  75                  80

Leu Tyr Asn Asn Leu Ile Val Asn Pro Arg Ser Val Gly Leu Ala Asn
                85                  90                  95

Gln Glu Leu Ala Glu Val Val Ser Arg Ala Val Ser Asp Gly Tyr Ser
            100                 105                 110

Cys Val Thr Leu Gly Gly Asp His Ser Leu Ala Ile Gly Thr Ile Ser
        115                 120                 125

Gly His Ala Arg His Cys Pro Asp Leu Cys Val Val Trp Val Asp Ala
    130                 135                 140

His Ala Asp Ile Asn Thr Pro Leu Thr Thr Ser Ser Gly Asn Leu His
145                 150                 155                 160

Gly Gln Pro Val Ser Phe Leu Leu Arg Glu Leu Gln Asp Lys Val Pro
                165                 170                 175

Gln Leu Pro Gly Phe Ser Trp Ile Lys Pro Cys Ile Ser Ser Ala Ser
            180                 185                 190

Ile Val Tyr Ile Gly Leu Arg Asp Val Asp Pro Pro Glu His Phe Ile
        195                 200                 205

Leu Lys Asn Tyr Asp Ile Gln Tyr Phe Ser Met Arg Asp Ile Asp Arg
    210                 215                 220

Leu Gly Ile Gln Lys Val Met Glu Arg Thr Phe Asp Leu Leu Ile Gly
225                 230                 235                 240

Lys Arg Gln Arg Pro Ile His Leu Ser Phe Asp Ile Asp Ala Phe Asp
                245                 250                 255

Pro Thr Leu Ala Pro Ala Thr Gly Thr Pro Val Val Gly Gly Leu Thr
            260                 265                 270

Tyr Arg Glu Gly Met Tyr Ile Ala Glu Glu Ile His Asn Thr Gly Leu
        275                 280                 285

Leu Ser Ala Leu Asp Leu Val Glu Val Asn Pro Gln Leu Ala Thr Ser
    290                 295                 300

Glu Glu Glu Ala Lys Thr Thr Ala Asn Leu Ala Val Asp Val Ile Ala
305                 310                 315                 320

Ser Ser Phe Gly Gln Thr Arg Glu Gly Gly His Ile Val Tyr Asp Gln
                325                 330                 335

Leu Pro Thr Pro Ser Ser Pro Asp Glu Ser Glu Asn Gln Ala Arg Val
            340                 345                 350

Arg Ile
```

<210> SEQ ID NO 5
<211> LENGTH: 2094
<212> TYPE: DNA
<213> ORGANISM: human

<400> SEQUENCE: 5

```
atgtgtaaat cactgcgtta ttgctttagt cattgtctct atttagcaat gacaagactg    60
gaagaagtaa atagagaagt gaacatgcat tcttcagtgc ggtatcttgg ctatttagcc   120
agaatcaatt tattggttgc tatatgctta ggtctatacg taagatggga aaaaacagca   180
aattccttaa ttttggtaat ttttattctt ggtcttttg ttcttggaat cgccagcata   240
ctctattact attttcaat ggaagcagca agtttaagtc tctccaatct ttggtttgga   300
ttcttgcttg gcctcctatg ttttcttgat aattcatcct ttaaaaatga tgtaaaagaa   360
gaatcaacca atatttgct tctaacatcc atagtgttaa ggatattgtg ctctctggtg   420
gagagaattt ctggctatgt ccgtcatcgg cccactttac taaccacagt tgaatttctg   480
gagcttgttg gatttgccat tgccagcaca actatgttgg tggagaagtc tctgagtgtc   540
attttgcttg ttgtagctct ggctatgctg attattgatc tgagaatgaa atctttctta   600
gctattccaa acttagttat ttttgcagtt ttgttatttt tttcctcatt ggaaactccc   660
aaaaatccga ttgcttttgc gtgtttttttt atttgcctga taactgatcc tttccttgac   720
atttatttta gtggactttc agtaactgaa agatggaaac ccttttttgta ccgtggaaga   780 atttgcagaa gactttcagt cgttttttgct ggaatgattg agcttacatt tttattctt   840 tccgcattca aacttagaga cactcacctc tggtattttg taatacctgg cttttccatt   900
tttgaatttt tcaggatgat ttgtcatatt attttctttt taactctttg gggattccat   960
accaaattaa atgactgcca taaagtatat tttactcaca ggacagatta caatagcctt  1020
gatagaatca tggcatccaa agggatgcgc cattttttgct tgatttcaga gcagttggtg  1080
ttctttagtc ttcttgcaac agcgatttg ggagcagttt cctggcagcc aacaaatgga  1140
attttcttga gcatgttcct aatcgttttg ccattggaat ccatggctca tgggctcttc  1200
catgaattgg gtaactgttt aggaggaaca tctgttggat atgctattgt gattcccacc  1260
aacttctgca gtcctgatgg tcagccaaca ctgcttcccc cagaacatgt acaggagtta  1320
aatttgaggt ctactggcat gctcaatgct atccaaagat ttttttgcata tcatatgatt  1380 gagacctatg gatgtgacta ttccacaagt ggactgtcat tgatactct gcattccaaa  1440 ctaaaagctt cctcgaact tcggacagtg atgggaccca gacatgatac gtatatttttg  1500 tattacagtg ggcacaccca tggtacagga gagtgggctc tagcaggtgg agatacacta  1560
cgccttgaca cacttataga atggtggaga gaaaagaatg gttcctttttg ttcccggctt  1620 attatcgtat tagacagcga aaattcaacc ccttgggtga agaagtgag gaaaattaat  1680 gaccagtata ttgcagtgca aggagcagag ttgataaaaa cagtagatat tgaagaagct  1740
gacccgccac agctaggtga ctttacaaaa gactgggtag aatataactg caactcctgt  1800
aataacatct gctggactga aaagggacgc acagtgaaag cagtatatgg tgtgtcaaaa  1860
cggtggagtg actacactct gcatttgcca acgggaagcg atgtggccaa gcactggatg  1920
ttacactttc ctcgtattac atatcccta gtgcatttgg caaattggtt atgcggtctg  1980 aaccttttttt ggatctgcaa aacttgttttt aggtgcttga aaagattaaa aatgagttgg  2040
tttcttccta ctgtgctgga cacaggacaa ggcttcaaac ttgtcaaatc ttaa        2094
```

<210> SEQ ID NO 6
<211> LENGTH: 697
<212> TYPE: PRT
<213> ORGANISM: human

<400> SEQUENCE: 6

```
Met Cys Lys Ser Leu Arg Tyr Cys Phe Ser His Cys Leu Tyr Leu Ala
1               5                   10                  15
```

```
Met Thr Arg Leu Glu Glu Val Asn Arg Glu Val Asn Met His Ser Ser
            20                  25                  30
Val Arg Tyr Leu Gly Tyr Leu Ala Arg Ile Asn Leu Leu Val Ala Ile
            35                  40                  45
Cys Leu Gly Leu Tyr Val Arg Trp Glu Lys Thr Ala Asn Ser Leu Ile
 50                  55                  60
Leu Val Ile Phe Ile Leu Gly Leu Phe Val Leu Gly Ile Ala Ser Ile
 65                  70                  75                  80
Leu Tyr Tyr Tyr Phe Ser Met Glu Ala Ala Ser Leu Ser Leu Ser Asn
                 85                  90                  95
Leu Trp Phe Gly Phe Leu Leu Gly Leu Leu Cys Phe Leu Asp Asn Ser
            100                 105                 110
Ser Phe Lys Asn Asp Val Lys Glu Glu Ser Thr Lys Tyr Leu Leu Leu
            115                 120                 125
Thr Ser Ile Val Leu Arg Ile Leu Cys Ser Leu Val Glu Arg Ile Ser
130                 135                 140
Gly Tyr Val Arg His Arg Pro Thr Leu Leu Thr Thr Val Glu Phe Leu
145                 150                 155                 160
Glu Leu Val Gly Phe Ala Ile Ala Ser Thr Thr Met Leu Val Glu Lys
                165                 170                 175
Ser Leu Ser Val Ile Leu Leu Val Val Ala Leu Ala Met Leu Ile Ile
            180                 185                 190
Asp Leu Arg Met Lys Ser Phe Leu Ala Ile Pro Asn Leu Val Ile Phe
            195                 200                 205
Ala Val Leu Leu Phe Phe Ser Ser Leu Glu Thr Pro Lys Asn Pro Ile
210                 215                 220
Ala Phe Ala Cys Phe Phe Ile Cys Leu Ile Thr Asp Pro Phe Leu Asp
225                 230                 235                 240
Ile Tyr Phe Ser Gly Leu Ser Val Thr Glu Arg Trp Lys Pro Phe Leu
                245                 250                 255
Tyr Arg Gly Arg Ile Cys Arg Arg Leu Ser Val Val Phe Ala Gly Met
            260                 265                 270
Ile Glu Leu Thr Phe Phe Ile Leu Ser Ala Phe Lys Leu Arg Asp Thr
            275                 280                 285
His Leu Trp Tyr Phe Val Ile Pro Gly Phe Ser Ile Phe Gly Ile Phe
290                 295                 300
Arg Met Ile Cys His Ile Ile Phe Leu Leu Thr Leu Trp Gly Phe His
305                 310                 315                 320
Thr Lys Leu Asn Asp Cys His Lys Val Tyr Phe Thr His Arg Thr Asp
                325                 330                 335
Tyr Asn Ser Leu Asp Arg Ile Met Ala Ser Lys Gly Met Arg His Phe
            340                 345                 350
Cys Leu Ile Ser Glu Gln Leu Val Phe Phe Ser Leu Leu Ala Thr Ala
            355                 360                 365
Ile Leu Gly Ala Val Ser Trp Gln Pro Thr Asn Gly Ile Phe Leu Ser
            370                 375                 380
Met Phe Leu Ile Val Leu Pro Leu Glu Ser Met Ala His Gly Leu Phe
385                 390                 395                 400
His Glu Leu Gly Asn Cys Leu Gly Gly Thr Ser Val Gly Tyr Ala Ile
                405                 410                 415
Val Ile Pro Thr Asn Phe Cys Ser Pro Asp Gly Gln Pro Thr Leu Leu
            420                 425                 430
Pro Pro Glu His Val Gln Glu Leu Asn Leu Arg Ser Thr Gly Met Leu
```

```
                435                 440                 445
Asn Ala Ile Gln Arg Phe Phe Ala Tyr His Met Ile Glu Thr Tyr Gly
    450                 455                 460

Cys Asp Tyr Ser Thr Ser Gly Leu Ser Phe Asp Thr Leu His Ser Lys
465                 470                 475                 480

Leu Lys Ala Phe Leu Glu Leu Arg Thr Val Asp Gly Pro Arg His Asp
                485                 490                 495

Thr Tyr Ile Leu Tyr Tyr Ser Gly His Thr His Gly Thr Gly Glu Trp
            500                 505                 510

Ala Leu Ala Gly Gly Asp Thr Leu Arg Leu Asp Thr Leu Ile Glu Trp
        515                 520                 525

Trp Arg Glu Lys Asn Gly Ser Phe Cys Ser Arg Leu Ile Ile Val Leu
    530                 535                 540

Asp Ser Glu Asn Ser Thr Pro Trp Val Lys Glu Val Arg Lys Ile Asn
545                 550                 555                 560

Asp Gln Tyr Ile Ala Val Gln Gly Ala Glu Leu Ile Lys Thr Val Asp
                565                 570                 575

Ile Glu Glu Ala Asp Pro Pro Gln Leu Gly Asp Phe Thr Lys Asp Trp
            580                 585                 590

Val Glu Tyr Asn Cys Asn Ser Cys Asn Asn Ile Cys Trp Thr Glu Lys
        595                 600                 605

Gly Arg Thr Val Lys Ala Val Tyr Gly Val Ser Lys Arg Trp Ser Asp
    610                 615                 620

Tyr Thr Leu His Leu Pro Thr Gly Ser Asp Val Ala Lys His Trp Met
625                 630                 635                 640

Leu His Phe Pro Arg Ile Thr Tyr Pro Leu Val His Leu Ala Asn Trp
                645                 650                 655

Leu Cys Gly Leu Asn Leu Phe Trp Ile Cys Lys Thr Cys Phe Arg Cys
            660                 665                 670

Leu Lys Arg Leu Lys Met Ser Trp Phe Leu Pro Thr Val Leu Asp Thr
        675                 680                 685

Gly Gln Gly Phe Lys Leu Val Lys Ser
    690                 695

<210> SEQ ID NO 7
<211> LENGTH: 2787
<212> TYPE: DNA
<213> ORGANISM: human

<400> SEQUENCE: 7
atgggcggct cagcctccag ccagctggac gagggcaagt gcgcttacat ccgagggaaa      60
actgaggctg ccatcaaaaa cttcagtccc tactacagtc gtcagtactc tgtggctttc     120
tgcaatcacg tgcgcactga agtagaacag caaagagatt taacgtcaca gttttttgaag    180 accaagccac cattggcgcc tggaactatt ttgtatgaag cagagctatc acaattttct     240
gaagacataa agaagtggaa ggagagatac gttgtagtta aaatgattaa tgctgtggag     300
agctatgaga taaagaggc ctatcagaga ggagctgctc ctaaatgtcg aattcttcca      360
gccggtggca aggtgttaac ctcagaagat gaatataatc tgttgtctga caggcatttc     420
ccagaccctc ttgcctccag tgagaaggag aacactcagc cctttgtggt cctgcccaag     480
gaattcccag tgtacctgtg cagcccttc ttcagacacg ctacttctg cttccacgag      540 gctgctgacc agaagaggtt tagtgccctc tgagtgact cgtcaggca tctcaatcat      600 gattacatga agcagatgac atttgaagcc caagcctttt tagaagctgt gcaattcttc     660
```

| | |
|---|---|
| cgacaggaga agggtcacta tggttcctgg gaaatgatca ctggggatga aatccagatc | 720 |
| ctgagtaacc tggtgatgga ggagctcctg cccactcttc agacagacct gctgcctaag | 780 |
| atgaagggga agaagaatga cagaaagagg acgtggcttg gtctcctcga ggaggcctac | 840 |
| accctggttc agcatcaagt ttcagaagga ttaagtgcct tgaaggagga atgcagagct | 900 |
| ctgacaaagg gcctggaagg aacgatccgt tctgacatgg atcagattgt gaactcaaag | 960 |
| aactatttaa ttggaaagat caaagcgatg gtggcccagc cggcgagaa aagctgcttg | 1020 |
| gagagtgtgc agccattcct ggcatccatc ctggaggagc tcatgggacc agtgagctcg | 1080 |
| ggattcagtg aagtacgtgt actctttgag aaagaggtga atgaagtcag ccagaacttc | 1140 |
| cagaccacca agacagtgt ccagctaaag gagcatctag accggcttat gaatcttccg | 1200 |
| ctgcattccg tgaagatgga accttgttat actaaagtca acctgcttca cgagcgcctg | 1260 |
| caggatctca agagccgctt cagattcccc cacattgatc tggtggttca gaggacacag | 1320 |
| aactacatgc aggagctaat ggagaatgca gtgttcactt ttgagcagtt gctttcccca | 1380 |
| catctccaag gagaggcctc caaaactgca gttgccattg agaaggttaa actccgagtc | 1440 |
| ttaaagcaat atgattatga cagcagcacc atccgaaaga gatatttca agaggcacta | 1500 |
| gttcaaatca cacttcccac tgtgcagaag gcactggcgt ccacatgcaa accagagctt | 1560 |
| cagaaatacg agcagttcat cttttgcagat cataccaata tgattcacgt tgaaaatgtc | 1620 |
| tatgaggaga ttttacatca gatcctgctt gatgaaactc tgaaagtgat aaaggaagct | 1680 |
| gctatcttga agaacacaa cttatttgaa gataacatgg ccttgcccag tgaaagtgtg | 1740 |
| tccagcttaa cagatctaaa gccccccaca gggtcaaacc aggccagccc tgccaggaga | 1800 |
| gcttctgcca ttctgccagg agttctgggt agtgagaccc tcagtaacga agtattccag | 1860 |
| gagtcagagg aagagaagca gcctgaggtc cctagctcgt tggccaaagg agaaagcctt | 1920 |
| tctctccctg ggccaagccc accccagat gggactgagc aggtgattat ttcaagagtg | 1980 |
| gatgacccg tggtgaatcc tgtggcaaca gaggacacag caggactccc gggcacatgc | 2040 |
| tcatcagagc tggagtttgg agggaccctt gaggatgaag aacccgccca ggaagagcca | 2100 |
| gaacccatca ctgcctcggg ttctttgaag gcgctcagaa agttgctgac agcgtccgtg | 2160 |
| gaagtaccag tggactctgc tccagtgatg gaagaagata cgaatgggga gagccacgtt | 2220 |
| ccccaagaaa atgaagaaga agaggaaaaa gagcccagtc aggcagctgc catccacccc | 2280 |
| gacaactgtg aagaaagtga agtcagcgag agggaggccc aacctccctg tcccgaggcc | 2340 |
| catgggagg agttggggg atttccagag gtaggcagcc cagcctctcc gccagccagt | 2400 |
| ggagggctca ccgaggagcc cctgggccc atggaggggg agctcccagg agaggcctgc | 2460 |
| acactcactg cccatgaagg aagaggggc aagtgtaccg aggaagggga tgcctcacag | 2520 |
| caagagggct gcaccttagg ttctgacccc atctgcctca gtgagagcca ggtttctgag | 2580 |
| gaacaagaag atgggagg gcaaagcagc gcggcccagg ccacggccag tgtgaatgca | 2640 |
| gaggagatca aggtagcccg tattcatgag tgtcagtggg tggtggagga tgctccaaac | 2700 |
| ccggatgtcc tgctgtcaca caaagatgac gtgaaggagg agaaggtgg tcaggagagt | 2760 |
| ttcccagagc tgccctcaga ggagtga | 2787 |

<210> SEQ ID NO 8
<211> LENGTH: 928
<212> TYPE: PRT
<213> ORGANISM: human

<400> SEQUENCE: 8

-continued

```
Met Gly Gly Ser Ala Ser Ser Gln Leu Asp Glu Gly Lys Cys Ala Tyr
1               5                   10                  15
Ile Arg Gly Lys Thr Glu Ala Ala Ile Lys Asn Phe Ser Pro Tyr Tyr
                20                  25                  30
Ser Arg Gln Tyr Ser Val Ala Phe Cys Asn His Val Arg Thr Glu Val
            35                  40                  45
Glu Gln Gln Arg Asp Leu Thr Ser Gln Phe Leu Lys Thr Lys Pro Pro
        50                  55                  60
Leu Ala Pro Gly Thr Ile Leu Tyr Glu Ala Glu Leu Ser Gln Phe Ser
65                  70                  75                  80
Glu Asp Ile Lys Lys Trp Lys Glu Arg Tyr Val Val Lys Asn Asp
                85                  90                  95
Tyr Ala Val Glu Ser Tyr Glu Asn Lys Glu Ala Tyr Gln Arg Gly Ala
                100                 105                 110
Ala Pro Lys Cys Arg Ile Leu Pro Ala Gly Gly Lys Val Leu Thr Ser
            115                 120                 125
Glu Asp Glu Tyr Asn Leu Leu Ser Asp Arg His Phe Pro Asp Pro Leu
        130                 135                 140
Ala Ser Ser Glu Lys Glu Asn Thr Gln Pro Phe Val Val Leu Pro Lys
145                 150                 155                 160
Glu Phe Pro Val Tyr Leu Trp Gln Pro Phe Phe Arg His Gly Tyr Phe
                165                 170                 175
Cys Phe His Glu Ala Ala Asp Gln Lys Arg Phe Ser Ala Leu Leu Ser
                180                 185                 190
Asp Cys Val Arg His Leu Asn His Asp Tyr Met Lys Gln Met Thr Phe
            195                 200                 205
Glu Ala Gln Ala Phe Leu Glu Ala Val Gln Phe Phe Arg Gln Glu Lys
        210                 215                 220
Gly His Tyr Gly Ser Trp Glu Met Ile Thr Gly Asp Glu Ile Gln Ile
225                 230                 235                 240
Leu Ser Asn Leu Val Met Glu Leu Leu Pro Thr Leu Gln Thr Asp
                245                 250                 255
Leu Leu Pro Lys Met Lys Gly Lys Lys Asn Asp Arg Lys Arg Thr Trp
                260                 265                 270
Leu Gly Leu Leu Glu Glu Ala Tyr Thr Leu Val Gln His Gln Val Ser
            275                 280                 285
Glu Gly Leu Ser Ala Leu Lys Glu Glu Cys Arg Ala Leu Thr Lys Gly
        290                 295                 300
Leu Glu Gly Thr Ile Arg Ser Asp Met Asp Gln Ile Val Asn Ser Lys
305                 310                 315                 320
Asn Tyr Leu Ile Gly Lys Ile Lys Ala Met Val Ala Gln Pro Ala Glu
                325                 330                 335
Lys Ser Cys Leu Glu Ser Val Gln Pro Phe Leu Ala Ser Ile Leu Glu
                340                 345                 350
Glu Leu Met Gly Pro Val Ser Ser Gly Phe Ser Glu Val Arg Val Leu
            355                 360                 365
Phe Glu Lys Glu Val Asn Glu Val Ser Gln Asn Phe Gln Thr Thr Lys
        370                 375                 380
Asp Ser Val Gln Leu Lys Glu His Leu Asp Arg Leu Met Asn Leu Pro
385                 390                 395                 400
Leu His Ser Val Lys Met Glu Pro Cys Tyr Thr Lys Val Asn Leu Leu
                405                 410                 415
His Glu Arg Leu Gln Asp Leu Lys Ser Arg Phe Arg Phe Pro His Ile
                420                 425                 430
```

-continued

```
Asp Leu Val Val Gln Arg Thr Gln Asn Tyr Met Gln Glu Leu Met Glu
            435                 440                 445
Asn Ala Val Phe Thr Phe Glu Gln Leu Leu Ser Pro His Leu Gln Gly
        450                 455                 460
Glu Ala Ser Lys Thr Ala Val Ala Ile Glu Lys Val Lys Leu Arg Val
465                 470                 475                 480
Leu Lys Gln Tyr Asp Tyr Asp Ser Ser Thr Ile Arg Lys Lys Ile Phe
                485                 490                 495
Gln Glu Ala Leu Val Gln Ile Thr Leu Pro Thr Val Gln Lys Ala Leu
            500                 505                 510
Ala Ser Thr Cys Lys Pro Glu Leu Gln Lys Tyr Glu Gln Phe Ile Phe
        515                 520                 525
Ala Asp His Thr Asn Met Ile His Val Glu Asn Val Tyr Glu Glu Ile
    530                 535                 540
Leu His Gln Ile Leu Leu Asp Glu Thr Leu Lys Val Ile Lys Glu Ala
545                 550                 555                 560
Ala Ile Leu Lys Lys His Asn Leu Phe Glu Asp Asn Met Ala Leu Pro
                565                 570                 575
Ser Glu Ser Val Ser Ser Leu Thr Asp Leu Lys Pro Pro Thr Gly Ser
            580                 585                 590
Asn Gln Ala Ser Pro Ala Arg Arg Ala Ser Ala Ile Leu Pro Gly Val
        595                 600                 605
Leu Gly Ser Glu Thr Leu Ser Asn Glu Val Phe Gln Glu Ser Glu Glu
    610                 615                 620
Glu Lys Gln Pro Glu Val Pro Ser Ser Leu Ala Lys Gly Glu Ser Leu
625                 630                 635                 640
Ser Leu Pro Gly Pro Ser Pro Pro Asp Gly Thr Glu Gln Val Ile
                645                 650                 655
Ile Ser Arg Val Asp Asp Pro Val Val Asn Pro Val Ala Thr Glu Asp
            660                 665                 670
Thr Ala Gly Leu Pro Gly Thr Cys Ser Ser Glu Leu Glu Phe Gly Gly
        675                 680                 685
Thr Leu Glu Asp Glu Glu Pro Ala Gln Glu Glu Pro Glu Pro Ile Thr
    690                 695                 700
Ala Ser Gly Ser Leu Lys Ala Leu Arg Lys Leu Leu Thr Ala Ser Val
705                 710                 715                 720
Glu Val Pro Val Asp Ser Ala Pro Val Met Glu Glu Asp Thr Asn Gly
                725                 730                 735
Glu Ser His Val Pro Gln Glu Asn Glu Glu Glu Glu Lys Glu Pro
            740                 745                 750
Ser Gln Ala Ala Ala Ile His Pro Asp Asn Cys Glu Ser Glu Val
        755                 760                 765
Ser Glu Arg Glu Ala Gln Pro Pro Cys Pro Glu Ala His Gly Glu Glu
    770                 775                 780
Leu Gly Gly Phe Pro Glu Val Gly Ser Pro Ala Ser Pro Ala Ser
785                 790                 795                 800
Gly Gly Leu Thr Glu Glu Pro Leu Gly Pro Met Gly Glu Leu Pro
                805                 810                 815
Gly Glu Ala Cys Thr Leu Thr Ala His Glu Gly Arg Gly Gly Lys Cys
            820                 825                 830
Thr Glu Glu Gly Asp Ala Ser Gln Gln Glu Gly Cys Thr Leu Gly Ser
        835                 840                 845
Asp Pro Ile Cys Leu Ser Glu Ser Gln Val Ser Glu Glu Gln Glu Glu
```

```
                850              855              860
Met Gly Gly Gln Ser Ser Ala Ala Gln Ala Thr Ala Ser Val Asn Ala
865              870              875              880

Glu Glu Ile Lys Val Ala Arg Ile His Glu Cys Gln Trp Val Glu
                885              890              895

Asp Ala Pro Asn Pro Asp Val Leu Leu Ser His Lys Asp Asp Val Lys
                900              905              910

Glu Gly Glu Gly Gly Gln Glu Ser Phe Pro Glu Leu Pro Ser Glu Glu
        915              920              925

<210> SEQ ID NO 9
<211> LENGTH: 8178
<212> TYPE: DNA
<213> ORGANISM: human

<400> SEQUENCE: 9
atggagcaaa ctgactgcaa accctaccag cctctaccaa agtcaagca tgaaatggat      60 ctagcttaca ccagttcttc tgatgagagt gaagatggaa gaaaaccaag acagtcatac    120
aactccaggg agaccctgca cgagtataac caggagctga ggatgaatta caatagccag    180
agtagaaaga ggaaagaagt agaaaaatct actcaagaga tggaattctg tgaaacctct    240
cacactctgt gctctggcta ccaaacagac atgcacagcg tttctcggca tggctaccag    300
ctagagatgg gatctgatgt ggacacagag acagaaggtg ctgcctcacc tgaccatgca    360
ctaagaatgt ggataagggg aatgaaatca gagcatagtt cctgtttgtc agccgggcc     420 aactctgcat tatccttgac tgacactgac catgaaagga agtctgatgg ggaaaatggt    480
ttcaaattct ctcctgtttg ttgtgacatg gaggctcaag ctgggtctac tcaagatgtg    540
cagagcagcc cacacaacca gttccacttc agacccctcc accgccacc tccgcctcct     600 catgcctgca cctgtgccag gaagccaccc cctgcagcgg actctcttca gaggagatca    660
atgactaccc gcagccagcc cagcccagct gctccagctc ccccaaccag cacgcaggat    720
tcagtccatc tgcataacag ctgggtcctg aacagcaaca taccattgga gaccaggcat    780
tccctgttca acatggatc tggttcctct gcgatcttca gtgcagccag tcagaactac     840
cctctgacat ccaataccgt gtactcgccc cctcccaggc ctcttcctcg aagcaccttt    900 tccccgacctg ccttaccctt taacaaacct tacaggtgct gcaactggaa gtgcacagca    960
ttgagcgcca ctgcaatcac agtgactttg gccttgttac tagcctatgt gattgcagtg   1020
catttgttcg gcctgacttg gcagttcaaa ccagttgaag agagctgta tgcaaatgga    1080 gttagcaaag gaacagggg gaccgagtcc atggacacta cttactctcc aattggagga    1140
aaagtttctg ataaatcaga gaaaaaagtg tttcagaagg gacgggcgat agacactgga    1200
gaagttgaca ttggtgcaca ggtcatgcag accattccac ctggtttatt ctggcgtttc   1260
cagattacta tccaccatcc aatatatctg aagttcaata tttctttagc caaggactct   1320
ctgctgggaa tttatggcag aagaaacatt ccacctacac atactcagtt tgattttgta   1380
aaactaatgg atggcaaaca gctggtcaag caggactcca agggctctga tgatacacag   1440 cactccccctc ggaacctgat cttaacttcg cttcaggaga caggtttcat agagtatatg   1500
gatcaaggac cttggtatct ggcgttttac aatgatggaa aaagatgga gcaagtattc   1560 gtgttaacta cagcaattga ataatggat gactgttcaa ccaattgcaa tggaaatgga   1620
gagtgtatct ctggccattg tcattgtttc ccaggattcc ttggacctga ctgtgctaga   1680
gattcctgcc ctgtgctgtg tggtgggaat ggagaatacg agaaaggaca ctgtgtctgc   1740
```

```
cggcatggct ggaaggggcc agagtgtgac gttccggaag aacaatgcat tgatccaaca    1800
tgctttggcc acggcacctg catcatggga gtctgcatct gtgtgccagg atacaaagga    1860
gaaatatgcg aggaagagga ctgcctagac ccaatgtgtt ccaaccatgg catctgtgta    1920
aaaggagaat gtcactgttc tactggctgg ggaggagtta actgtgaaac accacttcct    1980
gtatgtcaag agcagtgctc aggacacgga acttttcttc tggacgctgg agtatgcagc    2040
tgtgatccca gtggacagg atctgactgc tcaacagagc tgtgtaccat ggagtgtggt    2100
agccatggag tctgctcaag aggaatttgc cagtgtgaag aaggctgggt aggaccaaca    2160
tgtgaggaac gctcctgtca ttctcattgt actgagcatg ccaatgcaa agatggaaaa    2220
tgtgagtgta gccctggatg ggagggcgac cactgcacaa ttgctcacta cttagatgct    2280
gtccgagatg gctgcccagg gctctgcttt ggaaatggac gatgtaccct ggatcaaaat    2340
ggttggcact gtgtgtgtca ggtgggttgg agtgggacag gctgcaatgt tgtcatggaa    2400
atgctttgtg gagataactt ggacaatgat ggagatggtt taaccgactg tgtggatcct    2460
gactgttgtc aacaaagcaa ctgttatata agtcctctct gccagggctc accagatcct    2520
cttgacctca ttcagcaaag ccaaactctc ttctctcagc acacttcaag actttttttat   2580
gatcgaatca aattcctcat tggcaaggac agtactcatg tcattcctcc tgaggtgtca    2640
tttgacagca ggcgtgcctg tgtgattcga ggccaagtgg tggccataga tggaactcct    2700
ctagtgggag tgaatgtcag tttcttgcac cacagtgatt atgggtttac catcagccgg    2760
caagatggaa gctttgacct cgtggccatc ggtggcatct ctgtcatctt aatcttcgac    2820
cgatccccctt tcctgcctga agagaaaca ctctggttgc cttggaatca gtttattgtg    2880
gtagagaaag tcaccatgca gagagttgta tcagacccgc catcctgcga tatctccaac    2940
tttatcagcc caaaccctat tgtgcttcct tcaccgctca catcatttgg agggtcctgt    3000
ccagagaggg gaactattgt tcctgagctg caggttgtac aggaggaaat tcccattccc    3060
tccagctttg tgaggctgag ttacctgagc agccgcaccc ctgggtataa aaccctgcta    3120
cggatccttc tgcacacattc aacgattccc gtaggcatga taaaagtaca cctcacagta    3180
gctgtggaag ggcgactcac acagaagtgg tttcccgccg caattaatct tgtctacaca    3240
tttgcttgga acaagaccga tatctatgga cagaaggttt ggggcctggc agaggctttg    3300
gtatctgtgg gatatgaata tgaaacgtgc cctgactttta ttctctggga gcaaaggaca    3360
gtcgttttac aaggttttga gatggatgct tctaacctag gagactggtc tttgaataag    3420
catcacattt tgaatcctca aagtggaatc atacataaag ggaatggaga aaatatgttc    3480
atttcccagc agcccccagt catatcaacc ataatgggta atggacacca aaggagtgta    3540
gcctgcacca actgcaatgg cccagcccac aacaacaaac tctttgctcc tgtcgcctta    3600
gcttctggcc ctgatggcag tgtgtatgtt ggcgacttca attttgtaag gagaatattt    3660
ccctcgggaa actccgttag tattttggaa ttaagcacaa gtcctgctca caatactat    3720
ctggctatgg accctgtgtc tgaatcactc tatctatcag acaccaatac tcgcaaagtc    3780
tacaagttga atctcttgt ggagacgaaa gatctgtcca agaattttga agtggtggca    3840
ggaactggtg atcagtgcct tccctttgac cagagtcatt gtggagatgg tgggagagca    3900
tcggaagctt cactgaatag ccctcgaggc atcacagttg ataggcatgg atttatttac    3960
tttgtggatg ggactatgat tcgcaaaatt gatgagaatg ctgtgatcac aactgtaatc    4020
ggctcaaatg gtctgacttc cacacaacca ctgagctgtg actcaggaat ggacatcact    4080
caggtgcgat tagagtggcc aacagacctt gcagtaaatc ctatggacaa ttcattgtat    4140
```

```
gtcttggata acaacattgt gctgcaaatt tctgagaaca ggcgtgttcg gatcatcgca    4200
ggacgcccca ttcactgcca ggtgccaggc atcgatcatt tcctggtcag caaggtagca    4260
attcactcca ctctagagtc agcgagggcc atcagtgtct cccacagcgg gctgctcttc    4320
atagctgaaa cagacgagag gaaagtaaac cgcattcagc aagtaaccac caatggggag    4380
atctacatca tcgctggtgc ccccactgac tgtgactgca aaattgatcc aaactgtgac    4440 tgttttcag gtgatggtgg ctatgccaaa gatgcaaaga tgaaagcccc ttcctcctta    4500
gcagtgtcgc ctgatggaac cctctatgtg gcagacctcg gaaatgttcg aattcgtacc    4560
atcagcagga accaagccca cctgaatgac atgaacattt atgagattgc ttcacccgct    4620
gatcaggaac tgtaccagtt cactgtaaat ggaacccacc tacacaccct gaacttgata    4680
acaagggact atgtttataa cttcacctac aattctgaag gtgacttggg cgcgattacc    4740
agcagcaatg gcaattcagt gcacattcgc cgtgatgcag gcggaatgcc gctatggctt    4800
gtggtgcctg gcgacaagt atactggctg actataagca gcaatggagt cctgaaaaga    4860
gtgtcagccc aaggctataa tccggcctta atgacctatc caggaaacac agggcttctg    4920
gctaccaaaa gtaacgaaaa tggatggaca accgtttatg agtatgaccc cgagggacac    4980
ctgaccaatg caacgtttcc cactggagag gtcagcagct tccacagtga cctggagaag    5040
ctgacaaaag tggagctaga tacttccaac cgtgaaaatg tcctcatgtc aaccaacttg    5100
acggcaacta gtaccatata tattttaaaa caagaaaata ctcaaagtac ctatcgggtg    5160
aatccagatg gttccctgcg tgtcactttt gccagcggga tggagatcgg cctcagctca    5220
gagccccaca tcctggcagg ggcagtcaac cctaccctgg gcaaatgcaa catctcattg    5280
cccggagagc acaatgcaaa cctcatcgag tggcggcaga ggaaggagca aaacaaaggc    5340
aatgtttcgg cttttgaaag gaggctgagg gcccacaaca gaaacctact ctccatagat    5400
tttgatcata taacccgcac aggaaagatc tatgatgacc atcgaaaatt caccccttcga    5460 attctttatg accagactgg gcgacccatt ctgtggtctc ctgtaagcag atataatgaa    5520
gtgaacatca catattcacc ttcgggattg gtgacgttta ttcaaagagg aacgtggaat    5580 gaaaaatgg aatatgacca gagtgggaaa attatttcaa gaacttgggc tgatgggaaa    5640
atttggagct atacctactt agaaaaatct gtgatgcttc tcctacacag ccagcggcgt    5700
tacatctttg agtatgacca atcagattgc ctgctgtcag ttaccatgcc tagcatggtg    5760
cgccacagct acaaaccat gctttcagtg ggctactacc gtaatatcta caccccaccg    5820
gacagtagca cttcttttat ccaagactat agtcgagatg gccgattgct acagaccctg    5880
catctgggga cagggcgcag agtcttatac aagtacacca agcaagcaag gctttctgag    5940
gttctctatg ataccactca ggtcacatta acatatgaag agtcttctgg agtgattaag    6000
acaatacacc tgatgcatga cggattcatc tgcacaatca gatacaggca aacaggacct    6060
cttattggac gccagatttt cagattcagt gaagaaggcc ttgtgaatgc acggttcgac    6120
tacagctaca caaattccg agtcacaagc atgcaagctg taatcaatga aaccccttg    6180 cctatagatc tttaccgata tgttgatgtc tctggcagaa cagagcagtt tggaaaattc    6240
agtgtaatta attacgattt aaatcaggtc ataactacta cagtgatgaa acacaccaaa    6300
atcttcagtg ccaatggaca agtcattgaa gtccaatatg aaatcctaaa ggcaattgcc    6360
tactggatga ccattcaata tgataatgtg ggccgacatg gtaatatgtg cataagggta    6420
ggagtagatg ccaatataac aaggtacttc tatgaatacg atgctgatgg gcaacttcag    6480 actgttctg taaatgacaa aacccagtgg cgttatagtt acgatctgaa tggagacatc    6540
```

```
aacctcttaa gccatgggaa gagtgctcgt cttactcctc tccgatatga cctccgagac    6600
cgcatcacca gattaggaga aattcagtat aaaatggatg aagatggctt tctgaggcag    6660
aggggaaatg atattttga atataattct aatggcctgc tgcagaaagc ctacaataag    6720
gcttctggct ggactgtgca gtattactat gatgggcttg ggcgacgtgt cgcgagtaag    6780
tccagcctag ggcagcacct tcagttcttt gtcgacgcga ccgcgaaccc cataagagtt    6840
actcatttgt acaaccacac aagctcggag attacatctc tgtattatga ctccaaggt    6900
caccttattg ccatggagtt aagcagtggt gaagaatatt atgtagcctg tgataataca    6960
ggtaccccac tagctgtgtt cagcagccga ggtcaggtca taaggagat actatacaca    7020
ccttatggcg atatctatca tgacacttac cctgactttc aggtcataat tggttttcat    7080
ggaggactct atgatttcct tactaaatta gtgcacctgg ggcaaaggga ttatgatgtt    7140
gttgctggca gatggacaac ggcctatcat acatatgga aacagttgaa cctccttcct    7200
aaaccattca acctctactc ctttgaaaat aactacccag ttggcaaaat tcaagatgtt    7260
gcaaagtata ccacagacat cagaagttgg ttggagctat ttggtttcca attacacaat    7320
gtactacctg gatttcccaa acctgaatta gaaaatttag aattaactta cgagcttcta    7380
cggcttcaga caaaaactca agagtgggat cctggaaaga ctatcctggg cattcagtgt    7440
gaactccaga aacagctcag gaatttcatt tccttggacc aactacctat gactccccga    7500
tacaatgatg gacggtgcct tgaaggaggg aagcaaccaa ggtttgctgc tgtccttct    7560
gttttttggga aaggtataaa atttgccatc aaggatggca tagtaacagc tgatattata    7620
ggagtagcca atgaagatag caggcggctt gctgccattc tcaataatgc ccattacctg    7680
gaaaacctac atttaccat agaggggagg acactcact acttcattaa gcttgggtct    7740
ctggaggaag acctggtgct catcggtaac actgggggga ggcggattct ggagaatggt    7800
gtcaatgtca ctgtgtccca gatgacttct ctgttgaatg gaggactag acggtttgca    7860
gatattcagc tccagcatgg agccctgtgc ttcaacatcc ggtatgggac aactgtcgaa    7920
gaggaaaaga tcacgtgtt ggagattgcc agacagcgcg cagtggccca ggcctggact    7980
aaggaacaaa gaaggctgca agagggggaa gaggggatta gggcatggac agaagggaa    8040
aagcagcagc ttttgagcac tgggcgggta caaggttacg atgggtattt tgttttgtct    8100
gttgagcagt atttagaact ttctgacagt gccaataata ttcactttat gagacagagc    8160
gaaataggca ggaggtaa                                                 8178

<210> SEQ ID NO 10
<211> LENGTH: 2725
<212> TYPE: PRT
<213> ORGANISM: human

<400> SEQUENCE: 10

Met Glu Gln Thr Asp Cys Lys Pro Tyr Gln Pro Leu Pro Lys Val Lys
1               5                   10                  15

His Glu Met Asp Leu Ala Tyr Thr Ser Ser Ser Asp Glu Ser Glu Asp
                20                  25                  30

Gly Arg Lys Pro Arg Gln Ser Tyr Asn Ser Arg Glu Thr Leu His Glu
            35                  40                  45

Tyr Asn Gln Glu Leu Arg Met Asn Tyr Asn Ser Gln Ser Arg Lys Arg
        50                  55                  60

Lys Glu Val Glu Lys Ser Thr Gln Glu Met Glu Phe Cys Glu Thr Ser
65                  70                  75                  80

His Thr Leu Cys Ser Gly Tyr Gln Thr Asp Met His Ser Val Ser Arg
```

-continued

```
                85                  90                  95
His Gly Tyr Gln Leu Glu Met Gly Ser Asp Val Asp Thr Glu Thr Glu
            100                 105                 110

Gly Ala Ala Ser Pro Asp His Ala Leu Arg Met Trp Ile Arg Gly Met
            115                 120                 125

Lys Ser Glu His Ser Ser Cys Leu Ser Ser Arg Ala Asn Ser Ala Leu
            130                 135                 140

Ser Leu Thr Asp Thr Asp His Glu Arg Lys Ser Asp Gly Glu Asn Gly
145                 150                 155                 160

Phe Lys Phe Ser Pro Val Cys Cys Asp Met Glu Ala Gln Ala Gly Ser
                165                 170                 175

Thr Gln Asp Val Gln Ser Ser Pro His Asn Gln Phe Thr Phe Arg Pro
            180                 185                 190

Leu Pro Pro Pro Pro Pro His Ala Cys Thr Cys Ala Arg Lys
            195                 200                 205

Pro Pro Pro Ala Ala Asp Ser Leu Gln Arg Arg Ser Met Thr Thr Arg
    210                 215                 220

Ser Gln Pro Ser Pro Ala Ala Pro Ala Pro Thr Ser Thr Gln Asp
225                 230                 235                 240

Ser Val His Leu His Asn Ser Trp Val Leu Asn Ser Asn Ile Pro Leu
                245                 250                 255

Glu Thr Arg His Ser Leu Phe Lys His Gly Ser Gly Ser Ala Ile
            260                 265                 270

Phe Ser Ala Ala Ser Gln Asn Tyr Pro Leu Thr Ser Asn Thr Val Tyr
            275                 280                 285

Ser Pro Pro Pro Arg Pro Leu Pro Arg Ser Thr Phe Ser Arg Pro Ala
    290                 295                 300

Phe Thr Phe Asn Lys Pro Tyr Arg Cys Cys Asn Trp Lys Cys Thr Ala
305                 310                 315                 320

Leu Ser Ala Thr Ala Ile Thr Val Thr Leu Ala Leu Leu Ala Tyr
                325                 330                 335

Val Ile Ala Val His Leu Phe Gly Leu Thr Trp Gln Leu Gln Pro Val
            340                 345                 350

Glu Gly Glu Leu Tyr Ala Asn Gly Val Ser Lys Gly Asn Arg Gly Thr
            355                 360                 365

Glu Ser Met Asp Thr Thr Tyr Ser Pro Ile Gly Gly Lys Val Ser Asp
            370                 375                 380

Lys Ser Glu Lys Lys Val Phe Gln Lys Gly Arg Ala Ile Asp Thr Gly
385                 390                 395                 400

Glu Val Asp Ile Gly Ala Gln Val Met Gln Thr Ile Pro Pro Gly Leu
                405                 410                 415

Phe Trp Arg Phe Gln Ile Thr Ile His His Pro Ile Tyr Leu Lys Phe
            420                 425                 430

Asn Ile Ser Leu Ala Lys Asp Ser Leu Leu Gly Ile Tyr Gly Arg Arg
            435                 440                 445

Asn Ile Pro Pro Thr His Thr Gln Phe Asp Phe Val Lys Leu Met Asp
    450                 455                 460

Gly Lys Gln Leu Val Lys Gln Asp Ser Lys Gly Ser Asp Asp Thr Gln
465                 470                 475                 480

His Ser Pro Arg Asn Leu Ile Leu Thr Ser Leu Gln Glu Thr Gly Phe
                485                 490                 495

Ile Glu Tyr Met Asp Gln Gly Pro Trp Tyr Leu Ala Phe Tyr Asn Asp
            500                 505                 510
```

-continued

```
Gly Lys Lys Met Glu Gln Val Phe Val Leu Thr Thr Ala Ile Glu Ile
        515                 520                 525
Met Asp Asp Cys Ser Thr Asn Cys Asn Gly Asn Gly Glu Cys Ile Ser
    530                 535                 540
Gly His Cys His Cys Phe Pro Gly Phe Leu Gly Pro Asp Cys Ala Arg
545                 550                 555                 560
Asp Ser Cys Pro Val Leu Cys Gly Asn Gly Glu Tyr Glu Lys Gly
                565                 570                 575
His Cys Val Cys Arg His Gly Trp Lys Gly Pro Glu Cys Asp Val Pro
            580                 585                 590
Glu Glu Gln Cys Ile Asp Pro Thr Cys Phe Gly His Gly Thr Cys Ile
        595                 600                 605
Met Gly Val Cys Ile Cys Val Pro Gly Tyr Lys Gly Glu Ile Cys Glu
    610                 615                 620
Glu Glu Asp Cys Leu Asp Pro Met Cys Ser Asn His Gly Ile Cys Val
625                 630                 635                 640
Lys Gly Glu Cys His Cys Ser Thr Gly Trp Gly Gly Val Asn Cys Glu
                645                 650                 655
Thr Pro Leu Pro Val Cys Gln Glu Gln Cys Ser Gly His Gly Thr Phe
            660                 665                 670
Leu Leu Asp Ala Gly Val Cys Ser Cys Asp Pro Lys Trp Thr Gly Ser
        675                 680                 685
Asp Cys Ser Thr Glu Leu Cys Thr Met Glu Cys Gly Ser His Gly Val
    690                 695                 700
Cys Ser Arg Gly Ile Cys Gln Cys Glu Glu Gly Trp Val Gly Pro Thr
705                 710                 715                 720
Cys Glu Glu Arg Ser Cys His Ser His Cys Thr Glu His Gly Gln Cys
                725                 730                 735
Lys Asp Gly Lys Cys Glu Cys Ser Pro Gly Trp Glu Gly Asp His Cys
            740                 745                 750
Thr Ile Ala His Tyr Leu Asp Ala Val Arg Asp Gly Cys Pro Gly Leu
        755                 760                 765
Cys Phe Gly Asn Gly Arg Cys Thr Leu Asp Gln Asn Gly Trp His Cys
    770                 775                 780
Val Cys Gln Val Gly Trp Ser Gly Thr Gly Cys Asn Val Val Met Glu
785                 790                 795                 800
Met Leu Cys Gly Asp Asn Leu Asp Asn Asp Gly Asp Gly Leu Thr Asp
                805                 810                 815
Cys Val Asp Pro Asp Cys Cys Gln Gln Ser Asn Cys Tyr Ile Ser Pro
            820                 825                 830
Leu Cys Gln Gly Ser Pro Asp Pro Leu Asp Leu Ile Gln Gln Ser Gln
        835                 840                 845
Thr Leu Phe Ser Gln His Thr Ser Arg Leu Phe Tyr Asp Arg Ile Lys
    850                 855                 860
Phe Leu Ile Gly Lys Asp Ser Thr His Val Ile Pro Pro Glu Val Ser
865                 870                 875                 880
Phe Asp Ser Arg Arg Ala Cys Val Ile Arg Gly Gln Val Val Ala Ile
                885                 890                 895
Asp Gly Thr Pro Leu Val Gly Val Asn Val Ser Phe Leu His His Ser
            900                 905                 910
Asp Tyr Gly Phe Thr Ile Ser Arg Gln Asp Gly Ser Phe Asp Leu Val
        915                 920                 925
Ala Ile Gly Gly Ile Ser Val Ile Leu Ile Phe Asp Arg Ser Pro Phe
    930                 935                 940
```

```
Leu Pro Glu Lys Arg Thr Leu Trp Leu Pro Trp Asn Gln Phe Ile Val
945                 950                 955                 960

Val Glu Lys Val Thr Met Gln Arg Val Val Ser Asp Pro Pro Ser Cys
                965                 970                 975

Asp Ile Ser Asn Phe Ile Ser Pro Asn Pro Ile Val Leu Pro Ser Pro
            980                 985                 990

Leu Thr Ser Phe Gly Gly Ser Cys Pro Glu Arg Gly Thr Ile Val Pro
        995                 1000                1005

Glu Leu Gln Val Val Gln Glu Glu Ile Pro Ile Pro Ser Ser Phe
    1010                1015                1020

Val Arg Leu Ser Tyr Leu Ser Ser Arg Thr Pro Gly Tyr Lys Thr
    1025                1030                1035

Leu Leu Arg Ile Leu Leu Thr His Ser Thr Ile Pro Val Gly Met
    1040                1045                1050

Ile Lys Val His Leu Thr Val Ala Val Glu Gly Arg Leu Thr Gln
    1055                1060                1065

Lys Trp Phe Pro Ala Ala Ile Asn Leu Val Tyr Thr Phe Ala Trp
    1070                1075                1080

Asn Lys Thr Asp Ile Tyr Gly Gln Lys Val Trp Gly Leu Ala Glu
    1085                1090                1095

Ala Leu Val Ser Val Gly Tyr Glu Tyr Glu Thr Cys Pro Asp Phe
    1100                1105                1110

Ile Leu Trp Glu Gln Arg Thr Val Val Leu Gln Gly Phe Glu Met
    1115                1120                1125

Asp Ala Ser Asn Leu Gly Asp Trp Ser Leu Asn Lys His His Ile
    1130                1135                1140

Leu Asn Pro Gln Ser Gly Ile Ile His Lys Gly Asn Gly Glu Asn
    1145                1150                1155

Met Phe Ile Ser Gln Gln Pro Pro Val Ile Ser Thr Ile Met Gly
    1160                1165                1170

Asn Gly His Gln Arg Ser Val Ala Cys Thr Asn Cys Asn Gly Pro
    1175                1180                1185

Ala His Asn Asn Lys Leu Phe Ala Pro Val Ala Leu Ala Ser Gly
    1190                1195                1200

Pro Asp Gly Ser Val Tyr Val Gly Asp Phe Asn Phe Val Arg Arg
    1205                1210                1215

Ile Phe Pro Ser Gly Asn Ser Val Ser Ile Leu Glu Leu Ser Thr
    1220                1225                1230

Ser Pro Ala His Lys Tyr Tyr Leu Ala Met Asp Pro Val Ser Glu
    1235                1240                1245

Ser Leu Tyr Leu Ser Asp Thr Asn Thr Arg Lys Val Tyr Lys Leu
    1250                1255                1260

Lys Ser Leu Val Glu Thr Lys Asp Leu Ser Lys Asn Phe Glu Val
    1265                1270                1275

Val Ala Gly Thr Gly Asp Gln Cys Leu Pro Phe Asp Gln Ser His
    1280                1285                1290

Cys Gly Asp Gly Gly Arg Ala Ser Glu Ala Ser Leu Asn Ser Pro
    1295                1300                1305

Arg Gly Ile Thr Val Asp Arg His Gly Phe Ile Tyr Phe Val Asp
    1310                1315                1320

Gly Thr Met Ile Arg Lys Ile Asp Glu Asn Ala Val Ile Thr Thr
    1325                1330                1335

Val Ile Gly Ser Asn Gly Leu Thr Ser Thr Gln Pro Leu Ser Cys
```

```
              1340             1345             1350

Asp Ser Gly Met Asp Ile Thr Gln Val Arg Leu Glu Trp Pro Thr
    1355             1360             1365

Asp Leu Ala Val Asn Pro Met Asp Asn Ser Leu Tyr Val Leu Asp
    1370             1375             1380

Asn Asn Ile Val Leu Gln Ile Ser Glu Asn Arg Arg Val Arg Ile
    1385             1390             1395

Ile Ala Gly Arg Pro Ile His Cys Gln Val Pro Gly Ile Asp His
    1400             1405             1410

Phe Leu Val Ser Lys Val Ala Ile His Ser Thr Leu Glu Ser Ala
    1415             1420             1425

Arg Ala Ile Ser Val Ser His Ser Gly Leu Leu Phe Ile Ala Glu
    1430             1435             1440

Thr Asp Glu Arg Lys Val Asn Arg Ile Gln Gln Val Thr Thr Asn
    1445             1450             1455

Gly Glu Ile Tyr Ile Ile Ala Gly Ala Pro Thr Asp Cys Asp Cys
    1460             1465             1470

Lys Ile Asp Pro Asn Cys Asp Cys Phe Ser Gly Asp Gly Gly Tyr
    1475             1480             1485

Ala Lys Asp Ala Lys Met Lys Ala Pro Ser Ser Leu Ala Val Ser
    1490             1495             1500

Pro Asp Gly Thr Leu Tyr Val Ala Asp Leu Gly Asn Val Arg Ile
    1505             1510             1515

Arg Thr Ile Ser Arg Asn Gln Ala His Leu Asn Asp Met Asn Ile
    1520             1525             1530

Tyr Glu Ile Ala Ser Pro Ala Asp Gln Glu Leu Tyr Gln Phe Thr
    1535             1540             1545

Val Asn Gly Thr His Leu His Thr Leu Asn Leu Ile Thr Arg Asp
    1550             1555             1560

Tyr Val Tyr Asn Phe Thr Tyr Asn Ser Glu Gly Asp Leu Gly Ala
    1565             1570             1575

Ile Thr Ser Ser Asn Gly Asn Ser Val His Ile Arg Arg Asp Ala
    1580             1585             1590

Gly Gly Met Pro Leu Trp Leu Val Val Pro Gly Gly Gln Val Tyr
    1595             1600             1605

Trp Leu Thr Ile Ser Ser Asn Gly Val Leu Lys Arg Val Ser Ala
    1610             1615             1620

Gln Gly Tyr Asn Pro Ala Leu Met Thr Tyr Pro Gly Asn Thr Gly
    1625             1630             1635

Leu Leu Ala Thr Lys Ser Asn Glu Asn Gly Trp Thr Thr Val Tyr
    1640             1645             1650

Glu Tyr Asp Pro Glu Gly His Leu Thr Asn Ala Thr Phe Pro Thr
    1655             1660             1665

Gly Glu Val Ser Ser Phe His Ser Asp Leu Glu Lys Leu Thr Lys
    1670             1675             1680

Val Glu Leu Asp Thr Ser Asn Arg Glu Asn Val Leu Met Ser Thr
    1685             1690             1695

Asn Leu Thr Ala Thr Ser Thr Ile Tyr Ile Leu Lys Gln Glu Asn
    1700             1705             1710

Thr Gln Ser Thr Tyr Arg Val Asn Pro Asp Gly Ser Leu Arg Val
    1715             1720             1725

Thr Phe Ala Ser Gly Met Glu Ile Gly Leu Ser Ser Glu Pro His
    1730             1735             1740
```

-continued

Ile Leu Ala Gly Ala Val Asn Pro Thr Leu Gly Lys Cys Asn Ile
1745                    1750                1755

Ser Leu Pro Gly Glu His Asn Ala Asn Leu Ile Glu Trp Arg Gln
1760                    1765                1770

Arg Lys Glu Gln Asn Lys Gly Asn Val Ser Ala Phe Glu Arg Arg
1775                    1780                1785

Leu Arg Ala His Asn Arg Asn Leu Leu Ser Ile Asp Phe Asp His
1790                    1795                1800

Ile Thr Arg Thr Gly Lys Ile Tyr Asp Asp His Arg Lys Phe Thr
1805                    1810                1815

Leu Arg Ile Leu Tyr Asp Gln Thr Gly Arg Pro Ile Leu Trp Ser
1820                    1825                1830

Pro Val Ser Arg Tyr Asn Glu Val Asn Ile Thr Tyr Ser Pro Ser
1835                    1840                1845

Gly Leu Val Thr Phe Ile Gln Arg Gly Thr Trp Asn Glu Lys Met
1850                    1855                1860

Glu Tyr Asp Gln Ser Gly Lys Ile Ile Ser Arg Thr Trp Ala Asp
1865                    1870                1875

Gly Lys Ile Trp Ser Tyr Thr Tyr Leu Glu Lys Ser Val Met Leu
1880                    1885                1890

Leu Leu His Ser Gln Arg Arg Tyr Ile Phe Glu Tyr Asp Gln Ser
1895                    1900                1905

Asp Cys Leu Leu Ser Val Thr Met Pro Ser Met Val Arg His Ser
1910                    1915                1920

Leu Gln Thr Met Leu Ser Val Gly Tyr Tyr Arg Asn Ile Tyr Thr
1925                    1930                1935

Pro Pro Asp Ser Ser Thr Ser Phe Ile Gln Asp Tyr Ser Arg Asp
1940                    1945                1950

Gly Arg Leu Leu Gln Thr Leu His Leu Gly Thr Gly Arg Arg Val
1955                    1960                1965

Leu Tyr Lys Tyr Thr Lys Gln Ala Arg Leu Ser Glu Val Leu Tyr
1970                    1975                1980

Asp Thr Thr Gln Val Thr Leu Thr Tyr Glu Glu Ser Ser Gly Val
1985                    1990                1995

Ile Lys Thr Ile His Leu Met His Asp Gly Phe Ile Cys Thr Ile
2000                    2005                2010

Arg Tyr Arg Gln Thr Gly Pro Leu Ile Gly Arg Gln Ile Phe Arg
2015                    2020                2025

Phe Ser Glu Glu Gly Leu Val Asn Ala Arg Phe Asp Tyr Ser Tyr
2030                    2035                2040

Asn Asn Phe Arg Val Thr Ser Met Gln Ala Val Ile Asn Glu Thr
2045                    2050                2055

Pro Leu Pro Ile Asp Leu Tyr Arg Tyr Val Asp Val Ser Gly Arg
2060                    2065                2070

Thr Glu Gln Phe Gly Lys Phe Ser Val Ile Asn Tyr Asp Leu Asn
2075                    2080                2085

Gln Val Ile Thr Thr Thr Val Met Lys His Thr Lys Ile Phe Ser
2090                    2095                2100

Ala Asn Gly Gln Val Ile Glu Val Gln Tyr Glu Ile Leu Lys Ala
2105                    2110                2115

Ile Ala Tyr Trp Met Thr Ile Gln Tyr Asp Asn Val Gly Arg His
2120                    2125                2130

Gly Asn Met Cys Ile Arg Val Gly Val Asp Ala Asn Ile Thr Arg
2135                    2140                2145

```
Tyr Phe Tyr Glu Tyr Asp Ala Asp Gly Gln Leu Gln Thr Val Ser
    2150            2155                2160
Val Asn Asp Lys Thr Gln Trp Arg Tyr Ser Tyr Asp Leu Asn Gly
    2165            2170                2175
Asp Ile Asn Leu Leu Ser His Gly Lys Ser Ala Arg Leu Thr Pro
    2180            2185                2190
Leu Arg Tyr Asp Leu Arg Asp Arg Ile Thr Arg Leu Gly Glu Ile
    2195            2200                2205
Gln Tyr Lys Met Asp Glu Asp Gly Phe Leu Arg Gln Arg Gly Asn
    2210            2215                2220
Asp Ile Phe Glu Tyr Asn Ser Asn Gly Leu Leu Gln Lys Ala Tyr
    2225            2230                2235
Asn Lys Ala Ser Gly Trp Thr Val Gln Tyr Tyr Tyr Asp Gly Leu
    2240            2245                2250
Gly Arg Arg Val Ala Ser Lys Ser Ser Leu Gly Gln His Leu Gln
    2255            2260                2265
Phe Phe Val Asp Ala Thr Ala Asn Pro Ile Arg Val Thr His Leu
    2270            2275                2280
Tyr Asn His Thr Ser Ser Glu Ile Thr Ser Leu Tyr Tyr Asp Leu
    2285            2290                2295
Gln Gly His Leu Ile Ala Met Glu Leu Ser Ser Gly Glu Glu Tyr
    2300            2305                2310
Tyr Val Ala Cys Asp Asn Thr Gly Thr Pro Leu Ala Val Phe Ser
    2315            2320                2325
Ser Arg Gly Gln Val Ile Lys Glu Ile Leu Tyr Thr Pro Tyr Gly
    2330            2335                2340
Asp Ile Tyr His Asp Thr Tyr Pro Asp Phe Gln Val Ile Ile Gly
    2345            2350                2355
Phe His Gly Gly Leu Tyr Asp Phe Leu Thr Lys Leu Val His Leu
    2360            2365                2370
Gly Gln Arg Asp Tyr Asp Val Val Ala Gly Arg Trp Thr Thr Ala
    2375            2380                2385
Tyr His His Ile Trp Lys Gln Leu Asn Leu Leu Pro Lys Pro Phe
    2390            2395                2400
Asn Leu Tyr Ser Phe Glu Asn Asn Tyr Pro Val Gly Lys Ile Gln
    2405            2410                2415
Asp Val Ala Lys Tyr Thr Thr Asp Ile Arg Ser Trp Leu Glu Leu
    2420            2425                2430
Phe Gly Phe Gln Leu His Asn Val Leu Pro Gly Phe Pro Lys Pro
    2435            2440                2445
Glu Leu Glu Asn Leu Glu Leu Thr Tyr Glu Leu Leu Arg Leu Gln
    2450            2455                2460
Thr Lys Thr Gln Glu Trp Asp Pro Gly Lys Thr Ile Leu Gly Ile
    2465            2470                2475
Gln Cys Glu Leu Gln Lys Gln Leu Arg Asn Phe Ile Ser Leu Asp
    2480            2485                2490
Gln Leu Pro Met Thr Pro Arg Tyr Asn Asp Gly Arg Cys Leu Glu
    2495            2500                2505
Gly Gly Lys Gln Pro Arg Phe Ala Ala Val Pro Ser Val Phe Gly
    2510            2515                2520
Lys Gly Ile Lys Phe Ala Ile Lys Asp Gly Ile Val Thr Ala Asp
    2525            2530                2535
Ile Ile Gly Val Ala Asn Glu Asp Ser Arg Arg Leu Ala Ala Ile
```

-continued

```
               2540                2545                2550

Leu Asn Asn Ala His Tyr Leu Glu Asn Leu His Phe Thr Ile Glu
    2555                2560                2565

Gly Arg Asp Thr His Tyr Phe Ile Lys Leu Gly Ser Leu Glu Glu
    2570                2575                2580

Asp Leu Val Leu Ile Gly Asn Thr Gly Arg Arg Ile Leu Glu
    2585                2590                2595

Asn Gly Val Asn Val Thr Val Ser Gln Met Thr Ser Leu Leu Asn
    2600                2605                2610

Gly Arg Thr Arg Arg Phe Ala Asp Ile Gln Leu Gln His Gly Ala
    2615                2620                2625

Leu Cys Phe Asn Ile Arg Tyr Gly Thr Thr Val Glu Glu Glu Lys
    2630                2635                2640

Asn His Val Leu Glu Ile Ala Arg Gln Arg Ala Val Ala Gln Ala
    2645                2650                2655

Trp Thr Lys Glu Gln Arg Arg Leu Gln Glu Gly Glu Glu Gly Ile
    2660                2665                2670

Arg Ala Trp Thr Glu Gly Glu Lys Gln Gln Leu Leu Ser Thr Gly
    2675                2680                2685

Arg Val Gln Gly Tyr Asp Gly Tyr Phe Val Leu Ser Val Glu Gln
    2690                2695                2700

Tyr Leu Glu Leu Ser Asp Ser Ala Asn Asn Ile His Phe Met Arg
    2705                2710                2715

Gln Ser Glu Ile Gly Arg Arg
    2720                2725

<210> SEQ ID NO 11
<211> LENGTH: 3228
<212> TYPE: DNA
<213> ORGANISM: human

<400> SEQUENCE: 11
atgcgaggtg gcaaatgcaa catgctctcc agtttggggt gtctacttct ctgtggaagt      60
attacactag ccctgggaaa tgcacagaaa ttgccaaaag gtaaaaggcc aaacctcaaa    120
gtccacatca ataccacaag tgactccatc ctcttgaagt tcttgcgtcc aagtccaaat    180
gtaaagcttg aaggtcttct cctgggatat ggcagcaatg tatcaccaaa ccagtacttc    240
cctcttcccg ctgaagggaa attcacagaa gctatagttg atgcagagcc gaaatatctg    300
atagttgtgc gacctgctcc acctccaagt caaaagaagt catgttcagg taaaactcgt    360
tctcgcaaac ctctgcagct ggtggttggc actctgacac cgagctcagt cttcctgtcc    420
tggggtttcc tcatcaaccc acaccatgac tggacattgc aagtcactg tcccaatgac    480 agattttata caattcgcta tcgagaaaag gataaagaaa agaagtggat ttttcaaatc    540
tgtccagcca ctgaaacaat tgtggaaaac ctaaagccca cacagtttta tgaatttgga    600
gtgaaagaca atgtggaagg tggaatttgg agtaagattt tcaatcacaa gactgttgtt    660
ggaagtaaaa aagtaaatgg gaaaatccaa agtacctatg accaagacca cagtgccca    720 gcatatgtcc caaggaaact aatcccaata caatcatca agcaagtgat tcagaatgtt    780
actcacaagg attcagctaa atccccagaa aaagctccac tgggaggagt gatactagtc    840
caccttatta ttccaggtct taatgaaact actgtaaaac ttcctgcatc cctaatgttt    900
gagatttcag atgcactcaa gacacaatta gctaagaatg aaaccttggc attacctgcc    960
gaatctaaaa caccagaggt tgaaaaaatc tcagcacgac ccacaacagt gactcctgaa   1020
```

```
acagttccaa gaagcactaa acccactacg tctagtgcat tagatgtttc agaaacaaca    1080
ctggcttcaa gtgaaaagcc atggattgtg cctacagcta aaatatctga agattccaaa    1140
gttctgcagc ctcaaactgc aacttatgat gttttctcaa gccctacaac atcagatgag    1200
cctgagatat cagattccta cacagcaaca agtgatcgta ttctggattc tatcccacct    1260
aaaacttcta gaactcttga acagccaagg gcaacactgg ctccaagtga aacaccattt    1320
gttcctcaaa aactggaaat ctttaccagt ccagaaatgc agcctacgac acctgctccc    1380
cagcaaacta catctatccc ttctacacct aaacgacgcc cccggcccaa accgccaaga    1440
accaaacctg aaagaaccac aagtgccgga acaattacac ctaaaatttc taaaagccct    1500
gaacctacat ggacaacacc ggctcccggt aaaacacaat ttatttctct gaaacctaaa    1560
atccctctca gcccagaagt gacacacacc aaacctgctc ccaagcagac accacgtgct    1620
cctcctaagc caaaaacatc accacgccca agaatccac aaacacaacc agttcctaag     1680
gtgccccagc gtgttactgc aaaaccaaaa acgtcaccaa gtccagaagt gtcatacacc    1740
acacctgctc caaaagatgt gctccttcct cataaaccat accctgaggt ctctcagagc    1800
gaacctgctc ctctagagac acgaggcatc ccttttatac ccatgatttc cccaagtcct    1860
agtcaagagg aactacagac cactctggaa gaaacagacc aatccaccca gaacctttc     1920 acaactaaga ttccacgaac aactgaacta gcaaagacaa ctcaggcgcc acacagattt    1980
tatactactg tgaggcccag aacatctgac aagccacaca tcagacctgg ggtcaagcaa    2040
gcacccaggc catcaggtgc tgatagaaat gtatcagtgg actctaccca ccccactaaa    2100
aagccaggga ctcgccgccc acccttgcca cccagaccta cacacccacg aagaaaacct    2160
ttaccaccaa ataatgtcac tggaaagcca ggaagtgcag gaatcatttc atcaggccca    2220
ataactacac caccctgag gtcaacaccc aggcctactg gaactcccct ggagagaata     2280
gagacagata taaagcaacc aacagttcct gcctctggag aagaactgga aaatataact    2340
gactttagct caagcccaac aagagaaact gatcctcttg ggaagccaag attcaaagga    2400
cctcatgtgc gatacatcca aaagcctgac aacagtccct gctccattac tgactctgtc    2460
aaacggttcc ccaaagagga ggccacagag gggaatgcca ccagcccacc acagaaccca    2520
cccaccaacc tcactgtggt caccgtggaa gggtgcccct catttgtcat cttggactgg    2580
gaaaagccac taaatgacac tgtcactgaa tatgaagtta tatccagaga aaatgggtca    2640
ttcagtggga agaacaagtc cattcaaatg acaaatcaga cattttccac agtagaaaat    2700
ctgaaaccaa acacgagtta tgaattccag gtgaaaccaa aaaacccgct tggtgaaggc    2760
ccggtcagca acacagtggc attcagtact gaatcagcgg acccaagagt gagtgagcca    2820
gtttctgcag gaagagatgc catctggact gaaagacccc ttaattcaga ctcttactca    2880
gagtgtaagg gcaaacaata tgtcaaaagg acatggtata aaaaatttgt aggagtgcag    2940
ctgtgcaact ctctcagata caagatttac ttgagcgact ccctcacagg aaaattttat    3000
aacataggtg atcagagggg ccatggagaa gatcactgcc agtttgtgga ttcatttta     3060 gatggacgca ctgggcagca actcacttct gaccagttac caatcaaaga aggttatttc    3120
agagcagttc gccaggaacc tgtccaattt ggagaaatag gtggtcacac ccaaatcaat    3180
tatgttcagt ggtatgaatg tgggactaca attcctggaa aatggtag                 3228
```

<210> SEQ ID NO 12
<211> LENGTH: 1075
<212> TYPE: PRT
<213> ORGANISM: human

<400> SEQUENCE: 12

```
Met Arg Gly Gly Lys Cys Asn Met Leu Ser Ser Leu Gly Cys Leu Leu
 1               5                  10                  15

Leu Cys Gly Ser Ile Thr Leu Ala Leu Gly Asn Ala Gln Lys Leu Pro
             20                  25                  30

Lys Gly Lys Arg Pro Asn Leu Lys Val His Ile Asn Thr Thr Ser Asp
         35                  40                  45

Ser Ile Leu Leu Lys Phe Leu Arg Pro Ser Pro Asn Val Lys Leu Glu
     50                  55                  60

Gly Leu Leu Leu Gly Tyr Gly Ser Asn Val Ser Pro Asn Gln Tyr Phe
 65                  70                  75                  80

Pro Leu Pro Ala Glu Gly Lys Phe Thr Glu Ala Ile Val Asp Ala Glu
                 85                  90                  95

Pro Lys Tyr Leu Ile Val Val Arg Pro Ala Pro Pro Ser Gln Lys
            100                 105                 110

Lys Ser Cys Ser Gly Lys Thr Arg Ser Arg Lys Pro Leu Gln Leu Val
            115                 120                 125

Val Gly Thr Leu Thr Pro Ser Ser Val Phe Leu Ser Trp Gly Phe Leu
    130                 135                 140

Ile Asn Pro His His Asp Trp Thr Leu Pro Ser His Cys Pro Asn Asp
145                 150                 155                 160

Arg Phe Tyr Thr Ile Arg Tyr Arg Glu Lys Asp Lys Glu Lys Lys Trp
                165                 170                 175

Ile Phe Gln Ile Cys Pro Ala Thr Glu Thr Ile Val Glu Asn Leu Lys
            180                 185                 190

Pro Asn Thr Val Tyr Glu Phe Gly Val Lys Asp Asn Val Glu Gly Gly
        195                 200                 205

Ile Trp Ser Lys Ile Phe Asn His Lys Thr Val Val Gly Ser Lys Lys
210                 215                 220

Val Asn Gly Lys Ile Gln Ser Thr Tyr Asp Gln Asp His Thr Val Pro
225                 230                 235                 240

Ala Tyr Val Pro Arg Lys Leu Ile Pro Ile Thr Ile Ile Lys Gln Val
                245                 250                 255

Ile Gln Asn Val Thr His Lys Asp Ser Ala Lys Ser Pro Glu Lys Ala
            260                 265                 270

Pro Leu Gly Gly Val Ile Leu Val His Leu Ile Ile Pro Gly Leu Asn
            275                 280                 285

Glu Thr Thr Val Lys Leu Pro Ala Ser Leu Met Phe Glu Ile Ser Asp
    290                 295                 300

Ala Leu Lys Thr Gln Leu Ala Lys Asn Glu Thr Leu Ala Leu Pro Ala
305                 310                 315                 320

Glu Ser Lys Thr Pro Glu Val Glu Lys Ile Ser Ala Arg Pro Thr Thr
                325                 330                 335

Val Thr Pro Glu Thr Val Pro Arg Ser Thr Lys Pro Thr Thr Ser Ser
            340                 345                 350

Ala Leu Asp Val Ser Glu Thr Thr Leu Ala Ser Ser Glu Lys Pro Trp
            355                 360                 365

Ile Val Pro Thr Ala Lys Ile Ser Glu Asp Ser Lys Val Leu Gln Pro
    370                 375                 380

Gln Thr Ala Thr Tyr Asp Val Phe Ser Ser Pro Thr Ser Asp Glu
385                 390                 395                 400

Pro Glu Ile Ser Asp Ser Tyr Thr Ala Thr Ser Asp Arg Ile Leu Asp
                405                 410                 415
```

```
Ser Ile Pro Pro Lys Thr Ser Arg Thr Leu Glu Gln Pro Arg Ala Thr
            420                 425                 430

Leu Ala Pro Ser Glu Thr Pro Phe Val Pro Gln Lys Leu Glu Ile Phe
            435                 440                 445

Thr Ser Pro Glu Met Gln Pro Thr Thr Pro Ala Pro Gln Gln Thr Thr
450                 455                 460

Ser Ile Pro Ser Thr Pro Lys Arg Arg Pro Arg Pro Lys Pro Pro Arg
465                 470                 475                 480

Thr Lys Pro Glu Arg Thr Thr Ser Ala Gly Thr Ile Thr Pro Lys Ile
                485                 490                 495

Ser Lys Ser Pro Glu Pro Thr Trp Thr Thr Pro Ala Pro Gly Lys Thr
                500                 505                 510

Gln Phe Ile Ser Leu Lys Pro Lys Ile Pro Leu Ser Pro Glu Val Thr
            515                 520                 525

His Thr Lys Pro Ala Pro Lys Gln Thr Pro Arg Ala Pro Pro Lys Pro
            530                 535                 540

Lys Thr Ser Pro Arg Pro Arg Ile Pro Gln Thr Gln Pro Val Pro Lys
545                 550                 555                 560

Val Pro Gln Arg Val Thr Ala Lys Pro Lys Thr Ser Pro Ser Pro Glu
                565                 570                 575

Val Ser Tyr Thr Thr Pro Ala Pro Lys Asp Val Leu Leu Pro His Lys
                580                 585                 590

Pro Tyr Pro Glu Val Ser Gln Ser Glu Pro Ala Pro Leu Glu Thr Arg
            595                 600                 605

Gly Ile Pro Phe Ile Pro Met Ile Ser Pro Ser Pro Ser Gln Glu Glu
            610                 615                 620

Leu Gln Thr Thr Leu Glu Glu Thr Asp Gln Ser Thr Gln Glu Pro Phe
625                 630                 635                 640

Thr Thr Lys Ile Pro Arg Thr Thr Glu Leu Ala Lys Thr Thr Gln Ala
                645                 650                 655

Pro His Arg Phe Tyr Thr Thr Val Arg Pro Arg Thr Ser Asp Lys Pro
                660                 665                 670

His Ile Arg Pro Gly Val Lys Gln Ala Pro Arg Pro Ser Gly Ala Asp
            675                 680                 685

Arg Asn Val Ser Val Asp Ser Thr His Pro Thr Lys Lys Pro Gly Thr
690                 695                 700

Arg Arg Pro Pro Leu Pro Arg Pro Thr His Pro Arg Arg Lys Pro
705                 710                 715                 720

Leu Pro Pro Asn Asn Val Thr Gly Lys Pro Gly Ser Ala Gly Ile Ile
                725                 730                 735

Ser Ser Gly Pro Ile Thr Thr Pro Pro Leu Arg Ser Thr Pro Arg Pro
            740                 745                 750

Thr Gly Thr Pro Leu Glu Arg Ile Glu Thr Asp Ile Lys Gln Pro Thr
            755                 760                 765

Val Pro Ala Ser Gly Glu Glu Leu Glu Asn Ile Thr Asp Phe Ser Ser
            770                 775                 780

Ser Pro Thr Arg Glu Thr Asp Pro Leu Gly Lys Pro Arg Phe Lys Gly
785                 790                 795                 800

Pro His Val Arg Tyr Ile Gln Lys Pro Asp Asn Ser Pro Cys Ser Ile
                805                 810                 815

Thr Asp Ser Val Lys Arg Phe Pro Lys Glu Glu Ala Thr Glu Gly Asn
                820                 825                 830

Ala Thr Ser Pro Pro Gln Asn Pro Pro Thr Asn Leu Thr Val Val Thr
            835                 840                 845
```

```
Val Glu Gly Cys Pro Ser Phe Val Ile Leu Asp Trp Glu Lys Pro Leu
            850                 855                 860

Asn Asp Thr Val Thr Glu Tyr Glu Val Ile Ser Arg Glu Asn Gly Ser
865                 870                 875                 880

Phe Ser Gly Lys Asn Lys Ser Ile Gln Met Thr Asn Gln Thr Phe Ser
                885                 890                 895

Thr Val Glu Asn Leu Lys Pro Asn Thr Ser Tyr Glu Phe Gln Val Lys
            900                 905                 910

Pro Lys Asn Pro Leu Gly Glu Gly Pro Val Ser Asn Thr Val Ala Phe
        915                 920                 925

Ser Thr Glu Ser Ala Asp Pro Arg Val Ser Glu Pro Val Ser Ala Gly
    930                 935                 940

Arg Asp Ala Ile Trp Thr Glu Arg Pro Phe Asn Ser Asp Ser Tyr Ser
945                 950                 955                 960

Glu Cys Lys Gly Lys Gln Tyr Val Lys Arg Thr Trp Tyr Lys Lys Phe
                965                 970                 975

Val Gly Val Gln Leu Cys Asn Ser Leu Arg Tyr Lys Ile Tyr Leu Ser
            980                 985                 990

Asp Ser Leu Thr Gly Lys Phe Tyr  Asn Ile Gly Asp Gln  Arg Gly His
        995                 1000                1005

Gly Glu  Asp His  Cys Gln Phe  Val Asp Ser Phe Leu  Asp Gly Arg
    1010                1015                1020

Thr Gly  Gln Gln Leu Thr Ser  Asp Gln Leu Pro Ile  Lys Glu Gly
    1025                1030                1035

Tyr Phe  Arg Ala Val Arg Gln  Glu Pro Val Gln Phe  Gly Glu Ile
    1040                1045                1050

Gly Gly  His Thr Gln Ile Asn  Tyr Val Gln Trp Tyr  Glu Cys Gly
    1055                1060                1065

Thr Thr  Ile Pro Gly Lys Trp
    1070                1075

<210> SEQ ID NO 13
<211> LENGTH: 1917
<212> TYPE: DNA
<213> ORGANISM: human

<400> SEQUENCE: 13
atgaagggtg gttgtgtctc ccagtggaag gcggccgccg ggttcctctt ctgtgtcatg      60
gtttttgcat ctgctgagcg accggtcttc acgaatcatt tcttgtgga gttgcataaa     120 gggggagagg acaaagctcg ccaagttgca gcagaacacg gctttggagt ccgaaagctt     180 cccttttgctg aaggtctgta ccactttttat cacaatggcc ttgcaaaggc caagagaaga     240
cgcagcctac accacaagca gcagctggag agagacccca gggtaaagat ggctttgcag     300
caggaaggat ttgaccgaaa aaagcgaggt tacagagaca tcaatgagat cgacatcaac     360
atgaacgatc tcttttttac aaagcagtgg tatctgatca atactgggca agctgatggc     420
actcctggcc ttgatttgaa tgtggctgaa gcctgggagc tgggatacac agggaaaggt     480
gttaccattg aattatgga tgatgggatt gactatctcc acccggacct ggcctccaac     540
tataatgccg aagcaagtta cgacttcagc agcaacgacc ctatcctta ccctcggtac     600 acagatgact ggtttaacag ccacgggacc cgatgtgcag agaagtttc tgctgccgcc     660 aacaacaata tctgtggagt tggagtagca tacaactcca aggttgcagg catccggatg     720
ctggaccagc cattcatgac agacatcatc gaggcctcct ccatcagtca tatgccacag     780
```

```
ctgattgaca tctacagcgc cagctggggc cccacagaca acggcaagac agtggatggg    840 cccgggag c tcacgctgca ggccatggcc gatggcgtga acaagggccg cggcggcaaa    900
ggcagcatct acgtgtgggc ctccggggac ggcggcagct atgacgactg caactgcgac    960
ggctacgcct ccagcatgtg gaccatctcc atcaactcag ccatcaacga cggcaggact   1020
gccctgtacg acgagagctg ctcttccacc ttggcttcca ccttcagcaa cgggaggaaa   1080
aggaaccccg aggccggtgt ggcaaccaca gatttgtacg gcaactgcac tctgaggcat   1140
tctgggacat ctgcagctgc ccccgaggca gctggtgtgt ttgcactggc tctggaggct   1200
aacctgggtc tgacctggcg ggacatgcag catctgactg tgctcacctc caaacggaac   1260
cagcttcacg acgaggtcca tcagtggcgg cgcaatgggg tcggcctgga atttaatcac   1320
ctctttggct acgggtcct tgatgcaggt gccatggtga aaatggctaa agactggaaa   1380
accgtgcctg agagattcca ctgtgtggga ggctccgtgc aggaccctga gaaaatacca   1440
tccactggca agttggtgct gacactcaca accgacgcct gtgaggggaa ggaaaatttt   1500
gtccgctacc tggagcatgt ccaggctgtc atcacggtca acgcaaccag aagaggagac   1560
ctgaacatca acatgacttc ccctatgggc accaagtcca ttttgctgag ccggcgtcca   1620
agggatgacg actccaaggt gggctttgac aagtggcctt catgaccac tcacacgtgg    1680 gggaagacg cccgaggcac ctggaccctg agctgggat tgtcggcag cgccccgcag   1740 aagggggtgc tgaaggagtg gaccctgatg ctgcatggca ctcagagtgc cccgtacatc   1800
gaccaggtgg tgcgggatta ccagtccaag ttggccatgt ccaagaaaga ggagctggag   1860
gaagagctgg acgaagccgt ggagagaagc ctgaaaagca tccttaacaa gaactag    1917
```

<210> SEQ ID NO 14
<211> LENGTH: 638
<212> TYPE: PRT
<213> ORGANISM: human

<400> SEQUENCE: 14

```
Met Lys Gly Gly Cys Val Ser Gln Trp Lys Ala Ala Gly Phe Leu
1               5                   10                  15

Phe Cys Val Met Val Phe Ala Ser Ala Glu Arg Pro Val Phe Thr Asn
                20                  25                  30

His Phe Leu Val Glu Leu His Lys Gly Gly Glu Asp Lys Ala Arg Gln
            35                  40                  45

Val Ala Ala Glu His Gly Phe Gly Val Arg Lys Leu Pro Phe Ala Glu
        50                  55                  60

Gly Leu Tyr His Phe Tyr His Asn Gly Leu Ala Lys Ala Lys Arg Arg
65                  70                  75                  80

Arg Ser Leu His His Lys Gln Gln Leu Glu Arg Asp Pro Arg Val Lys
                85                  90                  95

Met Ala Leu Gln Gln Glu Gly Phe Asp Arg Lys Lys Arg Gly Tyr Arg
            100                 105                 110

Asp Ile Asn Glu Ile Asp Ile Asn Met Asn Asp Pro Leu Phe Thr Lys
        115                 120                 125

Gln Trp Tyr Leu Ile Asn Thr Gly Gln Ala Asp Gly Thr Pro Gly Leu
    130                 135                 140

Asp Leu Asn Val Ala Glu Ala Trp Glu Leu Gly Tyr Thr Gly Lys Gly
145                 150                 155                 160

Val Thr Ile Gly Ile Met Asp Asp Gly Ile Asp Tyr Leu His Pro Asp
                165                 170                 175

Leu Ala Ser Asn Tyr Asn Ala Glu Ala Ser Tyr Asp Phe Ser Ser Asn
```

```
                180             185             190
Asp Pro Tyr Pro Tyr Pro Arg Tyr Thr Asp Asp Trp Phe Asn Ser His
            195             200             205
Gly Thr Arg Cys Ala Gly Glu Val Ser Ala Ala Asn Asn Asn Ile
    210             215             220
Cys Gly Val Gly Val Ala Tyr Asn Ser Lys Val Ala Gly Ile Arg Met
225             230             235             240
Leu Asp Gln Pro Phe Met Thr Asp Ile Ile Glu Ala Ser Ser Ile Ser
            245             250             255
His Met Pro Gln Leu Ile Asp Ile Tyr Ser Ala Ser Trp Gly Pro Thr
            260             265             270
Asp Asn Gly Lys Thr Val Asp Gly Pro Arg Glu Leu Thr Leu Gln Ala
            275             280             285
Met Ala Asp Gly Val Asn Lys Gly Arg Gly Lys Gly Ser Ile Tyr
    290             295             300
Val Trp Ala Ser Gly Asp Gly Gly Ser Tyr Asp Asp Cys Asn Cys Asp
305             310             315             320
Gly Tyr Ala Ser Ser Met Trp Thr Ile Ser Ile Asn Ser Ala Ile Asn
            325             330             335
Asp Gly Arg Thr Ala Leu Tyr Asp Glu Ser Cys Ser Ser Thr Leu Ala
            340             345             350
Ser Thr Phe Ser Asn Gly Arg Lys Arg Asn Pro Glu Ala Gly Val Ala
            355             360             365
Thr Thr Asp Leu Tyr Gly Asn Cys Thr Leu Arg His Ser Gly Thr Ser
    370             375             380
Ala Ala Ala Pro Glu Ala Ala Gly Val Phe Ala Leu Ala Leu Glu Ala
385             390             395             400
Asn Leu Gly Leu Thr Trp Arg Asp Met Gln His Leu Thr Val Leu Thr
            405             410             415
Ser Lys Arg Asn Gln Leu His Asp Glu Val His Gln Trp Arg Arg Asn
            420             425             430
Gly Val Gly Leu Glu Phe Asn His Leu Phe Gly Tyr Gly Val Leu Asp
            435             440             445
Ala Gly Ala Met Val Lys Met Ala Lys Asp Trp Lys Thr Val Pro Glu
            450             455             460
Arg Phe His Cys Val Gly Gly Ser Val Gln Asp Pro Glu Lys Ile Pro
465             470             475             480
Ser Thr Gly Lys Leu Val Leu Thr Leu Thr Thr Asp Ala Cys Glu Gly
            485             490             495
Lys Glu Asn Phe Val Arg Tyr Leu Glu His Val Gln Ala Val Ile Thr
            500             505             510
Val Asn Ala Thr Arg Arg Gly Asp Leu Asn Ile Asn Met Thr Ser Pro
    515             520             525
Met Gly Thr Lys Ser Ile Leu Leu Ser Arg Arg Pro Arg Asp Asp Asp
            530             535             540
Ser Lys Val Gly Phe Asp Lys Trp Pro Phe Met Thr Thr His Thr Trp
545             550             555             560
Gly Glu Asp Ala Arg Gly Thr Trp Thr Leu Glu Leu Gly Phe Val Gly
            565             570             575
Ser Ala Pro Gln Lys Gly Val Leu Lys Glu Trp Thr Leu Met Leu His
            580             585             590
Gly Thr Gln Ser Ala Pro Tyr Ile Asp Gln Val Arg Asp Tyr Gln
            595             600             605
```

-continued

| Ser | Lys | Leu | Ala | Met | Ser | Lys | Lys | Glu | Glu | Leu | Glu | Glu | Glu | Leu | Asp |
|-----|-----|-----|-----|-----|-----|-----|-----|-----|-----|-----|-----|-----|-----|-----|-----|
| 610 | | | | | 615 | | | | | 620 | | | | | |

| Glu | Ala | Val | Glu | Arg | Ser | Leu | Lys | Ser | Ile | Leu | Asn | Lys | Asn |
|-----|-----|-----|-----|-----|-----|-----|-----|-----|-----|-----|-----|-----|-----|
| 625 | | | | | 630 | | | | | 635 | | | |

<210> SEQ ID NO 15
<211> LENGTH: 8178
<212> TYPE: DNA
<213> ORGANISM: human

<400> SEQUENCE: 15

```
atggagcaaa ctgactgcaa accctaccag cctctaccaa agtcaagca tgaaatggat      60
ctagcttaca ccagttcttc tgatgagagt gaagatggaa gaaaaccaag acagtcatac    120
aactccaggg agaccctgca cgagtataac caggagctga ggatgaatta caatagccag    180
agtagaaaga ggaaagaagt agaaaaatct actcaagaga tggaattctg tgaaacctct    240
cacactctgt gctctggcta ccaaacagac atgcacagcg tttctcggca tggctaccag    300
ctagagatgg gatctgatgt ggacacagag acagaaggtg ctgcctcacc tgaccatgca    360
ctaagaatgt ggataagggg aatgaaatca gagcatagtt cctgtttgtc agccgggcc     420
aactctgcat tatccttgac tgacactgac catgaaagga agtctgatgg ggaaaatggt    480
ttcaaattct ctcctgtttg ttgtgacatg gaggctcaag ctgggtctac tcaagatgtg    540
cagagcagcc cacacaacca gttcaccttc agacccctcc accgccacc tccgcctcct    600
catgcctgca cctgtgccag gaagccaccc cctgcagcgg actctcttca gaggagatca    660
atgactaccc gcagccagcc cagcccagct gctccagctc cccaaccag cacgcaggat    720
tcagtccatc tgcataacag ctgggtcctg aacagcaaca taccattgga gaccaggcat    780
ccctgttca aacatggatc tggttcctct gcgatcttca gtgcagccag tcagaactac    840
cctctgacat ccaataccgt gtactcgccc cctcccaggc ctcttcctcg aagcaccttt    900
tcccgacctg cctttacctt taacaaacct tacaggtgct gcaactggaa gtgcacagca    960
ttgagcgcca ctgcaatcac agtgactttg gccttgttac tagcctatgt gattgcagtg   1020
catttgttcg gcctgacttg gcagttcaa ccagttgaag agagctgta tgcaaatgga    1080
gttagcaaag ggaacagggg gaccgagtcc atggacacta cttactctcc aattggagga    1140
aaagtttctg ataaatcaga gaaaaagtg tttcagaagg gacgggcgat agacactgga    1200
gaagttgaca ttggtgcaca ggtcatgcag accattccac ctggtttat ctggcgtttc    1260
cagattacta tccaccatcc aatatatctg aagttcaata tttctttagc caaggactct    1320
ctgctgggaa tttatggcag aagaaacatt ccacctacac atactcagtt tgattttgta    1380
aaactaatgg atgcaaaaca gctggtcaag caggactcca agggctctga tgatacacag    1440
cactccccctc ggaacctgat cttaacttcg cttcaggaga caggtttcat agagtatatg    1500
gatcaaggac cttggtatct ggcgttttac aatgatggaa aaaagatgga gcaagtattc    1560
gtgttaacta cagcaattga ataatggat gactgttcaa ccaattgcaa tggaaatgga    1620
gagtgtatct ctggccattg tcattgtttc ccaggattcc ttggacctga ctgtgctaga    1680
gattcctgcc ctgtgctgtg tggtgggaat ggagaatacg agaaaggaca ctgtgtctgc    1740
cggcatggct ggaaggggcc agagtgtgac gttccggaag aacaatgcat tgatccaaca    1800
tgctttggcc acggcacctg catcatggga gtctgcatct gtgtgccagg atacaaagga    1860
gaaatatgcg aggaagagga ctgcctagac ccaatgtgtt ccaaccatgg catctgtgta    1920
aaggagaat gtcactgttc tactggctgg ggaggagtta actgtgaaac accacttcct    1980
```

```
gtatgtcaag agcagtgctc aggacacgga acttttcttc tggacgctgg agtatgcagc   2040
tgtgatccca agtggacagg atctgactgc tcaacagagc tgtgtaccat ggagtgtggt   2100
agccatggag tctgctcaag aggaatttgc cagtgtgaag aaggctgggt aggaccaaca   2160
tgtgaggaac gctcctgtca ttctcattgt actgagcatg ccaatgcaa agatggaaaa    2220 tgtgagtgta gccctggatg ggagggcgac cactgcacaa ttgctcacta cttagatgct   2280
gtccgagatg gctgcccagg gctctgcttt ggaaatggac gatgtaccct ggatcaaaat   2340
ggttggcact gtgtgtgtca ggtgggttgg agtgggacag gctgcaatgt tgtcatggaa   2400
atgctttgtg gagataactt ggacaatgat ggagatggtt taaccgactg tgtggatcct   2460
gactgttgtc aacaaagcaa ctgttatata agtcctctct gccagggctc accagatcct   2520
cttgacctca ttcagcaaag ccaaactctc ttctctcagc acacttcaag acttttttat   2580
gatcgaatca aattcctcat tggcaaggac agtactcatg tcattcctcc tgaggtgtca   2640
tttgacagca ggcgtgcctg tgtgattcga ggccaagtgg tggccataga tggaactcct   2700
ctagtgggag tgaatgtcag tttcttgcac cacagtgatt atgggtttac catcagccgg   2760
caagatggaa gcttttgacct cgtggccatc ggtggcatct ctgtcatctt aatcttcgac   2820 cgatccccctt tcctgcctga agagaacca ctctggttgc cttggaatca gtttattgtg   2880
gtagagaaag tcaccatgca gagagttgta tcagacccgc catcctgcga tatctccaac   2940
tttatcagcc caaaccctat tgtgcttcct tcaccgctca catcatttgg agggtcctgt   3000
ccagagaggg gaactattgt tcctgagctg caggttgtac aggaggaaat tcccattccc   3060
tccagctttg tgaggctgag ttacctgagc agccgcaccc ctgggtataa aaccctgcta   3120
cggatccttc tgacacattc aacgattccc gtaggcatga taaaagtaca cctcacagta   3180
gctgtggaag ggcgactcac acagaagtgg tttcccgccg caattaatct tgtctacaca   3240
tttgcttgga acaagaccga tatctatgga cagaaggttt ggggcctggc agaggctttg   3300
gtatctgtgg gatatgaata tgaaacgtgc cctgacttta ttctctggga gcaaaggaca   3360
gtcgttttac aaggttttga gatggatgct tctaacctag gagactggtc tttgaataag   3420
catcacattt tgaatcctca aagtggaatc atacataaag ggaatggaga aaatatgttc   3480
atttcccagc agcccccagt catatcaacc ataatgggta atggacacca aaggagtgta   3540
gcctgcacca actgcaatgg cccagcccac aacaacaaac tctttgctcc tgtcgcctta   3600
gcttctggcc ctgatggcag tgtgtatgtt ggcgacttca attttgtaag gagaatattt   3660
ccctcgggaa actccgttag tattttggaa ttaagcacaa gtcctgctca caatactat    3720 ctggctatgg accctgtgtc tgaatcactc tatctatcag acaccaatac tcgcaaagtc   3780
tacaagttga aatctcttgt ggagacgaaa gatctgtcca agaattttga agtggtggca   3840
ggaactggtg atcagtgcct tccctttgac cagagtcatt gtggagatgg tgggagagca   3900
tcggaagctt cactgaatag ccctcgaggc atcacagttg ataggcatgg atttatttac   3960
tttgtggatg ggactatgat tcgcaaaatt gatgagaatg ctgtgatcac aactgtaatc   4020
ggctcaaatg gtctgacttc cacacaacca ctgagctgtg actcaggaat ggacatcact   4080
caggtgcgat tagagtggcc aacagacctt gcagtaaatc ctatggacaa ttcattgtat   4140
gtcttggata caacattgt gctgcaaatt tctgagaaca ggcgtgttcg gatcatcgca   4200
ggacgcccca ttcactgcca ggtgccaggc atcgatcatt tcctggtcag caaggtagca   4260
attcactcca ctctagagtc agcgagggcc atcagtgtct cccacagcgg gctgctcttc   4320
atagctgaaa cagacgagag gaaagtaaac cgcattcagc aagtaaccac caatgggag    4380
```

```
atctacatca tcgctggtgc ccccactgac tgtgactgca aaattgatcc aaactgtgac    4440 tgttttcag  gtgatggtgg ctatgccaaa gatgcaaaga tgaaagcccc ttcctcctta    4500
gcagtgtcgc ctgatggaac cctctatgtg gcagacctcg gaaatgttcg aattcgtacc   4560
atcagcagga accaagccca cctgaatgac atgaacattt atgagattgc ttcacccgct   4620
gatcaggaac tgtaccagtt cactgtaaat ggaacccacc tacacaccct gaacttgata   4680
acaagggact atgtttataa cttcacctac aattctgaag gtgacttggg cgcgattacc   4740
agcagcaatg gcaattcagt gcacattcgc cgtgatgcag gcggaatgcc gctatggctt   4800
gtggtgcctg gcggacaagt atactggctg actataagca gcaatggagt cctgaaaaga   4860
gtgtcagccc aaggctataa tccggcctta atgacctatc caggaaacac agggcttctg   4920
gctaccaaaa gtaacgaaaa tggatggaca accgtttatg agtatgaccc cgagggacac   4980
ctgaccaatg caacgtttcc cactggagag gtcagcagct ccacagtga cctggagaag    5040 ctgacaaaag tggagctaga tacttccaac cgtgaaaatg tcctcatgtc aaccaacttg   5100
acggcaacta gtaccatata tattttaaaa caagaaaata ctcaaagtac ctatcgggtg   5160
aatccagatg gttccctgcg tgtcactttt gccagcggga tggagatcgg cctcagctca   5220
gagccccaca tcctggcagg ggcagtcaac cctaccctgg gcaaatgcaa catctcattg   5280
cccggagagc acaatgcaaa cctcatcgag tggcggcaga ggaaggagca aaacaaaggc   5340
aatgtttcgg cttttgaaag gaggctgagg gcccacaaca gaaacctact ctccatagat   5400
tttgatcata aacccgcac  aggaaagatc tatgatgacc atcgaaaatt caccccttcga  5460 attctttatg accagactgg gcgacccatt ctgtggtctc ctgtaagcag atataatgaa   5520
gtgaacatca catattccacc ttcgggattg gtgacgttta ttcaaagagg aacgtggaat   5580
gaaaaaatgg aatatgacca gagtgggaaa attatttcaa gaacttgggc tgatgggaaa   5640
atttggagct ataccactt  agaaaaatct gtgatgcttc tcctacacag ccagcggcgt   5700
tacatctttg agtatgacca atcagattgc ctgctgtcag ttaccatgcc tagcatggtg   5760
cgccacagct tacaaaccat gctttcagtg ggctactacc gtaatatcta cacccccaccg   5820 gacagtagca cttcttttat ccaagactat agtcgagatg ccgattgct  acagaccctg   5880 catctgggga cagggcgcag agtcttatac aagtacacca gcaagcaag  gctttctgag   5940 gttctctatg ataccactca ggtcacatta acatatgaag agtcttctgg agtgattaag   6000
acaatacacc tgatgcatga cggattcatc tgcacaatca gatacaggca acaggacct    6060 cttattggac gccagatttt cagattcagt gaagaaggcc ttgtgaatgc acggttcgac   6120
tacagctaca acaatttccg agtcacaagc atgcaagctg taatcaatga aaccccttg    6180 cctatagatc tttaccgata tgttgatgtc tctggcagaa cagagcagtt tggaaaattc   6240
agtgtaatta attacgattt aaatcaggtc ataactacta cagtgatgaa acacaccaaa   6300
atcttcagtg ccaatggaca agtcattgaa gtccaatatg aaatcctaaa ggcaattgcc   6360
tactggatga ccattcaata tgataatgtg ggccgacatg gtaatatgtg cataagggta   6420
ggagtagatg ccaatataac aaggtacttc tatgaatacg atgctgatgg gcaacttcag   6480
actgtttctg taaatgacaa aacccagtgg cgttatagtt acgatctgaa tggagacatc   6540
aacctcttaa gccatgggaa gagtgctcgt cttactcctc tccgatatga cctccgagac   6600
cgcatcacca gattaggaga aattcagtat aaaatggatg aagatggctt tctgaggcag   6660 agggaaatg  atatttttga atataattct aatggcctgc tgcagaaagc ctacaataag   6720
gcttctggct ggactgtgca gtattactat gatgggcttt ggcgacgtgt cgcgagtaag   6780
```

```
tccagcctag ggcagcacct tcagttcttt gtcgacgcga ccgcgaaccc cataagagtt    6840
actcatttgt acaaccacac aagctcggag attacatctc tgtattatga tctccaaggt    6900
caccttattg ccatggagtt aagcagtggt gaagaatatt atgtagcctg tgataataca    6960
ggtaccccac tagctgtgtt cagcagccga ggtcaggtca taaggagat actatacaca     7020 ccttatggcg atatctatca tgacacttac cctgactttc aggtcataat tggttttcat    7080
ggaggactct atgatttcct tactaaatta gtgcacctgg gcaaaggga ttatgatgtt     7140 gttgctggca gatggacaac ggcctatcat cacatatgga aacagttgaa cctccttcct    7200
aaaccattca acctctactc ctttgaaaat aactacccag ttggcaaaat tcaagatgtt    7260
gcaaagtata ccacagacat cagaagttgg ttggagctat ttggtttcca attacacaat    7320
gtactacctg gatttcccaa acctgaatta gaaaatttag aattaactta cgagcttcta    7380
cggcttcaga caaaaactca agagtgggat cctggaaaga ctatcctggg cattcagtgt    7440
gaactccaga acagctcag gaatttcatt tccttggacc aactacctat gactccccga    7500
tacaatgatg gacggtgcct tgaaggaggg aagcaaccaa ggtttgctgc tgtcccttct    7560
gtttttggga aaggtataaa atttgccatc aaggatggca tagtaacagc tgatattata    7620
ggagtagcca atgaagatag caggcggctt gctgccattc tcaataatgc ccattacctg    7680
gaaaacctac attttaccat agaggggagg gacactcact acttcattaa gcttgggtct    7740
ctggaggaag acctggtgct catcggtaac actgggggga ggcggattct ggagaatggt    7800
gtcaatgtca ctgtgtccca gatgacttct ctgttgaatg gaggactag acggttgca     7860 gatattcagc tccagcatgg agccctgtgc ttcaacatcc ggtatgggac aactgtcgaa    7920
gaggaaaaga tcacgtgtt ggagattgcc agacagcgcg cagtggccca ggcctggact    7980
aaggaacaaa gaaggctgca agaggggaa gaggggatta gggcatggac agaaggggaa    8040
aagcagcagc ttttgagcac tgggcgggta caaggttacg atgggtattt tgttttgtct    8100
gttgagcagt atttagaact ttctgacagt gccaataata ttcactttat gagacagagc    8160
gaaataggca ggaggtaa                                                    8178
```

<210> SEQ ID NO 16
<211> LENGTH: 2725
<212> TYPE: PRT
<213> ORGANISM: human

<400> SEQUENCE: 16

```
Met Glu Gln Thr Asp Cys Lys Pro Tyr Gln Pro Leu Pro Lys Val Lys
1               5                   10                  15

His Glu Met Asp Leu Ala Tyr Thr Ser Ser Asp Glu Ser Glu Asp
            20                  25                  30

Gly Arg Lys Pro Arg Gln Ser Tyr Asn Ser Arg Glu Thr Leu His Glu
        35                  40                  45

Tyr Asn Gln Glu Leu Arg Met Asn Tyr Asn Ser Gln Ser Arg Lys Arg
    50                  55                  60

Lys Glu Val Glu Lys Ser Thr Gln Glu Met Glu Phe Cys Glu Thr Ser
65                  70                  75                  80

His Thr Leu Cys Ser Gly Tyr Gln Thr Asp Met His Ser Val Ser Arg
                85                  90                  95

His Gly Tyr Gln Leu Glu Met Gly Ser Asp Val Asp Thr Glu Thr Glu
            100                 105                 110

Gly Ala Ala Ser Pro Asp His Ala Leu Arg Met Trp Ile Arg Gly Met
        115                 120                 125
```

```
Lys Ser Glu His Ser Ser Cys Leu Ser Ser Arg Ala Asn Ser Ala Leu
130                 135                 140

Ser Leu Thr Asp Thr Asp His Glu Arg Lys Ser Asp Gly Glu Asn Gly
145                 150                 155                 160

Phe Lys Phe Ser Pro Val Cys Cys Asp Met Glu Ala Gln Ala Gly Ser
                165                 170                 175

Thr Gln Asp Val Gln Ser Ser Pro His Asn Gln Phe Thr Phe Arg Pro
                180                 185                 190

Leu Pro Pro Pro Pro Pro Pro His Ala Cys Thr Cys Ala Arg Lys
                195                 200                 205

Pro Pro Pro Ala Ala Asp Ser Leu Gln Arg Arg Ser Met Thr Thr Arg
210                 215                 220

Ser Gln Pro Ser Pro Ala Ala Pro Ala Pro Thr Ser Thr Gln Asp
225                 230                 235                 240

Ser Val His Leu His Asn Ser Trp Val Leu Asn Ser Asn Ile Pro Leu
                245                 250                 255

Glu Thr Arg His Ser Leu Phe Lys His Gly Ser Gly Ser Ser Ala Ile
                260                 265                 270

Phe Ser Ala Ala Ser Gln Asn Tyr Pro Leu Thr Ser Asn Thr Val Tyr
275                 280                 285

Ser Pro Pro Pro Arg Pro Leu Pro Arg Ser Thr Phe Ser Arg Pro Ala
290                 295                 300

Phe Thr Phe Asn Lys Pro Tyr Arg Cys Cys Asn Trp Lys Cys Thr Ala
305                 310                 315                 320

Leu Ser Ala Thr Ala Ile Thr Val Thr Leu Ala Leu Leu Leu Ala Tyr
                325                 330                 335

Val Ile Ala Val His Leu Phe Gly Leu Thr Trp Gln Leu Gln Pro Val
                340                 345                 350

Glu Gly Glu Leu Tyr Ala Asn Gly Val Ser Lys Gly Asn Arg Gly Thr
                355                 360                 365

Glu Ser Met Asp Thr Thr Tyr Ser Pro Ile Gly Gly Lys Val Ser Asp
                370                 375                 380

Lys Ser Glu Lys Lys Val Phe Gln Lys Gly Arg Ala Ile Asp Thr Gly
385                 390                 395                 400

Glu Val Asp Ile Gly Ala Gln Val Met Gln Thr Ile Pro Pro Gly Leu
                405                 410                 415

Phe Trp Arg Phe Gln Ile Thr Ile His His Pro Ile Tyr Leu Lys Phe
                420                 425                 430

Asn Ile Ser Leu Ala Lys Asp Ser Leu Leu Gly Ile Tyr Gly Arg Arg
                435                 440                 445

Asn Ile Pro Pro Thr His Thr Gln Phe Asp Phe Val Lys Leu Met Asp
                450                 455                 460

Gly Lys Gln Leu Val Lys Gln Asp Ser Lys Gly Ser Asp Asp Thr Gln
465                 470                 475                 480

His Ser Pro Arg Asn Leu Ile Leu Thr Ser Leu Gln Glu Thr Gly Phe
                485                 490                 495

Ile Glu Tyr Met Asp Gln Gly Pro Trp Tyr Leu Ala Phe Tyr Asn Asp
                500                 505                 510

Gly Lys Lys Met Glu Gln Val Phe Val Leu Thr Thr Ala Ile Glu Ile
                515                 520                 525

Met Asp Asp Cys Ser Thr Asn Cys Asn Gly Asn Gly Glu Cys Ile Ser
                530                 535                 540

Gly His Cys His Cys Phe Pro Gly Phe Leu Gly Pro Asp Cys Ala Arg
545                 550                 555                 560
```

-continued

```
Asp Ser Cys Pro Val Leu Cys Gly Gly Asn Gly Glu Tyr Glu Lys Gly
                565                 570                 575
His Cys Val Cys Arg His Gly Trp Lys Gly Pro Glu Cys Asp Val Pro
            580                 585                 590
Glu Glu Gln Cys Ile Asp Pro Thr Cys Phe Gly His Gly Thr Cys Ile
        595                 600                 605
Met Gly Val Cys Ile Cys Val Pro Gly Tyr Lys Gly Glu Ile Cys Glu
    610                 615                 620
Glu Glu Asp Cys Leu Asp Pro Met Cys Ser Asn His Gly Ile Cys Val
625                 630                 635                 640
Lys Gly Glu Cys His Cys Ser Thr Gly Trp Gly Gly Val Asn Cys Glu
                645                 650                 655
Thr Pro Leu Pro Val Cys Gln Glu Gln Cys Ser Gly His Gly Thr Phe
            660                 665                 670
Leu Leu Asp Ala Gly Val Cys Ser Cys Asp Pro Lys Trp Thr Gly Ser
        675                 680                 685
Asp Cys Ser Thr Glu Leu Cys Thr Met Glu Cys Gly Ser His Gly Val
    690                 695                 700
Cys Ser Arg Gly Ile Cys Gln Cys Glu Glu Gly Trp Val Gly Pro Thr
705                 710                 715                 720
Cys Glu Glu Arg Ser Cys His Ser His Cys Thr Glu His Gly Gln Cys
                725                 730                 735
Lys Asp Gly Lys Cys Glu Cys Ser Pro Gly Trp Glu Gly Asp His Cys
            740                 745                 750
Thr Ile Ala His Tyr Leu Asp Ala Val Arg Asp Gly Cys Pro Gly Leu
        755                 760                 765
Cys Phe Gly Asn Gly Arg Cys Thr Leu Asp Gln Asn Gly Trp His Cys
    770                 775                 780
Val Cys Gln Val Gly Trp Ser Gly Thr Gly Cys Asn Val Val Met Glu
785                 790                 795                 800
Met Leu Cys Gly Asp Asn Leu Asp Asn Asp Gly Asp Gly Leu Thr Asp
                805                 810                 815
Cys Val Asp Pro Asp Cys Cys Gln Gln Ser Asn Cys Tyr Ile Ser Pro
            820                 825                 830
Leu Cys Gln Gly Ser Pro Asp Pro Leu Asp Leu Ile Gln Gln Ser Gln
        835                 840                 845
Thr Leu Phe Ser Gln His Thr Ser Arg Leu Phe Tyr Asp Arg Ile Lys
    850                 855                 860
Phe Leu Ile Gly Lys Asp Ser Thr His Val Ile Pro Pro Glu Val Ser
865                 870                 875                 880
Phe Asp Ser Arg Arg Ala Cys Val Ile Arg Gly Gln Val Val Ala Ile
                885                 890                 895
Asp Gly Thr Pro Leu Val Gly Val Asn Val Ser Phe Leu His His Ser
            900                 905                 910
Asp Tyr Gly Phe Thr Ile Ser Arg Gln Asp Gly Ser Phe Asp Leu Val
        915                 920                 925
Ala Ile Gly Gly Ile Ser Val Ile Leu Ile Phe Asp Arg Ser Pro Phe
    930                 935                 940
Leu Pro Glu Lys Arg Thr Leu Trp Leu Pro Trp Asn Gln Phe Ile Val
945                 950                 955                 960
Val Glu Lys Val Thr Met Gln Arg Val Val Ser Asp Pro Pro Ser Cys
                965                 970                 975
Asp Ile Ser Asn Phe Ile Ser Pro Asn Pro Ile Val Leu Pro Ser Pro
```

-continued

```
                980             985              990
Leu Thr Ser Phe Gly Gly Ser Cys  Pro Glu Arg Gly Thr  Ile Val Pro
            995                  1000                 1005
Glu Leu  Gln Val Val Gln Glu  Glu Ile Pro Ile Pro  Ser Ser Phe
        1010              1015                 1020
Val Arg  Leu Ser Tyr Leu Ser  Ser Arg Thr Pro Gly  Tyr Lys Thr
        1025              1030                 1035
Leu Leu  Arg Ile Leu Leu Thr  His Ser Thr Ile Pro  Val Gly Met
        1040              1045                 1050
Ile Lys  Val His Leu Thr Val  Ala Val Glu Gly Arg  Leu Thr Gln
        1055              1060                 1065
Lys Trp  Phe Pro Ala Ala Ile  Asn Leu Val Tyr Thr  Phe Ala Trp
        1070              1075                 1080
Asn Lys  Thr Asp Ile Tyr Gly  Gln Lys Val Trp Gly  Leu Ala Glu
        1085              1090                 1095
Ala Leu  Val Ser Val Gly Tyr  Glu Tyr Glu Thr Cys  Pro Asp Phe
        1100              1105                 1110
Ile Leu  Trp Glu Gln Arg Thr  Val Val Leu Gln Gly  Phe Glu Met
        1115              1120                 1125
Asp Ala  Ser Asn Leu Gly Asp  Trp Ser Leu Asn Lys  His His Ile
        1130              1135                 1140
Leu Asn  Pro Gln Ser Gly Ile  Ile His Lys Gly Asn  Gly Glu Asn
        1145              1150                 1155
Met Phe  Ile Ser Gln Gln Pro  Pro Val Ile Ser Thr  Ile Met Gly
        1160              1165                 1170
Asn Gly  His Gln Arg Ser Val  Ala Cys Thr Asn Cys  Asn Gly Pro
        1175              1180                 1185
Ala His  Asn Asn Lys Leu Phe  Ala Pro Val Ala Leu  Ala Ser Gly
        1190              1195                 1200
Pro Asp  Gly Ser Val Tyr Val  Gly Asp Phe Asn Phe  Val Arg Arg
        1205              1210                 1215
Ile Phe  Pro Ser Gly Asn Ser  Val Ser Ile Leu Glu  Leu Ser Thr
        1220              1225                 1230
Ser Pro  Ala His Lys Tyr Tyr  Leu Ala Met Asp Pro  Val Ser Glu
        1235              1240                 1245
Ser Leu  Tyr Leu Ser Asp Thr  Asn Thr Arg Lys Val  Tyr Lys Leu
        1250              1255                 1260
Lys Ser  Leu Val Glu Thr Lys  Asp Leu Ser Lys Asn  Phe Glu Val
        1265              1270                 1275
Val Ala  Gly Thr Gly Asp Gln  Cys Leu Pro Phe Asp  Gln Ser His
        1280              1285                 1290
Cys Gly  Asp Gly Gly Arg Ala  Ser Glu Ala Ser Leu  Asn Ser Pro
        1295              1300                 1305
Arg Gly  Ile Thr Val Asp Arg  His Gly Phe Ile Tyr  Phe Val Asp
        1310              1315                 1320
Gly Thr  Met Ile Arg Lys Ile  Asp Glu Asn Ala Val  Ile Thr Thr
        1325              1330                 1335
Val Ile  Gly Ser Asn Gly Leu  Thr Ser Thr Gln Pro  Leu Ser Cys
        1340              1345                 1350
Asp Ser  Gly Met Asp Ile Thr  Gln Val Arg Leu Glu  Trp Pro Thr
        1355              1360                 1365
Asp Leu  Ala Val Asn Pro Met  Asp Asn Ser Leu Tyr  Val Leu Asp
        1370              1375                 1380
```

-continued

```
Asn Asn Ile Val Leu Gln Ile Ser Glu Asn Arg Arg Val Arg Ile
    1385                1390                1395

Ile Ala Gly Arg Pro Ile His Cys Gln Val Pro Gly Ile Asp His
    1400                1405                1410

Phe Leu Val Ser Lys Val Ala Ile His Ser Thr Leu Glu Ser Ala
    1415                1420                1425

Arg Ala Ile Ser Val Ser His Ser Gly Leu Leu Phe Ile Ala Glu
    1430                1435                1440

Thr Asp Glu Arg Lys Val Asn Arg Ile Gln Gln Val Thr Thr Asn
    1445                1450                1455

Gly Glu Ile Tyr Ile Ile Ala Gly Ala Pro Thr Asp Cys Asp Cys
    1460                1465                1470

Lys Ile Asp Pro Asn Cys Asp Cys Phe Ser Gly Asp Gly Gly Tyr
    1475                1480                1485

Ala Lys Asp Ala Lys Met Lys Ala Pro Ser Ser Leu Ala Val Ser
    1490                1495                1500

Pro Asp Gly Thr Leu Tyr Val Ala Asp Leu Gly Asn Val Arg Ile
    1505                1510                1515

Arg Thr Ile Ser Arg Asn Gln Ala His Leu Asn Asp Met Asn Ile
    1520                1525                1530

Tyr Glu Ile Ala Ser Pro Ala Asp Gln Glu Leu Tyr Gln Phe Thr
    1535                1540                1545

Val Asn Gly Thr His Leu His Thr Leu Asn Leu Ile Thr Arg Asp
    1550                1555                1560

Tyr Val Tyr Asn Phe Thr Tyr Asn Ser Glu Gly Asp Leu Gly Ala
    1565                1570                1575

Ile Thr Ser Ser Asn Gly Asn Ser Val His Ile Arg Arg Asp Ala
    1580                1585                1590

Gly Gly Met Pro Leu Trp Leu Val Val Pro Gly Gly Gln Val Tyr
    1595                1600                1605

Trp Leu Thr Ile Ser Ser Asn Gly Val Leu Lys Arg Val Ser Ala
    1610                1615                1620

Gln Gly Tyr Asn Pro Ala Leu Met Thr Tyr Pro Gly Asn Thr Gly
    1625                1630                1635

Leu Leu Ala Thr Lys Ser Asn Glu Asn Gly Trp Thr Thr Val Tyr
    1640                1645                1650

Glu Tyr Asp Pro Glu Gly His Leu Thr Asn Ala Thr Phe Pro Thr
    1655                1660                1665

Gly Glu Val Ser Ser Phe His Ser Asp Leu Glu Lys Leu Thr Lys
    1670                1675                1680

Val Glu Leu Asp Thr Ser Asn Arg Glu Asn Val Leu Met Ser Thr
    1685                1690                1695

Asn Leu Thr Ala Thr Ser Thr Ile Tyr Ile Leu Lys Gln Glu Asn
    1700                1705                1710

Thr Gln Ser Thr Tyr Arg Val Asn Pro Asp Gly Ser Leu Arg Val
    1715                1720                1725

Thr Phe Ala Ser Gly Met Glu Ile Gly Leu Ser Ser Glu Pro His
    1730                1735                1740

Ile Leu Ala Gly Ala Val Asn Pro Thr Leu Gly Lys Cys Asn Ile
    1745                1750                1755

Ser Leu Pro Gly Glu His Asn Ala Asn Leu Ile Glu Trp Arg Gln
    1760                1765                1770

Arg Lys Glu Gln Asn Lys Gly Asn Val Ser Ala Phe Glu Arg Arg
    1775                1780                1785
```

```
Leu Arg Ala His Asn Arg Asn Leu Leu Ser Ile Asp Phe Asp His
    1790            1795                1800

Ile Thr Arg Thr Gly Lys Ile Tyr Asp Asp His Arg Lys Phe Thr
    1805            1810                1815

Leu Arg Ile Leu Tyr Asp Gln Thr Gly Arg Pro Ile Leu Trp Ser
    1820            1825                1830

Pro Val Ser Arg Tyr Asn Glu Val Asn Ile Thr Tyr Ser Pro Ser
    1835            1840                1845

Gly Leu Val Thr Phe Ile Gln Arg Gly Thr Trp Asn Glu Lys Met
    1850            1855                1860

Glu Tyr Asp Gln Ser Gly Lys Ile Ile Ser Arg Thr Trp Ala Asp
    1865            1870                1875

Gly Lys Ile Trp Ser Tyr Thr Tyr Leu Glu Lys Ser Val Met Leu
    1880            1885                1890

Leu Leu His Ser Gln Arg Arg Tyr Ile Phe Glu Tyr Asp Gln Ser
    1895            1900                1905

Asp Cys Leu Leu Ser Val Thr Met Pro Ser Met Val Arg His Ser
    1910            1915                1920

Leu Gln Thr Met Leu Ser Val Gly Tyr Tyr Arg Asn Ile Tyr Thr
    1925            1930                1935

Pro Pro Asp Ser Ser Thr Ser Phe Ile Gln Asp Tyr Ser Arg Asp
    1940            1945                1950

Gly Arg Leu Leu Gln Thr Leu His Leu Gly Thr Gly Arg Arg Val
    1955            1960                1965

Leu Tyr Lys Tyr Thr Lys Gln Ala Arg Leu Ser Glu Val Leu Tyr
    1970            1975                1980

Asp Thr Thr Gln Val Thr Leu Thr Tyr Glu Glu Ser Ser Gly Val
    1985            1990                1995

Ile Lys Thr Ile His Leu Met His Asp Gly Phe Ile Cys Thr Ile
    2000            2005                2010

Arg Tyr Arg Gln Thr Gly Pro Leu Ile Gly Arg Gln Ile Phe Arg
    2015            2020                2025

Phe Ser Glu Glu Gly Leu Val Asn Ala Arg Phe Asp Tyr Ser Tyr
    2030            2035                2040

Asn Asn Phe Arg Val Thr Ser Met Gln Ala Val Ile Asn Glu Thr
    2045            2050                2055

Pro Leu Pro Ile Asp Leu Tyr Arg Tyr Val Asp Val Ser Gly Arg
    2060            2065                2070

Thr Glu Gln Phe Gly Lys Phe Ser Val Ile Asn Tyr Asp Leu Asn
    2075            2080                2085

Gln Val Ile Thr Thr Thr Val Met Lys His Thr Lys Ile Phe Ser
    2090            2095                2100

Ala Asn Gly Gln Val Ile Glu Val Gln Tyr Glu Ile Leu Lys Ala
    2105            2110                2115

Ile Ala Tyr Trp Met Thr Ile Gln Tyr Asp Asn Val Gly Arg His
    2120            2125                2130

Gly Asn Met Cys Ile Arg Val Gly Val Asp Ala Asn Ile Thr Arg
    2135            2140                2145

Tyr Phe Tyr Glu Tyr Asp Ala Asp Gly Gln Leu Gln Thr Val Ser
    2150            2155                2160

Val Asn Asp Lys Thr Gln Trp Arg Tyr Ser Tyr Asp Leu Asn Gly
    2165            2170                2175

Asp Ile Asn Leu Leu Ser His Gly Lys Ser Ala Arg Leu Thr Pro
```

```
                        2180                2185                2190
Leu Arg Tyr Asp Leu Arg Asp Arg Ile Thr Arg Leu Gly Glu Ile
    2195                2200                2205
Gln Tyr Lys Met Asp Glu Asp Gly Phe Leu Arg Gln Arg Gly Asn
    2210                2215                2220
Asp Ile Phe Glu Tyr Asn Ser Asn Gly Leu Leu Gln Lys Ala Tyr
    2225                2230                2235
Asn Lys Ala Ser Gly Trp Thr Val Gln Tyr Tyr Asp Gly Leu
    2240                2245                2250
Gly Arg Arg Val Ala Ser Lys Ser Ser Leu Gly Gln His Leu Gln
    2255                2260                2265
Phe Phe Val Asp Ala Thr Ala Asn Pro Ile Arg Val Thr His Leu
    2270                2275                2280
Tyr Asn His Thr Ser Ser Glu Ile Thr Ser Leu Tyr Tyr Asp Leu
    2285                2290                2295
Gln Gly His Leu Ile Ala Met Glu Leu Ser Ser Gly Glu Glu Tyr
    2300                2305                2310
Tyr Val Ala Cys Asp Asn Thr Gly Thr Pro Leu Ala Val Phe Ser
    2315                2320                2325
Ser Arg Gly Gln Val Ile Lys Glu Ile Leu Tyr Thr Pro Tyr Gly
    2330                2335                2340
Asp Ile Tyr His Asp Thr Tyr Pro Asp Phe Gln Val Ile Ile Gly
    2345                2350                2355
Phe His Gly Gly Leu Tyr Asp Phe Leu Thr Lys Leu Val His Leu
    2360                2365                2370
Gly Gln Arg Asp Tyr Asp Val Val Ala Gly Arg Trp Thr Thr Ala
    2375                2380                2385
Tyr His His Ile Trp Lys Gln Leu Asn Leu Leu Pro Lys Pro Phe
    2390                2395                2400
Asn Leu Tyr Ser Phe Glu Asn Asn Tyr Pro Val Gly Lys Ile Gln
    2405                2410                2415
Asp Val Ala Lys Tyr Thr Thr Asp Ile Arg Ser Trp Leu Glu Leu
    2420                2425                2430
Phe Gly Phe Gln Leu His Asn Val Leu Pro Gly Phe Pro Lys Pro
    2435                2440                2445
Glu Leu Glu Asn Leu Glu Leu Thr Tyr Glu Leu Leu Arg Leu Gln
    2450                2455                2460
Thr Lys Thr Gln Glu Trp Asp Pro Gly Lys Thr Ile Leu Gly Ile
    2465                2470                2475
Gln Cys Glu Leu Gln Lys Gln Leu Arg Asn Phe Ile Ser Leu Asp
    2480                2485                2490
Gln Leu Pro Met Thr Pro Arg Tyr Asn Asp Gly Arg Cys Leu Glu
    2495                2500                2505
Gly Gly Lys Gln Pro Arg Phe Ala Ala Val Pro Ser Val Phe Gly
    2510                2515                2520
Lys Gly Ile Lys Phe Ala Ile Lys Asp Gly Ile Val Thr Ala Asp
    2525                2530                2535
Ile Ile Gly Val Ala Asn Glu Asp Ser Arg Arg Leu Ala Ala Ile
    2540                2545                2550
Leu Asn Asn Ala His Tyr Leu Glu Asn Leu His Phe Thr Ile Glu
    2555                2560                2565
Gly Arg Asp Thr His Tyr Phe Ile Lys Leu Gly Ser Leu Glu Glu
    2570                2575                2580
```

```
Asp Leu Val Leu Ile Gly Asn Thr Gly Gly Arg Arg Ile Leu Glu
        2585                2590                2595

Asn Gly Val Asn Val Thr Val Ser Gln Met Thr Ser Leu Leu Asn
2600                2605                2610

Gly Arg Thr Arg Arg Phe Ala Asp Ile Gln Leu Gln His Gly Ala
        2615                2620                2625

Leu Cys Phe Asn Ile Arg Tyr Gly Thr Thr Val Glu Glu Glu Lys
    2630                2635                2640

Asn His Val Leu Glu Ile Ala Arg Gln Arg Ala Val Ala Gln Ala
2645                2650                2655

Trp Thr Lys Glu Gln Arg Arg Leu Gln Glu Gly Glu Glu Gly Ile
        2660                2665                2670

Arg Ala Trp Thr Glu Gly Glu Lys Gln Gln Leu Leu Ser Thr Gly
    2675                2680                2685

Arg Val Gln Gly Tyr Asp Gly Tyr Phe Val Leu Ser Val Glu Gln
2690                2695                2700

Tyr Leu Glu Leu Ser Asp Ser Ala Asn Asn Ile His Phe Met Arg
        2705                2710                2715

Gln Ser Glu Ile Gly Arg Arg
    2720                2725

<210> SEQ ID NO 17
<211> LENGTH: 1083
<212> TYPE: DNA
<213> ORGANISM: human

<400> SEQUENCE: 17
atgatcccgc tgctgctggc agcgctgctg tgcgtccccg ccggggccct gacctgctac     60
ggggactccg ggcagcctgt agactggttc gtggtctaca agctgccagc tcttagaggg    120
tccggggagg cggcgcagag agggctgcag tacaagtatc tggacgagag ctccggaggc    180
tggcgggacg gcagggcact catcaacagc ccggaggggg ccgtgggccg aagcctgcag    240
ccgctgtacc ggagcaacac cagccagctc gccttcctgc tctacaatga ccaaccgcct    300
caacccagca aggctcagga ctcttccatg cgtgggcaca cgaagggtgt cctgctcctt    360
gaccacgatg ggggcttctg gctggtccac agtgtaccta acttccctcc accggcctcc    420
tctgctgcat acagctggcc tcatagcgcc tgtacctacg gcagaccct gctctgtgtg     480
tcttttccct tcgctcagtt ctcgaagatg ggcaagcagc tgacctacac ctaccccctgg   540
gtctataact accagctgga aaggatcttt gccccaggaat tccccgactt ggagaatgtg   600
gtcaagggcc accacgttag ccaagaaccc tggaacagca gcatcacact cacatcccag   660
gccgggggctg ttttccagag ctttgccaag ttcagcaaat ttggagatga cctgtactcc   720
ggctggttgg cagcagccct tggtaccaac ctgcaggtcc agttctggca caaaactgta   780
ggcatcctgc cctctaactg ctcggatatc tggcaggttc tgaatgtgaa ccagatagct   840
ttccctggac cagccggccc aagcttcaac agcacagagg accactccaa atggtgcgtg   900
tccccaaaag ggccctggac ctgcgtgggt gacatgaatc ggaaccaggg agaggagcaa   960
cggggtgggg gcacactgtg tgcccagctg ccagccctct ggaaagcctt ccagccgctg  1020
gtgaagaact accagccctg taatggcatg gccaggaagc ccagcagagc ttataagatc  1080
taa                                                                 1083

<210> SEQ ID NO 18
<211> LENGTH: 360
<212> TYPE: PRT
```

<213> ORGANISM: human

<400> SEQUENCE: 18

```
Met Ile Pro Leu Leu Leu Ala Ala Leu Leu Cys Val Pro Gly Ala
1               5                   10                  15

Leu Thr Cys Tyr Gly Asp Ser Gly Gln Pro Val Asp Trp Phe Val Val
            20                  25                  30

Tyr Lys Leu Pro Ala Leu Arg Gly Ser Gly Glu Ala Ala Gln Arg Gly
            35                  40                  45

Leu Gln Tyr Lys Tyr Leu Asp Glu Ser Gly Gly Trp Arg Asp Gly
    50                  55                  60

Arg Ala Leu Ile Asn Ser Pro Glu Gly Ala Val Gly Arg Ser Leu Gln
65                  70                  75                  80

Pro Leu Tyr Arg Ser Asn Thr Ser Gln Leu Ala Phe Leu Leu Tyr Asn
                85                  90                  95

Asp Gln Pro Pro Gln Pro Ser Lys Ala Gln Asp Ser Ser Met Arg Gly
            100                 105                 110

His Thr Lys Gly Val Leu Leu Leu Asp His Asp Gly Gly Phe Trp Leu
            115                 120                 125

Val His Ser Val Pro Asn Phe Pro Pro Ala Ser Ser Ala Ala Tyr
    130                 135                 140

Ser Trp Pro His Ser Ala Cys Thr Tyr Gly Gln Thr Leu Leu Cys Val
145                 150                 155                 160

Ser Phe Pro Phe Ala Gln Phe Ser Lys Met Gly Lys Gln Leu Thr Tyr
                165                 170                 175

Thr Tyr Pro Trp Val Tyr Asn Tyr Gln Leu Glu Gly Ile Phe Ala Gln
            180                 185                 190

Glu Phe Pro Asp Leu Glu Asn Val Val Lys Gly His His Val Ser Gln
        195                 200                 205

Glu Pro Trp Asn Ser Ser Ile Thr Leu Thr Ser Gln Ala Gly Ala Val
    210                 215                 220

Phe Gln Ser Phe Ala Lys Phe Ser Lys Phe Gly Asp Asp Leu Tyr Ser
225                 230                 235                 240

Gly Trp Leu Ala Ala Ala Leu Gly Thr Asn Leu Gln Val Gln Phe Trp
                245                 250                 255

His Lys Thr Val Gly Ile Leu Pro Ser Asn Cys Ser Asp Ile Trp Gln
            260                 265                 270

Val Leu Asn Val Asn Gln Ile Ala Phe Pro Gly Pro Ala Gly Pro Ser
        275                 280                 285

Phe Asn Ser Thr Glu Asp His Ser Lys Trp Cys Val Ser Pro Lys Gly
290                 295                 300

Pro Trp Thr Cys Val Gly Asp Met Asn Arg Asn Gln Gly Glu Glu Gln
305                 310                 315                 320

Arg Gly Gly Gly Thr Leu Cys Ala Gln Leu Pro Ala Leu Trp Lys Ala
                325                 330                 335

Phe Gln Pro Leu Val Lys Asn Tyr Gln Pro Cys Asn Gly Met Ala Arg
            340                 345                 350

Lys Pro Ser Arg Ala Tyr Lys Ile
            355                 360
```

<210> SEQ ID NO 19
<211> LENGTH: 2094
<212> TYPE: DNA
<213> ORGANISM: human

<400> SEQUENCE: 19

```
atgtgtaaat cactgcgtta ttgctttagt cattgtctct atttagcaat gacaagactg      60
gaagaagtaa atagagaagt gaacatgcat tcttcagtgc ggtatcttgg ctatttagcc     120
agaatcaatt tattggttgc tatatgctta ggtctatacg taagatggga aaaaacagca     180
aattccttaa ttttggtaat ttttattctt ggtctttttg ttcttggaat cgccagcata     240
ctctattact atttttcaat ggaagcagca agtttaagtc tctccaatct ttggtttgga     300
ttcttgcttg gcctcctatg ttttcttgat aattcatcct ttaaaaatga tgtaaaagaa     360
gaatcaacca atatttgct tctaacatcc atagtgttaa ggatattgtg ctctctggtg      420
gagagaattt ctggctatgt ccgtcatcgg cccactttac taaccacagt tgaatttctg     480
gagcttgttg gatttgccat tgccagcaca actatgttgg tggagaagtc tctgagtgtc     540
attttgcttg ttgtagctct ggctatgctg attattgatc tgagaatgaa atctttctta     600
gctattccaa acttagttat ttttgcagtt ttgttatttt tttcctcatt ggaaactccc     660
aaaaatccga ttgcttttgc gtgttttttt atttgcctga taactgatcc tttccttgac     720
atttatttta gtggactttc agtaactgaa agatggaaac cttttttgta ccgtggaaga     780
atttgcagaa gactttcagt cgttttgct ggaatgattg agcttacatt ttttattctt     840
tccgcattca aacttagaga cactcacctc tggtattttg taatacctgg cttttccatt     900
tttgaatttt tcaggatgat ttgtcatatt ttttttcttt taactctttg gggattccat     960
accaaattaa atgactgcca taaagtatat tttactcaca ggacagatta caatagcctt    1020
gatagaatca tggcatccaa agggatgcgc cattttttgct tgatttcaga gcagttggtg   1080
ttctttagtc ttcttgcaac agcgattttg ggagcagttt cctggcagcc aacaaatgga   1140
attttcttga gcatgttcct aatcgttttg ccattggaat ccatggctca tgggctcttc   1200
catgaattgg gtaactgttt aggaggaaca tctgttggat atgctattgt gattcccacc   1260
aacttctgca gtcctgatgg tcagccaaca ctgcttcccc cagaacatgt acaggagtta   1320
aatttgaggt ctactggcat gctcaatgct atccaaagat ttttttgcata tcatatgatt  1380 gagacctatg gatgtgacta ttccacaagt ggactgtcat tgatactct gcattccaaa    1440 ctaaaagctt tcctcgaact tcggacagtg gatggaccca gacatgatac gtatattttg    1500
tattacagtg gcacaccca tggtacagga gagtgggctc tagcaggtgg agatacacta    1560
cgccttgaca cacttataga atggtggaga gaaaagaatg gttccttttg ttcccggctt    1620
attatcgtat tagacagcga aaattcaacc ccttgggtga agaagtgag gaaaattaat     1680 gaccagtata ttgcagtgca aggagcagag ttgataaaaa cagtagatat tgaagaagct   1740
gacccgccac agctaggtga ctttacaaaa gactgggtag aatataactg caactcctgt   1800
aataacatct gctggactga aagggacgc acagtgaaag cagtatatgg tgtgtcaaaa     1860
cggtggagtg actacactct gcatttgcca acgggaagcg atgtggccaa gcactggatg   1920
ttacactttc ctcgtattac atatccccta gtgcatttgg caaattggtt atgcggtctg    1980
aacctttttt ggatctgcaa aacttgtttt aggtgcttga aagattaaa aatgagttgg     2040 tttcttccta ctgtgctgga cacaggacaa ggcttcaaac ttgtcaaatc ttaa          2094
```

<210> SEQ ID NO 20
<211> LENGTH: 697
<212> TYPE: PRT
<213> ORGANISM: human

<400> SEQUENCE: 20

Met Cys Lys Ser Leu Arg Tyr Cys Phe Ser His Cys Leu Tyr Leu Ala

-continued

```
1               5                   10                  15
Met Thr Arg Leu Glu Glu Val Asn Arg Glu Val Asn Met His Ser Ser
                20                  25                  30

Val Arg Tyr Leu Gly Tyr Leu Ala Arg Ile Asn Leu Leu Val Ala Ile
                35                  40                  45

Cys Leu Gly Leu Tyr Val Arg Trp Glu Lys Thr Ala Asn Ser Leu Ile
        50                  55                  60

Leu Val Ile Phe Ile Leu Gly Leu Phe Val Leu Gly Ile Ala Ser Ile
65                  70                  75                  80

Leu Tyr Tyr Tyr Phe Ser Met Glu Ala Ala Ser Leu Ser Leu Ser Asn
                    85                  90                  95

Leu Trp Phe Gly Phe Leu Leu Gly Leu Leu Cys Phe Leu Asp Asn Ser
                100                 105                 110

Ser Phe Lys Asn Asp Val Lys Glu Ser Thr Lys Tyr Leu Leu Leu
            115                 120                 125

Thr Ser Ile Val Leu Arg Ile Leu Cys Ser Leu Val Glu Arg Ile Ser
        130                 135                 140

Gly Tyr Val Arg His Arg Pro Thr Leu Leu Thr Thr Val Glu Phe Leu
145                 150                 155                 160

Glu Leu Val Gly Phe Ala Ile Ala Ser Thr Thr Met Leu Val Glu Lys
                165                 170                 175

Ser Leu Ser Val Ile Leu Leu Val Val Ala Leu Ala Met Leu Ile Ile
                180                 185                 190

Asp Leu Arg Met Lys Ser Phe Leu Ala Ile Pro Asn Leu Val Ile Phe
                195                 200                 205

Ala Val Leu Leu Phe Phe Ser Ser Leu Glu Thr Pro Lys Asn Pro Ile
        210                 215                 220

Ala Phe Ala Cys Phe Phe Ile Cys Leu Ile Thr Asp Pro Phe Leu Asp
225                 230                 235                 240

Ile Tyr Phe Ser Gly Leu Ser Val Thr Glu Arg Trp Lys Pro Phe Leu
                245                 250                 255

Tyr Arg Gly Arg Ile Cys Arg Arg Leu Ser Val Val Phe Ala Gly Met
                260                 265                 270

Ile Glu Leu Thr Phe Phe Ile Leu Ser Ala Phe Lys Leu Arg Asp Thr
        275                 280                 285

His Leu Trp Tyr Phe Val Ile Pro Gly Phe Ser Ile Phe Gly Ile Phe
        290                 295                 300

Arg Met Ile Cys His Ile Ile Phe Leu Leu Thr Leu Trp Gly Phe His
305                 310                 315                 320

Thr Lys Leu Asn Asp Cys His Lys Val Tyr Phe Thr His Arg Thr Asp
                325                 330                 335

Tyr Asn Ser Leu Asp Arg Ile Met Ala Ser Lys Gly Met Arg His Phe
                340                 345                 350

Cys Leu Ile Ser Glu Gln Leu Val Phe Phe Ser Leu Leu Ala Thr Ala
                355                 360                 365

Ile Leu Gly Ala Val Ser Trp Gln Pro Thr Asn Gly Ile Phe Leu Ser
        370                 375                 380

Met Phe Leu Ile Val Leu Pro Leu Glu Ser Met Ala His Gly Leu Phe
385                 390                 395                 400

His Glu Leu Gly Asn Cys Leu Gly Gly Thr Ser Val Gly Tyr Ala Ile
                405                 410                 415

Val Ile Pro Thr Asn Phe Cys Ser Pro Asp Gly Gln Pro Thr Leu Leu
                420                 425                 430
```

```
Pro Pro Glu His Val Gln Glu Leu Asn Leu Arg Ser Thr Gly Met Leu
        435                 440                 445

Asn Ala Ile Gln Arg Phe Phe Ala Tyr His Met Ile Glu Thr Tyr Gly
    450                 455                 460

Cys Asp Tyr Ser Thr Ser Gly Leu Ser Phe Asp Thr Leu His Ser Lys
465                 470                 475                 480

Leu Lys Ala Phe Leu Glu Leu Arg Thr Val Asp Gly Pro Arg His Asp
                485                 490                 495

Thr Tyr Ile Leu Tyr Tyr Ser Gly His Thr His Gly Thr Gly Glu Trp
            500                 505                 510

Ala Leu Ala Gly Gly Asp Thr Leu Arg Leu Asp Thr Leu Ile Glu Trp
        515                 520                 525

Trp Arg Glu Lys Asn Gly Ser Phe Cys Ser Arg Leu Ile Ile Val Leu
    530                 535                 540

Asp Ser Glu Asn Ser Thr Pro Trp Val Lys Glu Val Arg Lys Ile Asn
545                 550                 555                 560

Asp Gln Tyr Ile Ala Val Gln Gly Ala Glu Leu Ile Lys Thr Val Asp
                565                 570                 575

Ile Glu Glu Ala Asp Pro Pro Gln Leu Gly Asp Phe Thr Lys Asp Trp
            580                 585                 590

Val Glu Tyr Asn Cys Asn Ser Cys Asn Asn Ile Cys Trp Thr Glu Lys
        595                 600                 605

Gly Arg Thr Val Lys Ala Val Tyr Gly Val Ser Lys Arg Trp Ser Asp
    610                 615                 620

Tyr Thr Leu His Leu Pro Thr Gly Ser Asp Val Ala Lys His Trp Met
625                 630                 635                 640

Leu His Phe Pro Arg Ile Thr Tyr Pro Leu Val His Leu Ala Asn Trp
                645                 650                 655

Leu Cys Gly Leu Asn Leu Phe Trp Ile Cys Lys Thr Cys Phe Arg Cys
            660                 665                 670

Leu Lys Arg Leu Lys Met Ser Trp Phe Leu Pro Thr Val Leu Asp Thr
        675                 680                 685

Gly Gln Gly Phe Lys Leu Val Lys Ser
    690                 695

<210> SEQ ID NO 21
<211> LENGTH: 1236
<212> TYPE: DNA
<213> ORGANISM: human

<400> SEQUENCE: 21
atgaaggcgg cccgcttcgt gctgcgcagc gctggctcgc tcaacggcgc cggcctggtg        60
ccccgagagg tggagcattt ctcgcgctac agcccgtccc cgctgtccat gaagcagcta       120
ctggactttg ttcagaaaaa tgcatgtgaa agaacttctt ttgcattttt gcgacaagaa       180
ttgcctgtga gactcgccaa cattctgaag gaaattgata cctcccgac ccaattagta       240 aatacctctt cagtgcaatt ggttaaaagc tggtatatac agagcctgat ggatttggtg       300
gaattccatg agaaaagccc agatgaccag aaagcattat cagactttgt agatacactc       360
atcaaagttc gaaatagaca ccataatgta gtccctacaa tggcacaagg aatcatagag       420
tataaagatg cctgtacagt tgacccagtc accaatcaaa tcttcaata tttcttggat       480 cgatttttaca tgaaccgtat ttctactcgg atgctgatga accagcacat tcttatattt       540
agtgactcac agacaggaaa cccaagccac attgaagca ttgatcctaa ctgtgatgtg       600
gtagcagtgg tccaagatgc ctttgagtgt tcaaggatgc tctgtgatca gtattattta       660
```

```
tcatctccag aattaaagct tacacaagtg aatggaaaat ttccagacca accaattcac      720
atcgtgtatg ttccttctca cctccatcat atgctctttg aactatttaa gaatgcaatg      780
cgggcaacag ttgaacacca ggaaaatcag ccttccctta caccaataga ggttattgtt      840
gtcttgggaa aagaagacct taccattaag atttcagaca gaggaggtgg tgttcccctg      900
agaattattg accgcctctt tagttataca tactccactg caccaacgcc tgtgatggat      960
aattcccgga atgctccttt ggctggtttt ggttacggct tgccaatttc tcgtctgtat     1020
gccaagtact ttcaaggaga tctgaatctc tactctttat caggatatgg aacagatgct     1080
atcatctact taaaggcttt gtcttctgag tctatagaaa aacttccagt ttttaacaag     1140
tcagccttca acattatca gatgagctct gaggctgatg actggtgtat cccaagcagg     1200
gaaccaaaga acctggcaaa agaagtggcc atgtga                              1236
```

<210> SEQ ID NO 22
<211> LENGTH: 411
<212> TYPE: PRT
<213> ORGANISM: human

<400> SEQUENCE: 22

```
Met Lys Ala Ala Arg Phe Val Leu Arg Ser Ala Gly Ser Leu Asn Gly
1               5                   10                  15

Ala Gly Leu Val Pro Arg Glu Val Glu His Phe Ser Arg Tyr Ser Pro
            20                  25                  30

Ser Pro Leu Ser Met Lys Gln Leu Leu Asp Phe Gly Ser Glu Asn Ala
        35                  40                  45

Cys Glu Arg Thr Ser Phe Ala Phe Leu Arg Gln Glu Leu Pro Val Arg
    50                  55                  60

Leu Ala Asn Ile Leu Lys Glu Ile Asp Ile Leu Pro Thr Gln Leu Val
65                  70                  75                  80

Asn Thr Ser Ser Val Gln Leu Val Lys Ser Trp Tyr Ile Gln Ser Leu
                85                  90                  95

Met Asp Leu Val Glu Phe His Glu Lys Ser Pro Asp Asp Gln Lys Ala
            100                 105                 110

Leu Ser Asp Phe Val Asp Thr Leu Ile Lys Val Arg Asn Arg His His
        115                 120                 125

Asn Val Val Pro Thr Met Ala Gln Gly Ile Ile Glu Tyr Lys Asp Ala
    130                 135                 140

Cys Thr Val Asp Pro Val Thr Asn Gln Asn Leu Gln Tyr Phe Leu Asp
145                 150                 155                 160

Arg Phe Tyr Met Asn Arg Ile Ser Thr Arg Met Leu Met Asn Gln His
                165                 170                 175

Ile Leu Ile Phe Ser Asp Ser Gln Thr Gly Asn Pro Ser His Ile Gly
            180                 185                 190

Ser Ile Asp Pro Asn Cys Asp Val Val Ala Val Gln Asp Ala Phe
        195                 200                 205

Glu Cys Ser Arg Met Leu Cys Asp Gln Tyr Tyr Leu Ser Ser Pro Glu
    210                 215                 220

Leu Lys Leu Thr Gln Val Asn Gly Lys Phe Pro Asp Gln Pro Ile His
225                 230                 235                 240

Ile Val Tyr Val Pro Ser His Leu His His Met Leu Phe Glu Leu Phe
                245                 250                 255

Lys Asn Ala Met Arg Ala Thr Val Glu His Gln Glu Asn Gln Pro Ser
            260                 265                 270
```

```
Leu Thr Pro Ile Glu Val Ile Val Leu Gly Lys Glu Asp Leu Thr
        275                 280                 285

Ile Lys Ile Ser Asp Arg Gly Gly Val Pro Leu Arg Ile Ile Asp
    290                 295                 300

Arg Leu Phe Ser Tyr Thr Tyr Ser Thr Ala Pro Thr Pro Val Met Asp
305                 310                 315                 320

Asn Ser Arg Asn Ala Pro Leu Ala Gly Phe Gly Tyr Gly Leu Pro Ile
                325                 330                 335

Ser Arg Leu Tyr Ala Lys Tyr Phe Gln Gly Asp Leu Asn Leu Tyr Ser
            340                 345                 350

Leu Ser Gly Tyr Gly Thr Asp Ala Ile Ile Tyr Leu Lys Ala Leu Ser
        355                 360                 365

Ser Glu Ser Ile Glu Lys Leu Pro Val Phe Asn Lys Ser Ala Phe Lys
    370                 375                 380

His Tyr Gln Met Ser Ser Glu Ala Asp Asp Trp Cys Ile Pro Ser Arg
385                 390                 395                 400

Glu Pro Lys Asn Leu Ala Lys Glu Val Ala Met
                405                 410

<210> SEQ ID NO 23
<211> LENGTH: 324
<212> TYPE: DNA
<213> ORGANISM: human

<400> SEQUENCE: 23
atggcaaatg aagtgcaaga cctgctctcc cctcggaaag ggggacatcc tcctgcagta     60
aaagctggag gaatgagaat ttccaaaaaa caagaaattg gcaccttgga agacatacc    120 aaaaaaacag gattcgagaa acaagtgcc attgcaaatg ttgccaaaat acagacactg    180
gatgccctga tgacgcact ggagaagctc aactataaat ttccagcaac agtgcacatg    240
gcgcatcaaa aacccacacc tgctctggaa aaggttgttc cactgaaaag gatctacatt    300
attcagcagc ctcgaaaatg ttaa                                          324

<210> SEQ ID NO 24
<211> LENGTH: 107
<212> TYPE: PRT
<213> ORGANISM: human

<400> SEQUENCE: 24

Met Ala Asn Glu Val Gln Asp Leu Leu Ser Pro Arg Lys Gly His
1               5                   10                  15

Pro Pro Ala Val Lys Ala Gly Gly Met Arg Ile Ser Lys Lys Gln Glu
                20                  25                  30

Ile Gly Thr Leu Glu Arg His Thr Lys Lys Thr Gly Phe Glu Lys Thr
            35                  40                  45

Ser Ala Ile Ala Asn Val Ala Lys Ile Gln Thr Leu Asp Ala Leu Asn
        50                  55                  60

Asp Ala Leu Glu Lys Leu Asn Tyr Lys Phe Pro Ala Thr Val His Met
65                  70                  75                  80

Ala His Gln Lys Pro Thr Pro Ala Leu Glu Lys Val Val Pro Leu Lys
                85                  90                  95

Arg Ile Tyr Ile Ile Gln Gln Pro Arg Lys Cys
                100                 105

<210> SEQ ID NO 25
<211> LENGTH: 921
<212> TYPE: DNA
```

<213> ORGANISM: human

<400> SEQUENCE: 25

```
atgcccacct gcaccaagtg gtctcgggtg gatagccatg ggaactggac aggaatctgg    60
gtgtgcctgg gcatggcgcg gtgggggaa gaggagagt cagaaagaat gcctgacctg    120
tggacacgga catggctgga gaccttcaca ccaaccctga gggaggacag acagaaaggg    180
ggtgtggtcg gggggcggag gaagagcgag acagagaaag cgcttcggcg gctgcagctc    240
ggcggcggc cgcggggac aaagggcggg cggatcggcg gggaggggc ggggcgcggc    300
caggccaagc ccgggggctc cgcatgctgc agctgccccc gggcgccccc gccgccgccc    360
tcgccgcgga gccgcgcgga gcggagccgg cgagctaacc cgagccagcc ggcgggcgtc    420
ccggaggcgg tggcgcaggg aggggcccga cgctcgcacg tggccccggc ggccgccatg    480
gcggacagcg gcaccgcggg gggcgcggcg ttggcggccc cggcccccgg gccgggcagt    540
ggcggcccag gaccacgcgt ctactttcag agccccccg gggccgcagg agagggcccg    600
ggcggggcgg acgatgaggg cccagtgagg cgccaaggga aggtcaccgt caagtatgac    660
cgcaaggagc tacggaagcg cctcaaccta gaggagtgga tcctggagca gctcacgcgc    720
ctctacgact gccaggaaga ggagatccca gaactggaga ttgacgtgga tgagctcctg    780
gacatggaga gtgacgatgc ccgggctgcc agggtcaagg agctgctggt tgactgttac    840
aaacccacag aggccttcat ttctggcctg ctggacaaga tccggggcat gcagaagctg    900
agcacacccc agaagaagtg a                                              921
```

<210> SEQ ID NO 26
<211> LENGTH: 306
<212> TYPE: PRT
<213> ORGANISM: human

<400> SEQUENCE: 26

```
Met Pro Thr Cys Thr Lys Trp Ser Arg Val Asp Ser His Gly Asn Trp
  1               5                  10                  15
Thr Gly Ile Trp Val Cys Leu Gly Met Ala Arg Trp Gly Glu Glu Gly
             20                  25                  30
Glu Ser Glu Arg Met Pro Asp Leu Trp Thr Arg Thr Trp Leu Glu Thr
         35                  40                  45
Phe Thr Pro Thr Leu Arg Glu Asp Arg Gln Lys Gly Gly Val Val Gly
     50                  55                  60
Gly Arg Arg Lys Ser Glu Thr Glu Lys Ala Leu Arg Arg Leu Gln Leu
 65                  70                  75                  80
Gly Arg Arg Pro Arg Gly Thr Lys Gly Gly Arg Ile Gly Gly Glu Gly
                 85                  90                  95
Ala Gly Arg Gly Gln Ala Lys Pro Gly Gly Ser Ala Cys Cys Ser Cys
            100                 105                 110
Pro Arg Ala Pro Pro Pro Pro Ser Pro Arg Ser Ala Glu Arg
            115                 120                 125
Ser Arg Arg Ala Asn Pro Ser Gln Pro Ala Gly Val Pro Glu Ala Val
        130                 135                 140
Ala Gln Gly Gly Ala Arg Arg Ser His Val Ala Pro Ala Ala Met
145                 150                 155                 160
Ala Asp Ser Gly Thr Ala Gly Gly Ala Ala Leu Ala Ala Pro Ala Pro
                165                 170                 175
Gly Pro Gly Ser Gly Gly Pro Gly Pro Arg Val Tyr Phe Gln Ser Pro
            180                 185                 190
```

```
Pro Gly Ala Ala Gly Glu Gly Pro Gly Gly Ala Asp Asp Glu Gly Pro
        195                 200                 205
Val Arg Arg Gln Gly Lys Val Thr Val Lys Tyr Asp Arg Lys Glu Leu
210                 215                 220
Arg Lys Arg Leu Asn Leu Glu Glu Trp Ile Leu Glu Gln Leu Thr Arg
225                 230                 235                 240
Leu Tyr Asp Cys Gln Glu Glu Ile Pro Glu Leu Glu Ile Asp Val
                245                 250                 255
Asp Glu Leu Leu Asp Met Glu Ser Asp Asp Ala Arg Ala Ala Arg Val
                260                 265                 270
Lys Glu Leu Leu Val Asp Cys Tyr Lys Pro Thr Glu Ala Phe Ile Ser
                275                 280                 285
Gly Leu Leu Asp Lys Ile Arg Gly Met Gln Lys Leu Ser Thr Pro Gln
        290                 295                 300
Lys Lys
305
```

<210> SEQ ID NO 27
<211> LENGTH: 3093
<212> TYPE: DNA
<213> ORGANISM: human

<400> SEQUENCE: 27

| | | |
|---|---|---|
| atgaagattt tccagcgcaa gatgcggtac tggttgcttc cacctttttt ggcaattgtt | 60 |
| tatttctgca ccattgtcca aggtcaagtg gctccaccca caaggttaag atataatgta | 120 |
| atatctcatg acagtataca gatttcatgg aaggctccaa gagggaaatt tggtggttac | 180 |
| aaacttcttg tgactccaac ttcaggtgga aaaactaacc agctgaatct gcagaacact | 240 |
| gcaactaaag caattattca aggccttatg ccagaccaga attacacagt tcaaattatt | 300 |
| gcatacaata agataaaga aagcaagcca gctcaaggcc aattcagaat taagagttta | 360 |
| gaaaaagaa aggatccaaa gcccagagtc aaagttgtgg acagaggaaa tgggagtaga | 420 |
| ccatcttcac cagaagaagt gaaatttgtc tgtcaaactc cagcaattgc tgacattgta | 480 |
| atcctggtcg atggttcatg gagtattgga agattcaact tcagactggt tcggcatttc | 540 |
| ttggaaaacc tggttacagc attcgatgtg ggctcagaga agacacgaat tggtcttgca | 600 |
| cagtatagtg gtgaccccag aatagaatgg cacttgaatg catttagcac aaaagatgaa | 660 |
| gtgattgaag ctgtccgaaa cctcccatat aaaggaggaa atacactaac aggtcttgct | 720 |
| ttgaactaca ttttgaaaa tagcttcaaa ccagaagcag atcaaggac tggagtatcc | 780 |
| aaaattggca ttttaatcac agatggaaaa tcccaagatg acattattcc accatctaga | 840 |
| aatcttcgtg agtctggtgt agaactgttt gccataggg tgaaaaacgc ggatgtgaat | 900 |
| gagctgcagg agatcgcctc tgaaccagac agcactcatg tgtacaatgt tgccgaattc | 960 |
| gatctgatgc acagttgt ggagagtctg accaggactc tctgctctag agtggaagaa | 1020 |
| caggacagag aaattaaagc ctcagcccat gccatcactg gccgcctac ggagttgatt | 1080 |
| acttctgaag tcactgccag aagctttatg gttaactgga ctcatgcccc aggaaatgtg | 1140 |
| gaaaatataca gagttgtgta ttatcctacc aggggtggaa aaccagacga ggtggtggta | 1200 |
| gatggaactg tatcttccac agtgttgaaa aacttgatgt ctttaactga atatcagata | 1260 |
| gcagtctttg caatctatgc ccacactgct agtgaaggcc tacggggaac tgaaactaca | 1320 |
| cttgctttac cgatggcttc tgaccttcta ctgtacgacg tgactgagaa cagcatgcga | 1380 |
| gtcaaatggg atgcagtgcc tgggggcctca ggttacctga tcctttatgc tcctctaaca | 1440 |

-continued

```
gagggcctgg ctggggatga aaaagagatg aaaattggag agacccacac agatattgaa    1500
ttgagtgggt tgttgcccaa tacagaatac acagtcacag tttatgccat gtttggagaa    1560
gaggccagtg atcctgttac gggacaagaa acaacattgg ctttaagtcc accaagaaac    1620
ctgagaatct ccaatgttgg ctctaacagt gctcgattaa cctgggaccc aacttcaaga    1680
cagatcaatg gttatcgaat tgtatataac aatgcagatg ggactgaaat caatgaggtt    1740
gaagtcgatc ctattactac cttccctctg aagggcttga cacctctcac agagtatact    1800
attgctattt tctccatcta tgatgaagga cagtcagagc ctctgactgg agttttttacc    1860 accgaggaag ttccagccca gcaatactta gaaattgatg aggtgacgac agacagtttt    1920
agggtgacct ggcatcccct ctcagctgat gaagggctac acaaattgat gtggattcca    1980
gtctatgggg ggaagactga ggaggttgtc ctgaaagaag agcaggactc acatgttatt    2040
gaaggcctgg agcccggtac ggagtatgaa gtttcactat tggccgtact tgatgatgga    2100
agcgagagtg aggtggtgac tgctgtcggg accacacttg acagtttttg gacagaacca    2160
gctacaacca tagtgcctac cacatctgtg acttcagttt tccagacggg aatcagaaac    2220
ctagttgtag gtgatgaaac tacttctagc ctgcgggtaa aatgggacat ttctgacagc    2280
gatgtgcagc agtttagggt gacctacatg acagctcaag ggaccctga ggaagaagtc    2340 ataggaacgt ttatggtgcc tggaagccag aacaacctcc ttctgaagcc tctgcttcct    2400
gatactgaat acaaagtcac agtgactccc atctacacgg atggcgaagg cgtcagcgtc    2460
tccgctcctg gaaaaacctt accatcctcg ggccccagga acttgcgggt gtccgaggaa    2520
tggtataacc ggttgcgcat tacgtgggac cccccatctt ccccggtgaa aggctataga    2580
attgtctaca aacctgtcag tgttcctggt ccaacactgg aaacgtttgt gggagctgac    2640
attaacacca tccttatcac aaacctcctc agcggaatgg actacaatgt gaagatattt    2700
gcctcccagg cctcaggctt cagcgacgcc ctgacaggca tggtgaaaac attgttcttg    2760
ggtgttacca atctccaagc caaacatgtt gaaatgacca gcttgtgtgc ccactggcag    2820
gtacatcgcc atgccacagc ctataggggtt gttatagaat ccctccagga taggcaaaag    2880
caagaatcca ctgtgggtgg agggacaacc aggcattgct tctatggact tcagcctgat    2940
tctgaatata aaatcagtgt ttatacaaag ctccaggaga ttgaaggacc tagtgtgagc    3000
ataatggaaa aaacacaatc acttcctaca cgaccaccaa cttttcctcc aaccattcca    3060
ccagcaaaag aaggtaaaag aataatagaa taa                                  3093
```

```
<210> SEQ ID NO 28
<211> LENGTH: 1030
<212> TYPE: PRT
<213> ORGANISM: human

<400> SEQUENCE: 28
```

| Met | Lys | Ile | Phe | Gln | Arg | Lys | Met | Arg | Tyr | Trp | Leu | Leu | Pro | Pro | Phe |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |

| Leu | Ala | Ile | Val | Tyr | Phe | Cys | Thr | Ile | Val | Gln | Gly | Gln | Val | Ala | Pro |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Pro | Thr | Arg | Leu | Arg | Tyr | Asn | Val | Ile | Ser | His | Asp | Ser | Ile | Gln | Ile |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ser | Trp | Lys | Ala | Pro | Arg | Gly | Lys | Phe | Gly | Gly | Tyr | Lys | Leu | Leu | Val |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Thr | Pro | Thr | Ser | Gly | Gly | Lys | Thr | Asn | Gln | Leu | Asn | Leu | Gln | Asn | Thr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ala | Thr | Lys | Ala | Ile | Ile | Gln | Gly | Leu | Met | Pro | Asp | Gln | Asn | Tyr | Thr |
|-----|-----|-----|-----|-----|-----|-----|-----|-----|-----|-----|-----|-----|-----|-----|-----|

```
                    85                  90                  95
Val Gln Ile Ile Ala Tyr Asn Lys Asp Lys Glu Ser Lys Pro Ala Gln
                100                 105                 110

Gly Gln Phe Arg Ile Lys Asp Leu Glu Lys Arg Lys Asp Pro Lys Pro
            115                 120                 125

Arg Val Lys Val Val Asp Arg Gly Asn Gly Ser Arg Pro Ser Ser Pro
        130                 135                 140

Glu Glu Val Lys Phe Val Cys Gln Thr Pro Ala Ile Ala Asp Ile Val
145                 150                 155                 160

Ile Leu Val Asp Gly Ser Trp Ser Ile Gly Arg Phe Asn Phe Arg Leu
                165                 170                 175

Val Arg His Phe Leu Glu Asn Leu Val Thr Ala Phe Asp Val Gly Ser
            180                 185                 190

Glu Lys Thr Arg Ile Gly Leu Ala Gln Tyr Ser Gly Asp Pro Arg Ile
        195                 200                 205

Glu Trp His Leu Asn Ala Phe Ser Thr Lys Asp Glu Val Ile Glu Ala
    210                 215                 220

Val Arg Asn Leu Pro Tyr Lys Gly Gly Asn Thr Leu Thr Gly Leu Ala
225                 230                 235                 240

Leu Asn Tyr Ile Phe Glu Asn Ser Phe Lys Pro Glu Ala Gly Ser Arg
                245                 250                 255

Thr Gly Val Ser Lys Ile Gly Ile Leu Ile Thr Asp Gly Lys Ser Gln
            260                 265                 270

Asp Asp Ile Ile Pro Pro Ser Arg Asn Leu Arg Glu Ser Gly Val Glu
        275                 280                 285

Leu Phe Ala Ile Gly Val Lys Asn Ala Asp Val Asn Glu Leu Gln Glu
    290                 295                 300

Ile Ala Ser Glu Pro Asp Ser Thr His Val Tyr Asn Val Ala Glu Phe
305                 310                 315                 320

Asp Leu Met His Thr Val Val Glu Ser Leu Thr Arg Thr Leu Cys Ser
                325                 330                 335

Arg Val Glu Glu Gln Asp Arg Glu Ile Lys Ala Ser Ala His Ala Ile
            340                 345                 350

Thr Gly Pro Pro Thr Glu Leu Ile Thr Ser Glu Val Thr Ala Arg Ser
        355                 360                 365

Phe Met Val Asn Trp Thr His Ala Pro Gly Asn Val Glu Lys Tyr Arg
    370                 375                 380

Val Val Tyr Tyr Pro Thr Arg Gly Gly Lys Pro Asp Glu Val Val Val
385                 390                 395                 400

Asp Gly Thr Val Ser Ser Thr Val Leu Lys Asn Leu Met Ser Leu Thr
                405                 410                 415

Glu Tyr Gln Ile Ala Val Phe Ala Ile Tyr Ala His Thr Ala Ser Glu
            420                 425                 430

Gly Leu Arg Gly Thr Glu Thr Thr Leu Ala Leu Pro Met Ala Ser Asp
        435                 440                 445

Leu Leu Leu Tyr Asp Val Thr Glu Asn Ser Met Arg Val Lys Trp Asp
    450                 455                 460

Ala Val Pro Gly Ala Ser Gly Tyr Leu Ile Leu Tyr Ala Pro Leu Thr
465                 470                 475                 480

Glu Gly Leu Ala Gly Asp Glu Lys Glu Met Lys Ile Gly Glu Thr His
                485                 490                 495

Thr Asp Ile Glu Leu Ser Gly Leu Leu Pro Asn Thr Glu Tyr Thr Val
            500                 505                 510
```

-continued

Thr Val Tyr Ala Met Phe Gly Glu Glu Ala Ser Asp Pro Val Thr Gly
        515                 520                 525

Gln Glu Thr Thr Leu Ala Leu Ser Pro Pro Arg Asn Leu Arg Ile Ser
        530                 535                 540

Asn Val Gly Ser Asn Ser Ala Arg Leu Thr Trp Asp Pro Thr Ser Arg
545                 550                 555                 560

Gln Ile Asn Gly Tyr Arg Ile Val Tyr Asn Asn Ala Asp Gly Thr Glu
                565                 570                 575

Ile Asn Glu Val Glu Val Asp Pro Ile Thr Thr Phe Pro Leu Lys Gly
            580                 585                 590

Leu Thr Pro Leu Thr Glu Tyr Thr Ile Ala Ile Phe Ser Ile Tyr Asp
        595                 600                 605

Glu Gly Gln Ser Glu Pro Leu Thr Gly Val Phe Thr Thr Glu Glu Val
        610                 615                 620

Pro Ala Gln Gln Tyr Leu Glu Ile Asp Glu Val Thr Thr Asp Ser Phe
625                 630                 635                 640

Arg Val Thr Trp His Pro Leu Ser Ala Asp Glu Gly Leu His Lys Leu
                645                 650                 655

Met Trp Ile Pro Val Tyr Gly Gly Lys Thr Glu Glu Val Val Leu Lys
            660                 665                 670

Glu Glu Gln Asp Ser His Val Ile Glu Gly Leu Glu Pro Gly Thr Glu
        675                 680                 685

Tyr Glu Val Ser Leu Leu Ala Val Leu Asp Asp Gly Ser Glu Ser Glu
        690                 695                 700

Val Val Thr Ala Val Gly Thr Thr Leu Asp Ser Phe Trp Thr Glu Pro
705                 710                 715                 720

Ala Thr Thr Ile Val Pro Thr Thr Ser Val Thr Ser Val Phe Gln Thr
                725                 730                 735

Gly Ile Arg Asn Leu Val Val Gly Asp Glu Thr Thr Ser Ser Leu Arg
            740                 745                 750

Val Lys Trp Asp Ile Ser Asp Ser Asp Val Gln Gln Phe Arg Val Thr
        755                 760                 765

Tyr Met Thr Ala Gln Gly Asp Pro Glu Glu Val Ile Gly Thr Val
        770                 775                 780

Met Val Pro Gly Ser Gln Asn Asn Leu Leu Leu Lys Pro Leu Leu Pro
785                 790                 795                 800

Asp Thr Glu Tyr Lys Val Thr Val Thr Pro Ile Tyr Thr Asp Gly Glu
                805                 810                 815

Gly Val Ser Val Ser Ala Pro Gly Lys Thr Leu Pro Ser Ser Gly Pro
            820                 825                 830

Gln Asn Leu Arg Val Ser Glu Glu Trp Tyr Asn Arg Leu Arg Ile Thr
        835                 840                 845

Trp Asp Pro Pro Ser Ser Pro Val Lys Gly Tyr Arg Ile Val Tyr Lys
        850                 855                 860

Pro Val Ser Val Pro Gly Pro Thr Leu Glu Thr Phe Val Gly Ala Asp
865                 870                 875                 880

Ile Asn Thr Ile Leu Ile Thr Asn Leu Leu Ser Gly Met Asp Tyr Asn
                885                 890                 895

Val Lys Ile Phe Ala Ser Gln Ala Ser Gly Phe Ser Asp Ala Leu Thr
            900                 905                 910

Gly Met Val Lys Thr Leu Phe Leu Gly Val Thr Asn Leu Gln Ala Lys
        915                 920                 925

His Val Glu Met Thr Ser Leu Cys Ala His Trp Gln Val His Arg His
        930                 935                 940

Ala Thr Ala Tyr Arg Val Val Ile Glu Ser Leu Gln Asp Arg Gln Lys
945                 950                 955                 960

Gln Glu Ser Thr Val Gly Gly Thr Thr Arg His Cys Phe Tyr Gly
            965                 970                 975

Leu Gln Pro Asp Ser Glu Tyr Lys Ile Ser Val Tyr Thr Lys Leu Gln
            980                 985                 990

Glu Ile Glu Gly Pro Ser Val Ser Ile Met Glu Lys Thr Gln Ser Leu
            995                 1000                1005

Pro Thr Arg Pro Pro Thr Phe Pro Pro Thr Ile Pro Pro Ala Lys
    1010                1015                1020

Glu Gly Lys Arg Ile Ile Glu
    1025                1030

<210> SEQ ID NO 29
<211> LENGTH: 1326
<212> TYPE: DNA
<213> ORGANISM: human

<400> SEQUENCE: 29

| | | | | | |
|---|---|---|---|---|---|
| atgggcggcc | cgcgggcttg | ggcgctgctc | tgcctcgggc | tcctgctccc | gggaggcggc | 60 |
| gctgcgtgga | gcatcggggc | agctccgttc | tccggacgca | ggaactggtg | ctcctatgtg | 120 |
| gtgacccgca | ccatctcatg | ccatgtgcag | aatggcacct | accttcagcg | agtgctgcag | 180 |
| aactgcccct | ggcccatgag | ctgtccgggg | agcagctaca | gaactgtggt | gagacccaca | 240 |
| tacaaggtga | tgtacaagat | agtgaccgcc | cgtgagtgga | ggtgctgccc | tgggcactca | 300 |
| ggagtgagct | gcgaggaagc | ttcctctgcc | tccttggagc | ccatgtggtc | gggcagtacc | 360 |
| atgcggcgga | tggcgcttcg | gcccacagcc | ttctcaggtt | gtctcaactg | cagcaaagtg | 420 |
| tcagagctga | cagagcggct | gaaggtgctg | gaggccaaga | tgaccatgct | gactgtcata | 480 |
| gagcagccag | tacctccaac | accagctacc | cctgaggacc | ctgccccgct | ctggggtccc | 540 |
| cctcctgccc | agggcagccc | cggagatgga | ggcctccagg | accaagtcgg | tgcttggggg | 600 |
| cttcccgggc | ccaccggccc | caagggagat | gccggcagtc | ggggcccaat | ggggatgaga | 660 |
| ggcccaccag | gtccacaggg | cccccagggg | agccctggcc | gggctggagc | tgtgggcacc | 720 |
| cctggagaga | ggggacctcc | tgggccacca | gggcctcctg | gcccccctgg | gcccccagcc | 780 |
| cctgttgggc | caccccatgc | ccggatctcc | cagcatggag | accattgct | gtccaacacc | 840 |
| ttcactgaga | ccaacaacca | ctggcccag | ggaccactg | ggcctccagg | ccctccaggg | 900 |
| cccatgggtc | cccctgggcc | tcctggcccc | acaggtgtcc | ctgggagtcc | tggtcacata | 960 |
| ggacccccag | gccccactgg | acccaaagga | atctctggcc | acccaggaga | gaagggcgag | 1020 |
| agaggactgc | gtggggagcc | tggccccaa | ggctctgctg | ggcagcgggg | ggaacctggc | 1080 |
| cctaagggag | accctggtga | aagagccac | tgggggagg | ggttgcacca | gctacgcgag | 1140 |
| gctttgaaga | ttttagctga | gagggttta | atcttggaaa | caatgattgg | gctctatgaa | 1200 |
| ccagagctgg | ggtctgggc | gggccctgcc | ggcacaggca | ccccagcct | ccttcggggc | 1260 |
| aagaggggcg | acatgcaac | caactaccgg | atcgtggccc | ccaggagccg | ggacgagaga | 1320 |
| ggctga | | | | | | 1326 |

<210> SEQ ID NO 30
<211> LENGTH: 441
<212> TYPE: PRT
<213> ORGANISM: human

<400> SEQUENCE: 30

```
Met Gly Gly Pro Arg Ala Trp Ala Leu Leu Cys Leu Gly Leu Leu
1               5                   10                  15

Pro Gly Gly Gly Ala Ala Trp Ser Ile Gly Ala Ala Pro Phe Ser Gly
            20                  25                  30

Arg Arg Asn Trp Cys Ser Tyr Val Val Thr Arg Thr Ile Ser Cys His
        35                  40                  45

Val Gln Asn Gly Thr Tyr Leu Gln Arg Val Leu Gln Asn Cys Pro Trp
50                  55                  60

Pro Met Ser Cys Pro Gly Ser Ser Tyr Arg Thr Val Val Arg Pro Thr
65              70                  75                  80

Tyr Lys Val Met Tyr Lys Ile Val Thr Ala Arg Glu Trp Arg Cys Cys
                85                  90                  95

Pro Gly His Ser Gly Val Ser Cys Glu Glu Ala Ser Ser Ala Ser Leu
            100                 105                 110

Glu Pro Met Trp Ser Gly Ser Thr Met Arg Arg Met Ala Leu Arg Pro
        115                 120                 125

Thr Ala Phe Ser Gly Cys Leu Asn Cys Ser Lys Val Ser Glu Leu Thr
    130                 135                 140

Glu Arg Leu Lys Val Leu Glu Ala Lys Met Thr Met Leu Thr Val Ile
145                 150                 155                 160

Glu Gln Pro Val Pro Thr Pro Ala Thr Pro Glu Asp Pro Ala Pro
                165                 170                 175

Leu Trp Gly Pro Pro Ala Gln Gly Ser Pro Gly Asp Gly Leu
            180                 185                 190

Gln Asp Gln Val Gly Ala Trp Gly Leu Pro Gly Pro Thr Gly Pro Lys
        195                 200                 205

Gly Asp Ala Gly Ser Arg Gly Pro Met Gly Met Arg Gly Pro Pro Gly
    210                 215                 220

Pro Gln Gly Pro Pro Gly Ser Pro Gly Arg Ala Gly Ala Val Gly Thr
225                 230                 235                 240

Pro Gly Glu Arg Gly Pro Pro Gly Pro Pro Gly Pro Pro Gly Pro Pro
            245                 250                 255

Gly Pro Pro Ala Pro Val Gly Pro Pro His Ala Arg Ile Ser Gln His
        260                 265                 270

Gly Asp Pro Leu Leu Ser Asn Thr Phe Thr Glu Thr Asn His Trp
    275                 280                 285

Pro Gln Gly Pro Thr Gly Pro Pro Gly Pro Pro Gly Pro Met Gly Pro
    290                 295                 300

Pro Gly Pro Pro Gly Pro Thr Gly Val Pro Gly Ser Pro Gly His Ile
305                 310                 315                 320

Gly Pro Pro Gly Pro Thr Gly Pro Lys Gly Ile Ser Gly His Pro Gly
            325                 330                 335

Glu Lys Gly Glu Arg Gly Leu Arg Gly Glu Pro Gly Pro Gln Gly Ser
        340                 345                 350

Ala Gly Gln Arg Gly Glu Pro Gly Pro Lys Gly Asp Pro Gly Glu Lys
    355                 360                 365

Ser His Trp Gly Glu Gly Leu His Gln Leu Arg Glu Ala Leu Lys Ile
    370                 375                 380

Leu Ala Glu Arg Val Leu Ile Leu Glu Thr Met Ile Gly Leu Tyr Glu
385                 390                 395                 400

Pro Glu Leu Gly Ser Gly Ala Gly Pro Ala Gly Thr Gly Thr Pro Ser
            405                 410                 415

Leu Leu Arg Gly Lys Arg Gly Gly His Ala Thr Asn Tyr Arg Ile Val
```

```
                420           425           430
Ala Pro Arg Ser Arg Asp Glu Arg Gly
        435             440

<210> SEQ ID NO 31
<211> LENGTH: 4131
<212> TYPE: DNA
<213> ORGANISM: human

<400> SEQUENCE: 31 atggagggggg accgggtggc cgggcggccg gtgctgtcgt cgttaccagt gctactgctg     60
ctgcagttgc taatgttgcg ggccgcgcg ctgcacccag acgagctctt cccacacggg    120
gagtcgtggt gggaccagct cctgcaggaa ggcgacgacg taaagctcag ccgtggtgaa    180
gctggcgaat cccctgcact tcttacgaag cccgattcag caacctctac gtgggcacca    240
acggcatcat ctccactcag gacttcccca gggaaacgca gtatgtggac tatgatttcc    300
ccaccgactt cccggccatc gccccttttc tggcggacat cgacgagc cacggcagag    360
gccgagtcct gtaccgagag gacacctccc ccgcagtgct gggcctggcc gccgctatg    420
tgcgcgctgg cttcccgcgc tctgcgcgct ttttacccc acccacgcct tcctggccac    480
ctgggagcag gtaggcgctt acgaggaggt caaacgcggg cgctgccctc gggagagctg    540
aacactttcc aggcagttt ggcatctgat gggtctgata gctacgccct ctttctttat    600
cctgccaacg gcctgcagtt ccttggaacc cgccccaaag agtcttacaa tgtccagctt    660
cagcttccag ctcgggtggg cttctgccga ggggaggctg atgatctgaa gtcagaagga    720
ccatatttca gcttgactag cactgaacag tctgtgaaaa atctctatca actaagcaac    780
ctgggggtcc ctggagtgtg ggcttttcat atcggcagca cttccccgtt ggacaatgtc    840
aggccagctg cagttggaga ccttttccgct gcccactctt ctgttcccct gggacgttcc    900
ttcagccatg ctacagccct ggaaagtgac tataatgagg acaatttgga ttactacgat    960
gtgaatgagg aggaagctga ataccttccg ggtgaaccag aggaggcatt gaatggccac   1020
agcagcattg atgtttcctt ccaatccaaa gtggatacaa agcctttaga ggaatcttcc   1080
accttggatc ctcacaccaa agaaggaaca tctctgggag aggtaggggg cccagattta   1140
aaaggccaag ttgagccctg ggatgagaga gagaccagaa gcccagctcc accagaggta   1200
gacagagatt cactggctcc ttcctgggaa accccaccac cgtaccccga aaacggaagc   1260
atccagccct acccagatgg agggccagtg ccttcggaaa tggatgttcc cccagctcat   1320
cctgaagaag aaattgttct tcgaagttac cctgcttcag gtcacactac acccttaagt   1380
cgagggacgt atgaggtggg actgaagac aacataggtt ccaacaccga ggtcttcacg   1440
tataatgctg ccaacaagga aacctgtgaa cacaaccaca gacaatgctc ccggcatgcc   1500
ttctgcacgg actatgccac tggcttctgc tgccactgcc aatccaagtt ttatggaaat   1560
gggaagcact gtctgcctga gggggcacct caccgagtga tgggaaagt gagtggccac   1620
ctccacgtgg gccatacacc cgtgcacttc actgatgtgg acctgcatgc gtatatcgtg   1680
ggcaatgatg gcagagccta cacggccatc agccacatcc acagccagc agcccaggcc   1740
ctcctccccc tcacaccaat ggaggcctg tttggctggc tctttgcttt agaaaaaacct   1800
ggctctgaga acggcttcag cctcgcaggt gctgcctta cccatgacat ggaagttaca   1860
ttctacccgg gagaggagac ggttcgtatc actcaaactg ctgagggact tgacccagag   1920
aactacctga gcattaagac caacattcaa ggccaggtgc cttacgtccc agcaaatttc   1980
acagcccaca tctctcccta caaggagctg taccactact ccgactccac tgtgacctct   2040
```

| | | |
|---|---|---|
| acaagttcca gagactactc tctgactttt ggtgcaatca accaaacatg gtcctaccgc | 2100 | |
| atccaccaga acatcactta ccaggtgtgc aggcacgccc ccagacaccc gtccttcccc | 2160 | |
| accacccagc agctgaacgt ggaccgggtc tttgccttgt ataatgatga agaaagagtg | 2220 | |
| cttagatttg ctgtgaccaa tcaaattggc ccggtcaaag aagattcaga ccccactccg | 2280 | |
| gtgaatcctt gctatgatgg gagccacatg tgtgacacaa cagcacggtg ccatccaggg | 2340 | |
| acaggtgtag attacacctg tgagtgcgca tctgggtacc agggagatgg acggaactgt | 2400 | |
| gtggatgaaa atgaatgtgc aactggcttt catcgctgtg cccccaactc tgtatgtatc | 2460 | |
| aacttgcctg gaagctacag gtgtgagtgc cggagtggtt atgagtttgc agatgaccgg | 2520 | |
| catacttgca tcttgatcac cccacctgcc aaccctgtg aggatggcag tcatacctgt | 2580 | |
| gctcctgctg ggcaggcccg gtgtgttcac catggaggca gcacgttcag ctgtgcctgc | 2640 | |
| ctgcctggtt atgccggcga tgggcaccag tgcactgatg tagatgaatg ctcagaaaac | 2700 | |
| agatgtcacc ctgcagctac ctgctacaat actcctggtt ccttctcctg ccgttgtcaa | 2760 | |
| cccggatatt atggggatgg atttcagtgc ataccgtgact ccacctcaag cctgacaccc | 2820 | |
| tgtgaacaac agcagcgcca tgcccaggcc cagtatgcct accctggggc ccggttccac | 2880 | |
| atcccccaat gcgacgagca gggcaacttc ctgcccctac agtgtcatgg cagcactggt | 2940 | |
| ttctgctggt gcgtggaccc tgatggtcat gaagttcctg gtacccagac tccacctggc | 3000 | |
| tccacccgc ctcactgtgg accatcacca gagcccaccc agaggccccc gaccatctgt | 3060 | |
| gagcgctgga gggaaaacct gctggagcac tacggtggca cccccgaga tgaccagtac | 3120 | |
| gtgcccagt gcgatgacct gggccacttc atcccctgc agtgccacgg aaagagcgac | 3180 | |
| ttctgctggt gtgtggacaa agatggcaga gaggtgcagg gcacccgctc ccagccaggc | 3240 | |
| accacccctg cgtgtatacc caccgtcgct ccacccatgg tccggcccac gccccggcca | 3300 | |
| gatgtgaccc ctccatctgt gggccacttc ctgctctata tcagggcca gcagattggc | 3360 | |
| tacttacccc tcaatggcac caggcttcag aaggatgcag ctaagaccct gctgtctctg | 3420 | |
| catggctcca taatcgtggg aattgattac gactgccggg agaggatggt gtactggaca | 3480 | |
| gatgttgctg gacggacaat cagccgtgcc ggtctggaac tgggagcaga gcctgagacg | 3540 | |
| atcgtgaatt caggtctgat aagccctgaa ggacttgcca tagaccacat ccgcagaaca | 3600 | |
| atgtactgga cggacagtgt cctggataag atagagagcg ccctgctgga tggctctgag | 3660 | |
| cgcaaggtcc tcttctacac agatctggtg aatccccgtg ccatcgctgt ggatccaatc | 3720 | |
| cgaggcaact tgtactggac agactggaat agagaagctc taaaattga aacgtcatct | 3780 | |
| ttagatggag aaaacagaag aattctgatc aatacagaca ttggattgcc caatggctta | 3840 | |
| acctttgacc ctttctctaa actgctctgc tgggcagatg caggaaccaa aaaactggag | 3900 | |
| tgtacactac ctgatggaac tggacggcgt gtcattcaaa acaacctcaa gtacccttc | 3960 | |
| agcatcgtaa gctatgcaga tcacttctac cacacagact ggaggaggga tggtgttgta | 4020 | |
| tcagtaaata acatagtggg ccagtttact gatgagtatc tcccagaaca acgatctcac | 4080 | |
| ctctacggga taactgcagt ctaccctac tgcccaacag gaagaaagta a | 4131 | |

<210> SEQ ID NO 32
<211> LENGTH: 1376
<212> TYPE: PRT
<213> ORGANISM: human

<400> SEQUENCE: 32

Met Glu Gly Asp Arg Val Ala Gly Arg Pro Val Leu Ser Ser Leu Pro

-continued

```
1               5                   10                  15
Val Leu Leu Leu Leu Gln Leu Leu Met Leu Arg Ala Ala Ala Leu His
                20                  25                  30

Pro Asp Glu Leu Phe Pro His Gly Glu Ser Trp Trp Asp Gln Leu Leu
                35                  40                  45

Gln Glu Gly Asp Asp Val Lys Leu Ser Arg Gly Ala Gly Glu Ser
    50                  55                  60

Pro Ala Leu Leu Thr Lys Pro Asp Ser Ala Thr Ser Thr Trp Ala Pro
65                  70                  75                  80

Thr Ala Ser Ser Pro Leu Arg Thr Ser Pro Gly Lys Arg Ser Met Trp
                85                  90                  95

Thr Met Ile Ser Pro Pro Thr Ser Arg Pro Ser Pro Leu Phe Trp Arg
                100                 105                 110

Thr Ser Thr Arg Ala Thr Ala Glu Ala Glu Ser Cys Thr Glu Arg Thr
                115                 120                 125

Pro Pro Pro Gln Cys Trp Ala Trp Pro Pro Ala Met Cys Ala Leu Ala
    130                 135                 140

Ser Arg Ala Leu Arg Ala Phe Tyr Pro His Pro Arg Leu Pro Gly His
145                 150                 155                 160

Leu Gly Ala Gly Arg Arg Leu Arg Gly Gly Gln Thr Arg Ala Leu Pro
                165                 170                 175

Ser Gly Glu Leu Asn Thr Phe Gln Ala Val Leu Ala Ser Asp Gly Ser
                180                 185                 190

Asp Ser Tyr Ala Leu Phe Leu Tyr Pro Ala Asn Gly Leu Gln Phe Leu
                195                 200                 205

Gly Thr Arg Pro Lys Glu Ser Tyr Asn Val Gln Leu Gln Leu Pro Ala
                210                 215                 220

Arg Val Gly Phe Cys Arg Gly Glu Ala Asp Asp Leu Lys Ser Glu Gly
225                 230                 235                 240

Pro Tyr Phe Ser Leu Thr Ser Thr Glu Gln Ser Val Lys Asn Leu Tyr
                245                 250                 255

Gln Leu Ser Asn Leu Gly Ile Pro Gly Val Trp Ala Phe His Ile Gly
                260                 265                 270

Ser Thr Ser Pro Leu Asp Asn Val Arg Pro Ala Ala Val Gly Asp Leu
                275                 280                 285

Ser Ala Ala His Ser Ser Val Pro Leu Gly Arg Ser Phe Ser His Ala
                290                 295                 300

Thr Ala Leu Glu Ser Asp Tyr Asn Glu Asp Asn Leu Asp Tyr Tyr Asp
305                 310                 315                 320

Val Asn Glu Glu Glu Ala Glu Tyr Leu Pro Gly Glu Pro Glu Glu Ala
                325                 330                 335

Leu Asn Gly His Ser Ser Ile Asp Val Ser Phe Gln Ser Lys Val Asp
                340                 345                 350

Thr Lys Pro Leu Glu Glu Ser Ser Thr Leu Asp Pro His Thr Lys Glu
                355                 360                 365

Gly Thr Ser Leu Gly Glu Val Gly Pro Asp Leu Lys Gly Gln Val
                370                 375                 380

Glu Pro Trp Asp Glu Arg Glu Thr Arg Ser Pro Ala Pro Pro Glu Val
385                 390                 395                 400

Asp Arg Asp Ser Leu Ala Pro Ser Trp Glu Thr Pro Pro Pro Tyr Pro
                405                 410                 415

Glu Asn Gly Ser Ile Gln Pro Tyr Pro Asp Gly Pro Val Pro Ser
                420                 425                 430
```

-continued

```
Glu Met Asp Val Pro Pro Ala His Pro Glu Glu Ile Val Leu Arg
    435                 440                 445

Ser Tyr Pro Ala Ser Gly His Thr Thr Pro Leu Ser Arg Gly Thr Tyr
450                 455                 460

Glu Val Gly Leu Glu Asp Asn Ile Gly Ser Asn Thr Glu Val Phe Thr
465                 470                 475                 480

Tyr Asn Ala Ala Asn Lys Glu Thr Cys Glu His Asn His Arg Gln Cys
                485                 490                 495

Ser Arg His Ala Phe Cys Thr Asp Tyr Ala Thr Gly Phe Cys Cys His
            500                 505                 510

Cys Gln Ser Lys Phe Tyr Gly Asn Gly Lys His Cys Leu Pro Glu Gly
        515                 520                 525

Ala Pro His Arg Val Asn Gly Lys Val Ser Gly His Leu His Val Gly
    530                 535                 540

His Thr Pro Val His Phe Thr Asp Val Asp Leu His Ala Tyr Ile Val
545                 550                 555                 560

Gly Asn Asp Gly Arg Ala Tyr Thr Ala Ile Ser His Ile Pro Gln Pro
                565                 570                 575

Ala Ala Gln Ala Leu Leu Pro Leu Thr Pro Ile Gly Gly Leu Phe Gly
            580                 585                 590

Trp Leu Phe Ala Leu Glu Lys Pro Gly Ser Glu Asn Gly Phe Ser Leu
        595                 600                 605

Ala Gly Ala Ala Phe Thr His Asp Met Glu Val Thr Phe Tyr Pro Gly
    610                 615                 620

Glu Glu Thr Val Arg Ile Thr Gln Thr Ala Gly Leu Asp Pro Glu
625                 630                 635                 640

Asn Tyr Leu Ser Ile Lys Thr Asn Ile Gln Gly Gln Val Pro Tyr Val
                645                 650                 655

Pro Ala Asn Phe Thr Ala His Ile Ser Pro Tyr Lys Glu Leu Tyr His
            660                 665                 670

Tyr Ser Asp Ser Thr Val Thr Ser Thr Ser Arg Asp Tyr Ser Leu
        675                 680                 685

Thr Phe Gly Ala Ile Asn Gln Thr Trp Ser Tyr Arg Ile His Gln Asn
    690                 695                 700

Ile Thr Tyr Gln Val Cys Arg His Ala Pro Arg His Pro Ser Phe Pro
705                 710                 715                 720

Thr Thr Gln Gln Leu Asn Val Asp Arg Val Phe Ala Leu Tyr Asn Asp
                725                 730                 735

Glu Glu Arg Val Leu Arg Phe Ala Val Thr Asn Gln Ile Gly Pro Val
            740                 745                 750

Lys Glu Asp Ser Asp Pro Thr Pro Val Asn Pro Cys Tyr Asp Gly Ser
        755                 760                 765

His Met Cys Asp Thr Thr Ala Arg Cys His Pro Gly Thr Gly Val Asp
    770                 775                 780

Tyr Thr Cys Glu Cys Ala Ser Gly Tyr Gln Gly Asp Gly Arg Asn Cys
785                 790                 795                 800

Val Asp Glu Asn Glu Cys Ala Thr Gly Phe His Arg Cys Gly Pro Asn
                805                 810                 815

Ser Val Cys Ile Asn Leu Pro Gly Ser Tyr Arg Cys Glu Cys Arg Ser
            820                 825                 830

Gly Tyr Glu Phe Ala Asp Asp Arg His Thr Cys Ile Leu Ile Thr Pro
        835                 840                 845

Pro Ala Asn Pro Cys Glu Asp Gly Ser His Thr Cys Ala Pro Ala Gly
    850                 855                 860
```

```
Gln Ala Arg Cys Val His His Gly Gly Ser Thr Phe Ser Cys Ala Cys
865                 870                 875                 880

Leu Pro Gly Tyr Ala Gly Asp Gly His Gln Cys Thr Asp Val Asp Glu
        885                 890                 895

Cys Ser Glu Asn Arg Cys His Pro Ala Ala Thr Cys Tyr Asn Thr Pro
            900                 905                 910

Gly Ser Phe Ser Cys Arg Cys Gln Pro Gly Tyr Tyr Gly Asp Gly Phe
                915                 920                 925

Gln Cys Ile Pro Asp Ser Thr Ser Ser Leu Thr Pro Cys Glu Gln Gln
930                 935                 940

Gln Arg His Ala Gln Ala Gln Tyr Ala Tyr Pro Gly Ala Arg Phe His
945                 950                 955                 960

Ile Pro Gln Cys Asp Glu Gln Gly Asn Phe Leu Pro Leu Gln Cys His
            965                 970                 975

Gly Ser Thr Gly Phe Cys Trp Cys Val Asp Pro Asp Gly His Glu Val
                980                 985                 990

Pro Gly Thr Gln Thr Pro Pro Gly Ser Thr Pro Pro His Cys Gly Pro
            995                 1000                1005

Ser Pro  Glu Pro Thr Gln Arg  Pro Pro Thr Ile Cys  Glu Arg Trp
1010                 1015                 1020

Arg Glu  Asn Leu Leu Glu His  Tyr Gly Gly Thr Pro  Arg Asp Asp
1025                 1030                 1035

Gln Tyr  Val Pro Gln Cys Asp  Asp Leu Gly His Phe  Ile Pro Leu
1040                 1045                 1050

Gln Cys  His Gly Lys Ser Asp  Phe Cys Trp Cys Val  Asp Lys Asp
1055                 1060                 1065

Gly Arg  Glu Val Gln Gly Thr  Arg Ser Gln Pro Gly  Thr Thr Pro
1070                 1075                 1080

Ala Cys  Ile Pro Thr Val Ala  Pro Pro Met Val Arg  Pro Thr Pro
1085                 1090                 1095

Arg Pro  Asp Val Thr Pro Pro  Ser Val Gly Thr Phe  Leu Leu Tyr
1100                 1105                 1110

Thr Gln  Gly Gln Gln Ile Gly  Tyr Leu Pro Leu Asn  Gly Thr Arg
1115                 1120                 1125

Leu Gln  Lys Asp Ala Ala Lys  Thr Leu Leu Ser Leu  His Gly Ser
1130                 1135                 1140

Ile Ile  Val Gly Ile Asp Tyr  Asp Cys Arg Glu Arg  Met Val Tyr
1145                 1150                 1155

Trp Thr  Asp Val Ala Gly Arg  Thr Ile Ser Arg Ala  Gly Leu Glu
1160                 1165                 1170

Leu Gly  Ala Glu Pro Glu Thr  Ile Val Asn Ser Gly  Leu Ile Ser
1175                 1180                 1185

Pro Glu  Gly Leu Ala Ile Asp  His Ile Arg Arg Thr  Met Tyr Trp
1190                 1195                 1200

Thr Asp  Ser Val Leu Asp Lys  Ile Glu Ser Ala Leu  Leu Asp Gly
1205                 1210                 1215

Ser Glu  Arg Lys Val Leu Phe  Tyr Thr Asp Leu Val  Asn Pro Arg
1220                 1225                 1230

Ala Ile  Ala Val Asp Pro Ile  Arg Gly Asn Leu Tyr  Trp Thr Asp
1235                 1240                 1245

Trp Asn  Arg Glu Ala Pro Lys  Ile Glu Thr Ser Ser  Leu Asp Gly
1250                 1255                 1260

Glu Asn  Arg Arg Ile Leu Ile  Asn Thr Asp Ile Gly  Leu Pro Asn
```

```
                1265                1270                1275
Gly Leu Thr Phe Asp Pro Phe Ser Lys Leu Leu Cys Trp Ala Asp
    1280                1285                1290

Ala Gly Thr Lys Lys Leu Glu Cys Thr Leu Pro Asp Gly Thr Gly
    1295                1300                1305

Arg Arg Val Ile Gln Asn Asn Leu Lys Tyr Pro Phe Ser Ile Val
    1310                1315                1320

Ser Tyr Ala Asp His Phe Tyr His Thr Asp Trp Arg Arg Asp Gly
    1325                1330                1335

Val Val Ser Val Asn Lys His Ser Gly Gln Phe Thr Asp Glu Tyr
    1340                1345                1350

Leu Pro Glu Gln Arg Ser His Leu Tyr Gly Ile Thr Ala Val Tyr
    1355                1360                1365

Pro Tyr Cys Pro Thr Gly Arg Lys
    1370                1375

<210> SEQ ID NO 33
<211> LENGTH: 1329
<212> TYPE: DNA
<213> ORGANISM: human

<400> SEQUENCE: 33
atgcagccgc ctccaagtct gtgcggacgc gccctggttg cgctggttct tgcctgcggc      60
ctgtcgcgga tctggggaga ggagagaggc ttcccgcctg acagggccac tccgcttttg     120
caaaccgcag agataatgac gccacccact aagaccttat ggcccaaggg ttccaacgcc     180
agtctggcgc ggtcgttggc acctgcggag gtgcctaaag agacaggac ggcaggatct     240 ccgccacgca ccatctcccc tccccgtgc caaggaccca tcgagatcaa ggagactttc     300
aaatacatca cacggttgt gtcctgcctt gtgttcgtgc tggggatcat cgggaactcc     360
acacttctga gaattatcta caagaacaag tgcatgcgaa acgtcccaa tatcttgatc     420 gccagcttgg ctctgggaga cctgctgcac atcgtcattg acatccctat caatgtctac     480
aagctgctgg cagaggactg gccatttgga gctgagatgt gtaagctggt gcctttcata     540
cagaaagcct ccgtgggaat cactgtgctg agtctatgtg ctctgagtat tgacagatat     600
cgagctgttg cttcttggag tagaattaaa ggaattgggg ttccaaaatg gacagcagta     660
gaaattgttt tgatttgggt ggtctctgtg gttctggctg tccctgaagc cataggtttt     720
gatataatta cgatggacta caaaggaagt tatctgcgaa tctgcttgct tcatcccgtt     780
cagaagacag ctttcatgca gttttacaag acagcaaaag attggtggct gttcagtttc     840 tattttctgct tgccattggc catcactgca ttttttttata cactaatgac ctgtgaaatg     900
ttgagaaaga aaagtggcat gcagattgct ttaaatgatc acctaaagca gagacgggaa     960
gtggccaaaa ccgtcttttg cctggtcctt gtctttgccc tctgctggct tcccccttcac    1020 ctcagcagga ttctgaagct cactctttat aatcagaatg atcccaatag atgtgaactt    1080
ttgagctttc tgttggtatt ggactatatt ggtatcaaca tggcttcact gaattcctgc    1140
attaacccaa ttgctctgta tttggtgagc aaaagattca aaaactgctt taagtcatgc    1200
ttatgctgct ggtgccagtc atttgaagaa aaacagtcct ggaggaaaaa gcagtcgtgc    1260
ttaaagttca agctaatga tcacggatat gacaacttcc gttccagtaa taaatacagc    1320
tcatcttga                                                           1329

<210> SEQ ID NO 34
<211> LENGTH: 442
```

```
<212> TYPE: PRT
<213> ORGANISM: human

<400> SEQUENCE: 34

Met Gln Pro Pro Ser Leu Cys Gly Arg Ala Leu Val Ala Leu Val
1               5                   10                  15

Leu Ala Cys Gly Leu Ser Arg Ile Trp Gly Glu Arg Gly Phe Pro
                20                  25                  30

Pro Asp Arg Ala Thr Pro Leu Leu Gln Thr Ala Glu Ile Met Thr Pro
            35                  40                  45

Pro Thr Lys Thr Leu Trp Pro Lys Gly Ser Asn Ala Ser Leu Ala Arg
    50                  55                  60

Ser Leu Ala Pro Ala Glu Val Pro Lys Gly Asp Arg Thr Ala Gly Ser
65                  70                  75                  80

Pro Pro Arg Thr Ile Ser Pro Pro Cys Gln Gly Pro Ile Glu Ile
                85                  90                  95

Lys Glu Thr Phe Lys Tyr Ile Asn Thr Val Val Ser Cys Leu Val Phe
                100                 105                 110

Val Leu Gly Ile Ile Gly Asn Ser Thr Leu Leu Arg Ile Ile Tyr Lys
                115                 120                 125

Asn Lys Cys Met Arg Asn Gly Pro Asn Ile Leu Ile Ala Ser Leu Ala
                130                 135                 140

Leu Gly Asp Leu Leu His Ile Val Ile Asp Ile Pro Ile Asn Val Tyr
145                 150                 155                 160

Lys Leu Leu Ala Glu Asp Trp Pro Phe Gly Ala Glu Met Cys Lys Leu
                165                 170                 175

Val Pro Phe Ile Gln Lys Ala Ser Val Gly Ile Thr Val Leu Ser Leu
                180                 185                 190

Cys Ala Leu Ser Ile Asp Arg Tyr Arg Ala Val Ala Ser Trp Ser Arg
                195                 200                 205

Ile Lys Gly Ile Gly Val Pro Lys Trp Thr Ala Val Glu Ile Val Leu
                210                 215                 220

Ile Trp Val Val Ser Val Val Leu Ala Val Pro Glu Ala Ile Gly Phe
225                 230                 235                 240

Asp Ile Ile Thr Met Asp Tyr Lys Gly Ser Tyr Leu Arg Ile Cys Leu
                245                 250                 255

Leu His Pro Val Gln Lys Thr Ala Phe Met Gln Phe Tyr Lys Thr Ala
                260                 265                 270

Lys Asp Trp Trp Leu Phe Ser Phe Tyr Phe Cys Leu Pro Leu Ala Ile
                275                 280                 285

Thr Ala Phe Phe Tyr Thr Leu Met Thr Cys Glu Met Leu Arg Lys Lys
                290                 295                 300

Ser Gly Met Gln Ile Ala Leu Asn Asp His Leu Lys Gln Arg Arg Glu
305                 310                 315                 320

Val Ala Lys Thr Val Phe Cys Leu Val Leu Val Phe Ala Leu Cys Trp
                325                 330                 335

Leu Pro Leu His Leu Ser Arg Ile Leu Lys Leu Thr Leu Tyr Asn Gln
                340                 345                 350

Asn Asp Pro Asn Arg Cys Glu Leu Leu Ser Phe Leu Leu Val Leu Asp
                355                 360                 365

Tyr Ile Gly Ile Asn Met Ala Ser Leu Asn Ser Cys Ile Asn Pro Ile
                370                 375                 380

Ala Leu Tyr Leu Val Ser Lys Arg Phe Lys Asn Cys Phe Lys Ser Cys
385                 390                 395                 400
```

```
        Leu Cys Cys Trp Cys Gln Ser Phe Glu Glu Lys Gln Ser Leu Glu Glu
                        405                 410                 415

Lys Gln Ser Cys Leu Lys Phe Lys Ala Asn Asp His Gly Tyr Asp Asn
                    420                 425                 430

Phe Arg Ser Ser Asn Lys Tyr Ser Ser Ser
                    435                 440

<210> SEQ ID NO 35
<211> LENGTH: 2802
<212> TYPE: DNA
<213> ORGANISM: human

<400> SEQUENCE: 35
atgagagcgc tggctgtgct gtctgtcacg ctggttatgg cctgcacaga agccttcttc      60
cccttcatct cgagagggaa agaactcctt tggggaaagc tgaggagtc tcgtgtctct     120 agcgtcttgg aggaaagcaa gcgcctggtg acaccgcca tgtacgccac gatgcagaga     180
aacctcaaga aagaggaat cctttctgga gctcagcttc tgtcttttc caaacttcct     240 gagccaacaa gcggagtgat tgcccgagca gcagagataa tggaaacatc aatacaagcg     300
atgaaaagaa aagtcaacct gaaaactcaa caatcacagc atccaacgga tgctttatca     360
gaagatctgc tgagcatcat tgcaaacatg tctggatgtc tcccttacat gctgccccca     420
aaatgcccaa acacttgcct ggcgaacaaa tacaggccca tcacaggagc ttgcaacaac     480
agagaccacc ccagatgggg cgcctccaac acggccctgg cacgatggct ccctccagtc     540
tatgaggacg gcttcagtca gccccgaggc tggaaccccg gcttcttgta caacgggttc     600
ccactgcccc cggtccggga ggtgacaaga catgtcattc aagtttcaaa tgaggttgtc     660
acagatgatg accgctattc tgacctcctg atggcatggg acaatacat cgaccacgac     720 atcgcgttca caccacagag caccagcaaa gctgccttcg ggggagggtc tgactgccag     780
atgacttgtg agaaccaaaa cccatgtttt cccatacaac tcccggagga ggcccggccg     840
gccgcgggca ccgcctgtct gcccttctac cgctcttcgg ccgcctgcgg caccggggac     900
caaggcgcgc tctttgggaa cctgtccacg gccaacccga ggcagcagat gaacgggttg     960
acctcgttcc tggacgcgtc caccgtgtat ggcagctccc cggccctaga gaggcagctg    1020
cggaactgga ccagtgccga agggctgctc cgcgtccacg gccgcctccg ggactccggc    1080
cgcgcctacc tgcccttcgt gccgccacgc gcgcctgcgg cctgtgcgcc cgagcccggc    1140
aaccccggag agaccgcgg gccctgcttc ctggccggag acggccgcgc cagcgaggtc    1200
ccctccctga cggcactgca cacgctgtgg ctgcgcgagc acaaccgcct ggccgcggcg    1260
ctcaaggccc tcaatgcgca ctggagcgcg gacgccgtgt accaggaggc gcgcaaggtc    1320
gtgggcgctc tgcaccagat catcaccctg agggattaca tccccaggat cctgggaccc    1380
gaggccttcc agcagtacgt gggtccctat gaaggctatg actccaccgc caaccccact    1440
gtgtccaacg tgttctccac agccgccttc cgcttcggcc atgccacgat ccaccgctg    1500 gtgaggaggc tggacgccag cttccaggag caccccgacc tgcccgggct gtggctgcac    1560
caggctttct tcagcccatg gacattactc cgtggaggtg gtttggaccc actaatacga    1620
ggccttcttg caagaccagc caaactgcag gtgcaggatc agctgatgaa cgaggagctg    1680
acggaaaggc tctttgtgct gtccaattcc agcaccttgg atctgcgtc catcaacctg    1740 cagaggggcc gggaccacgg gctgccaggt acaatgagt ggagggagtt ctgcggcctg    1800
cctcgcctgg agaccccgc tgacctgagc acagccatcg ccagcaggag cgtggccgac    1860
aagatcctgg acttgtacaa gcatcctgac aacatcgatg tctggctggg aggcttagct    1920
```

-continued

```
gaaaacttcc tccccagggc tcggacaggg ccctgttttg cctgtctcat tgggaagcag    1980
atgaaggctc tgcgggacgg tgactggttt tggtgggaga acagccacgt cttcacggat    2040
gcacagaggc gtgagctgga gaagcactcc ctgtctcggg tcatctgtga caacactggc    2100
ctcaccaggg tgcccatgga tgccttccaa gtcggcaaat tccccgaaga ctttgagtct    2160
tgtgacagca tcactggcat gaacctggag gcctggaggg aaacctttcc tcaagacgac    2220
aagtgtggct tcccagagag cgtggagaat ggggactttg tgcactgtga ggagtctggg    2280
aggcgcgtgc tggtgtattc ctgccggcac gggtatgagc tccaaggccg ggagcagctc    2340
acttgcaccc aggaaggatg ggatttccag cctcccctct gcaaagatgt gaacgagtgt    2400
gcagacggtg cccaccccc ctgccacgcc tctgcgaggt gcagaaacac caaaggcggc    2460
ttccagtgtc tctgcgcgga cccctacgag ttaggagacg atgggagaac ctgcgtagac    2520
tccgggaggc tccctcgggt gacttggatc tccatgtcgc tggctgctct gctgatcgga    2580
ggcttcgcag gtctcacctc gacggtgatt tgcaggtgga cacgcactgg cactaaatcc    2640
acactgccca tctcggagac aggcggagga actcccgagc tgagatgcgg aaagcaccag    2700
gccgtaggga cctcaccgca gcgggccgca gctcaggact cggagcagga gagtgctggg    2760
atggaaggcc gggatactca caggctgccg agagccctct ga                       2802
```

```
<210> SEQ ID NO 36
<211> LENGTH: 933
<212> TYPE: PRT
<213> ORGANISM: human

<400> SEQUENCE: 36
```

```
Met Arg Ala Leu Ala Val Leu Ser Val Thr Leu Val Met Ala Cys Thr
1               5                   10                  15

Glu Ala Phe Phe Pro Phe Ile Ser Arg Gly Lys Glu Leu Leu Trp Gly
            20                  25                  30

Lys Pro Glu Glu Ser Arg Val Ser Val Leu Glu Glu Ser Lys Arg
        35                  40                  45

Leu Val Asp Thr Ala Met Tyr Ala Thr Met Gln Arg Asn Leu Lys Lys
    50                  55                  60

Arg Gly Ile Leu Ser Gly Ala Gln Leu Leu Ser Phe Ser Lys Leu Pro
65                  70                  75                  80

Glu Pro Thr Ser Gly Val Ile Ala Arg Ala Ala Glu Ile Met Glu Thr
                85                  90                  95

Ser Ile Gln Ala Met Lys Arg Lys Val Asn Leu Lys Thr Gln Gln Ser
            100                 105                 110

Gln His Pro Thr Asp Ala Leu Ser Glu Asp Leu Leu Ser Ile Ile Ala
        115                 120                 125

Asn Met Ser Gly Cys Leu Pro Tyr Met Leu Pro Pro Lys Cys Pro Asn
    130                 135                 140

Thr Cys Leu Ala Asn Lys Tyr Arg Pro Ile Thr Gly Ala Cys Asn Asn
145                 150                 155                 160

Arg Asp His Pro Arg Trp Gly Ala Ser Asn Thr Ala Leu Ala Arg Trp
                165                 170                 175

Leu Pro Pro Val Tyr Glu Asp Gly Phe Ser Gln Pro Arg Gly Trp Asn
            180                 185                 190

Pro Gly Phe Leu Tyr Asn Gly Phe Pro Leu Pro Pro Val Arg Glu Val
        195                 200                 205

Thr Arg His Val Ile Gln Val Ser Asn Glu Val Val Thr Asp Asp Asp
    210                 215                 220
```

-continued

```
Arg Tyr Ser Asp Leu Leu Met Ala Trp Gly Gln Tyr Ile Asp His Asp
225                 230                 235                 240

Ile Ala Phe Thr Pro Gln Ser Thr Ser Lys Ala Ala Phe Gly Gly Gly
                245                 250                 255

Ser Asp Cys Gln Met Thr Cys Glu Asn Gln Asn Pro Cys Phe Pro Ile
            260                 265                 270

Gln Leu Pro Glu Glu Ala Arg Pro Ala Ala Gly Thr Ala Cys Leu Pro
        275                 280                 285

Phe Tyr Arg Ser Ser Ala Ala Cys Gly Thr Gly Asp Gln Gly Ala Leu
    290                 295                 300

Phe Gly Asn Leu Ser Thr Ala Asn Pro Arg Gln Gln Met Asn Gly Leu
305                 310                 315                 320

Thr Ser Phe Leu Asp Ala Ser Thr Val Tyr Gly Ser Ser Pro Ala Leu
                325                 330                 335

Glu Arg Gln Leu Arg Asn Trp Thr Ser Ala Glu Gly Leu Leu Arg Val
                340                 345                 350

His Gly Arg Leu Arg Asp Ser Gly Arg Ala Tyr Leu Pro Phe Val Pro
            355                 360                 365

Pro Arg Ala Pro Ala Ala Cys Ala Pro Glu Pro Gly Asn Pro Gly Glu
        370                 375                 380

Thr Arg Gly Pro Cys Phe Leu Ala Gly Asp Gly Arg Ala Ser Glu Val
385                 390                 395                 400

Pro Ser Leu Thr Ala Leu His Thr Leu Trp Leu Arg Glu His Asn Arg
                405                 410                 415

Leu Ala Ala Ala Leu Lys Ala Leu Asn Ala His Trp Ser Ala Asp Ala
                420                 425                 430

Val Tyr Gln Glu Ala Arg Lys Val Val Gly Ala Leu His Gln Ile Ile
            435                 440                 445

Thr Leu Arg Asp Tyr Ile Pro Arg Ile Leu Gly Pro Glu Ala Phe Gln
450                 455                 460

Gln Tyr Val Gly Pro Tyr Glu Gly Tyr Asp Ser Thr Ala Asn Pro Thr
465                 470                 475                 480

Val Ser Asn Val Phe Ser Thr Ala Ala Phe Arg Phe Gly His Ala Thr
                485                 490                 495

Ile His Pro Leu Val Arg Arg Leu Asp Ala Ser Phe Gln Glu His Pro
            500                 505                 510

Asp Leu Pro Gly Leu Trp Leu His Gln Ala Phe Phe Ser Pro Trp Thr
        515                 520                 525

Leu Leu Arg Gly Gly Gly Leu Asp Pro Leu Ile Arg Gly Leu Leu Ala
    530                 535                 540

Arg Pro Ala Lys Leu Gln Val Gln Asp Gln Leu Met Asn Glu Glu Leu
545                 550                 555                 560

Thr Glu Arg Leu Phe Val Leu Ser Asn Ser Ser Thr Leu Asp Leu Ala
                565                 570                 575

Ser Ile Asn Leu Gln Arg Gly Arg Asp His Gly Leu Pro Gly Tyr Asn
            580                 585                 590

Glu Trp Arg Glu Phe Cys Gly Leu Pro Arg Leu Glu Thr Pro Ala Asp
        595                 600                 605

Leu Ser Thr Ala Ile Ala Ser Arg Ser Val Ala Asp Lys Ile Leu Asp
    610                 615                 620

Leu Tyr Lys His Pro Asp Asn Ile Asp Val Trp Leu Gly Gly Leu Ala
625                 630                 635                 640

Glu Asn Phe Leu Pro Arg Ala Arg Thr Gly Pro Leu Phe Ala Cys Leu
```

645                 650                 655
Ile Gly Lys Gln Met Lys Ala Leu Arg Asp Gly Asp Trp Phe Trp
            660                 665                 670

Glu Asn Ser His Val Phe Thr Asp Ala Gln Arg Arg Glu Leu Glu Lys
            675                 680                 685

His Ser Leu Ser Arg Val Ile Cys Asp Asn Thr Gly Leu Thr Arg Val
            690                 695                 700

Pro Met Asp Ala Phe Gln Val Gly Lys Phe Pro Glu Asp Phe Glu Ser
705                 710                 715                 720

Cys Asp Ser Ile Thr Gly Met Asn Leu Glu Ala Trp Arg Glu Thr Phe
                725                 730                 735

Pro Gln Asp Asp Lys Cys Gly Phe Pro Glu Ser Val Glu Asn Gly Asp
            740                 745                 750

Phe Val His Cys Glu Glu Ser Gly Arg Arg Val Leu Val Tyr Ser Cys
            755                 760                 765

Arg His Gly Tyr Glu Leu Gln Gly Arg Glu Gln Leu Thr Cys Thr Gln
            770                 775                 780

Glu Gly Trp Asp Phe Gln Pro Pro Leu Cys Lys Asp Val Asn Glu Cys
785                 790                 795                 800

Ala Asp Gly Ala His Pro Pro Cys His Ala Ser Ala Arg Cys Arg Asn
                805                 810                 815

Thr Lys Gly Gly Phe Gln Cys Leu Cys Ala Asp Pro Tyr Glu Leu Gly
            820                 825                 830

Asp Asp Gly Arg Thr Cys Val Asp Ser Gly Arg Leu Pro Arg Val Thr
            835                 840                 845

Trp Ile Ser Met Ser Leu Ala Ala Leu Leu Ile Gly Gly Phe Ala Gly
850                 855                 860

Leu Thr Ser Thr Val Ile Cys Arg Trp Thr Arg Thr Gly Thr Lys Ser
865                 870                 875                 880

Thr Leu Pro Ile Ser Glu Thr Gly Gly Thr Pro Glu Leu Arg Cys
            885                 890                 895

Gly Lys His Gln Ala Val Gly Thr Ser Pro Gln Arg Ala Ala Ala Gln
            900                 905                 910

Asp Ser Glu Gln Glu Ser Ala Gly Met Glu Gly Arg Asp Thr His Arg
            915                 920                 925

Leu Pro Arg Ala Leu
        930

<210> SEQ ID NO 37
<211> LENGTH: 8304
<212> TYPE: DNA
<213> ORGANISM: human

<400> SEQUENCE: 37
atggccctgg tcctggagat cttcaccctg ctggcctcca tctgctgggt gtcggccaat      60
atcttcgagt accaggttga tgcccagccc cttcgtccct gtgagctgca gagggaaacg     120
gcctttctga agcaagcaga ctacgtgccc cagtgtgcag aggatggcag cttccagact     180
gtccagtgcc agaacgacgg ccgctcctgc tggtgtgtgg gtgccaacgg cagtgaagtg     240
ctgggcagca gcagccagg acggcctgtg gcttgtctgt cattttgtca gctacagaaa     300
cagcagatct tactgagtgg ctacattaac agcacagaca cctcctacct ccctcagtgt     360
caggattcag gggactacgc gcctgttcag tgtgatgtgc agcatgtcca gtgctggtgt     420
gtggacgcag aggggatgga ggtgtatggg acccgccagc tggggaggcc aaagcgatgt     480

-continued

```
ccaaggagct gtgaaataag aaatcgtcgt cttctccacg gggtgggaga taagtcacca      540
ccccagtgtt ctgcggaggg agagtttatg cctgtccagt gcaaatttgt caacaccaca      600
gacatgatga ttttttgatct ggtccacagc tacaacaggt ttccagatgc atttgtgacc     660
ttcagttcct tccagaggag gttccctgag gtatctgggg attgccactg tgctgacagc      720
caagggcggg aactggctga gacaggtttg gagttgttac tggatgaaat ttatgacacc      780 attttttgctg gcctggacct tccttccacc ttcactgaaa ccaccctgta ccggatactg      840
cagagacggt tcctcgcagt tcaatcagtc atctctggca gattccgatg ccccacaaaa      900
tgtgaagtgg agcggtttac agcaaccagc tttggtcacc cctatgttcc aagctgccgc      960
cgaaatggcg actatcaggc ggtgcagtgc cagacggaag ggccctgctg gtgtgtggac     1020
gcccagggga aggaaatgca tggaacccgg cagcaagggg agccgccatc ttgtgctgaa     1080
ggccaatctt gtgcctccga aaggcagcag gccttgtcca gactctactt tgggacctca     1140
ggctacttca gccagcacga cctgttctct tccccagaga aaagatgggc ctctccaaga     1200
gtagccagat ttgccacatc ctgcccaccc acgatcaagg agctctttgt ggactctggg     1260
cttctccgcc caatggtgga gggacagagc caacagtttt ctgtctcaga aaatcttctc     1320
aaagaagcca tccgagcaat ttttccctcc cgagggctgg ctcgtcttgc ccttcagttt     1380
accaccaacc caaagagact ccagcaaaac cttttttggag ggaaattttt ggtgaatgtt    1440
ggccagttta acttgtctgg agcccttggc acaagaggca catttaactt cagtcaattt     1500
ttccagcaac ttggtcttgc aagcttcttg aatggaggga dacaagaaga tttggccaag     1560
ccactctctg tgggattaga ttcaaattct tccacaggaa cccctgaagc tgctaagaag     1620
gatggtacta tgaataagcc aactgtgggc agctttggct ttgaaattaa cctacaagag     1680
aaccaaaatg ccctcaaatt ccttgcttct ctcctggagc ttccagaatt ccttctcttc     1740
ttgcaacatg ctatctctgt gccagaagat gtggcaagag atttaggtga tgtgatggaa     1800
acggtactcg actcccagac ctgtgagcag acacctgaaa ggctatttgt cccatcatgc     1860
acgacagaag gaagctatga ggatgtccaa tgcttttccg gagagtgctg gtgtgtgaat     1920
tcctggggca aagagcttcc aggctcaaga gtcagagatg gacagccaag gtgccccaca     1980
gactgtgaaa agcaaagggc tcgcatgcaa agcctcatgg gcagccagcc tgctggctcc     2040
accttgtttg tccctgcttg tactagtgag ggacatttcc tgcctgtcca gtgcttcaac     2100
tcagagtgct actgtgttga tgctgagggt caggccattc ctggaactcg aagtgcaata     2160
gggaagccca gaaatgcccc cacgcccgt caattacagt ctgagcaagc tttcctcagg     2220
acggtgcagg ccctgctctc taactccagc atgctaccca cccttttccga cacctacatc     2280 ccacagtgca gcaccgatgg gcagtggaga caagtgcaat gcaatgggcc tcctgagcag     2340
gtcttcgagt tgtaccaacg atgggaggct cagaacaagg gccaggatct gacgcctgcc     2400
aagctgctag tgaagatcat gagctacaga gaagcagctt ccggaaactt cagtctcttt     2460
attcaaagtc tgtatgaggc tggccagcaa gatgtcttcc cggtgctgtc acaatacccct    2520 tctctgcaag atgtcccact agcagcactg gaagggaaac ggccccagcc cagggagaat     2580
atcctcctgg agccctacct cttctggcag atcttaaatg ccaactcag ccaatacccg      2640 gggtcctact cagacttcag cactcctttg gcacattttg atcttcggaa ctgctggtgt     2700
gtggatgagg ctggccaaga actggaagga atgcggtctg agccaagcaa gctcccaacg     2760
tgtcctggct cctgtgagga agcaaagctc cgtgtactgc agttcattag ggaaacggaa     2820
gagattgttt cagcttccaa cagttctcgg ttccctctgg gggagagttt cctggtggcc     2880
```

```
aagggaatcc ggctgaggaa tgaggacctc ggccttcctc cgctcttccc gccccgggag   2940
gctttcgcgg agtttctgcg tgggagtgat tacgccattc gcctggcggc tcagtctacc   3000
ttaagcttct atcagagacg ccgcttttcc ccggacgact cggctggagc atccgccctt   3060
ctgcggtcgg gccctacat gccacagtgt gatgcgtttg gaagttggga gcctgtgcag   3120
tgccacgctg ggactgggca ctgctggtgt gtagatgaga aggagggtt catccctggc   3180 tcactgactg cccgctctct gcagattcca cagtgcccga caacctgcga gaaatctcga   3240
accagtgggc tgctttccag ttggaaacag gctagatccc aagaaaaccc atctccaaaa   3300
gacctgttcg tcccagcctg cctagaaaca ggagaatatg ccaggctgca ggcatcgggg   3360
gctggcacct ggtgtgtgga ccctgcatca ggagaagagt tgcggcctgg ctcgagcagc   3420
agtgcccagt gcccaagcct ctgcaatgtg ctcaagagtg gagtcctctc taggagagtc   3480
agcccaggct atgtcccagc ctgcagggca gaggatgggg gcttttcccc agtgcaatgt   3540
gaccaggccc agggcagctg ctggtgtgtc atggacagcg gagaagaggt gcctgggacg   3600
cgcgtgaccg ggggccagcc cgcctgtgag agcccgcggt gtccgctgcc attcaacgcg   3660
tcggaggtgg ttggtggaac aatcctgtgt gagacaatct cgggcccac aggctctgcc   3720 atgcagcagt gccaattgct gtgccgccaa ggctcctgga gcgtgtttcc accagggcca   3780
ttgatatgta gcctggagag cggacgctgg gagtcacagc tgcctcagcc ccgggcctgc   3840
caacggcccc agctgtggca gaccatccag acccaagggc actttcagct ccagctcccg   3900
ccgggcaaga tgtgcagtgc tgactacgcg ggtttgctgc agactttcca ggttttcata   3960
ttggatgagc tgacagcccg cggcttctgc cagatccagg tgaagacttt tggcaccctg   4020
gtttccattc ctgtctgcaa caactcctct gtgcaggtgg gttgtctgac cagggagcgt   4080
ttaggagtga atgttacatg gaaatcacgg cttgaggaca tcccagtggc ttctcttcct   4140
gacttacatg acattgagag agccttggtg ggcaaggatc tccttgggcg cttcacagat   4200
ctgatccaga gtggctcatt ccagcttcat ctggactcca agacgttccc agcggaaacc   4260
atccgcttcc tccaagggga ccactttggc acctctccta ggacacggtt tgggtgctcg   4320
gaaggattct accaagtctt gacaagtgag gccagtcagg acggactggg atgcgttaag   4380
tgccatgaag gaagctattc ccaagatgag gaatgcattc cttgtcctgt tggattctac   4440
caagaacagg cagggagctt ggcctgtgtc ccatgtcctg tgggcagaac gaccatttct   4500
gccggagctt tcagccagac tcactgtgtc actgactgtc agaggaacga agcaggcctg   4560
caatgtgacc agaatggcca gtatcgagcc agccagaagg acaggggcag tgggaaggcc   4620
ttctgtgtgg acggcgaggg gcggaggctg ccatggtggg aaacagaggc ccctcttgag   4680
gactcacagt gtttgatgat gcagaagttt gagaaggttc cagaatcaaa ggtgatcttc   4740
gacgccaatg ctcctgtggc tgtcagatcc aaagttcctg attctgagtt ccccgtgatg   4800
cagtgcttga cagattgcac agaggacgag gcctgcagct tcttcaccgt gtccacgacg   4860
gagccagaga tttcctgtga tttctatgct tggacaagtg acaatgttgc ctgcatgact   4920
tctgaccaga aacgagatgc actgggaac tcaaaggcca ccagctttgg aagtcttcgc   4980
tgccaggtga agtgaggag ccatggtcaa gattctccag ctgtgtattt gaaaaagggc   5040
caaggatcca ccacaacact tcagaaacgc tttgaaccca ctggtttcca aaacatgctt   5100
tctggattgt acaaccccat tgtgttctca gcctcaggag ccaatctaac cgatgctcac   5160
ctcttctgtc ttcttgcatg cgaccgtgat ctgtgttgcg atggcttcgt cctcacacag   5220
gttcaaggag gtgccatcat ctgtgggttg ctgagctcac ccagtgtcct gctttgtaat   5280
```

```
gtcaaagact ggatggatcc ctctgaagcc tgggctaatg ctacatgtcc tggtgtgaca   5340
tatgaccagg agagccacca ggtgatattg cgtcttggag accaggagtt catcaagagt   5400
ctgacaccct tagaaggaac tcaagacacc tttaccaatt ttcagcaggt ttatctctgg   5460
aaagattctg acatggggtc tcggcctgag tctatgggat gtagaaaaaa cacagtgcca   5520
aggccagcat ctccaacaga agcaggtttg acaacagaac ttttctcccc tgtggacctc   5580
aaccaggtca ttgtcaatgg aaatcaatca ctatccagcc agaagcactg gcttttcaag   5640
cacctgtttt cagcccagca ggcaaaccta tggtgccttt ctcgttgtgt gcaggagcac   5700
tctttctgtc agctcgcaga gataacagag agtgcatcct tgtacttcac ctgcaccctc   5760
tacccagagg cacaggtgtg tgatgacatc atggagtcca atacccaggg ctgcagactg   5820
atcctgcctc agatgccaaa ggccctgttc cggaagaaag ttatactgga agataaagtg   5880
aagaactttt acactcgcct gccgttccaa aaactgatgg ggatatccat tagaaataaa   5940
gtgcccatgt ctgaaaaatc tatttctaat gggttctttg aatgtgaacg acggtgcgat   6000
gcggacccat gctgcactgg ctttggatttt ctaaatgttt cccagttaaa aggaggagag   6060
gtgacatgtc tcactctgaa cagcttggga attcagatgt gcagtgagga aatggagga   6120
gcctggcgca ttttggactg tggctctcct gacattgaag tccacaccta tcccttcgga   6180
tggtaccaga agcccattgc tcaaaataat gctcccagtt tttgcccttt ggttgttctg   6240
ccttccctca cagagaaagt gtctctggaa tcgtggcagt ccctggccct ctcttcagtg   6300
gttgttgatc catccattag gcactttgat gttgcccatg tcagcactgc tgccaccagc   6360
aatttctctg ctgtccgaga cctctgtttg tcggaatgtt cccaacatga ggcctgtctc   6420
atcaccactc tgcaaaccca actcggggct gtgagatgta tgttctatgc tgatactcaa   6480
agctgcacac atagtctgca gggtcggaac tgccgacttc tgcttcgtga agaggccacc   6540
cacatctacc ggaagccagg aatctctctg ctcagctatg aggcatctgt accttctgtg   6600
cccatttcca cccatggccg gctgctgggc aggtcccagg ccatccaggt gggtacctca   6660
tggaagcaag tggaccagtt ccttggagtt ccatatgctg ccccgcccct ggcagagagg   6720
cacttccagg caccagagcc cttgaactgg acaggctcct gggatgccag caagccaagg   6780
gccagctgct ggcagccagg caccagaaca tccacgtctc ctggagtcag tgaagattgt   6840
ttgtatctca atgtgttcat ccctcagaat gtggccccta acgcgtctgt gctggtgttc   6900
ttccacaaca ccatggacag ggaggagagt gaaggatggc cggctatcga cggctccttc   6960
ttggctgctg ttggcaacct catcgtggtc actgccagct accgagtggg tgtcttcggc   7020
ttcctgagtt ctggatccgg agaggtgagt ggcaactggg ggctgctgga ccaggtggcg   7080
gctctgacct gggtgcagac ccacatccga ggatttggcg gggaccctcg gcgcgtgtcc   7140
ctggcagcag accgtggcgg ggctgatgtg gccagcatcc accttctcac ggccagggcc   7200
accaactccc aacttttccg gagagctgtg ctgatgggag gctccgcact ctccccggcc   7260
gccgtcatca gccatgagag ggctcagcag caggcaattg ctttggcaaa ggaggtcagt   7320
tgccccatgt catccagcca agaagtggtg tcctgcctcc gccagaagcc tgccaatgtc   7380
ctcaatgatg cccagaccaa gctcctggcc gtgagtggcc ctttccacta ctggggtcct   7440
gtgatcgatg gccacttcct ccgtgagcct ccagccagag cactgaagag gtctttatgg   7500
gtagaggtcg atctgctcat tgggagttct caggacgacg ggctcatcaa cagagcaaag   7560
gctgtgaagc aatttgagga aagtcgaggc cggaccagta gcaaaacagc cttttaccag   7620
gcactgcaga attctctggg tggcgaggac tcagatgccc gcgtcgaggc tgctgctaca   7680
```

-continued

```
tggtattact ctctggagca ctccacggat gactatgcct ccttctcccg ggctctggag    7740
aatgccaccc gggactactt tatcatctgc cctataatcg acatggccag tgcctgggca    7800
aagagggccc gaggaaacgt cttcatgtac catgctcctg aaaactacgg ccatggcagc    7860
ctggagctgc tggcgatgt tcagtttgcc ttggggcttc ccttctaccc agcctacgag    7920
gggcagtttt ctctggagga gaagagcctg tcgctgaaaa tcatgcagta cttttcccac    7980
ttcatcagat caggaaatcc caactaccct tatgagttct cacggaaagt acccacattt    8040
gcaaccccct ggcctgactt tgtaccccgt gctggtggag agaactacaa ggagttcagt    8100
gagctgctcc ccaatcgaca gggcctgaag aaagccgact gctccttctg gtccaagtac    8160
atctcgtctc tgaagacatc tgcagatgga gccaagggcg ggcagtcagc agagagtgaa    8220
gaggaggagt tgacggctgg atctgggcta agagaagatc tcctaagcct ccaggaacca    8280
ggctctaaga cctacagcaa gtga                                            8304
```

<210> SEQ ID NO 38
<211> LENGTH: 2767
<212> TYPE: PRT
<213> ORGANISM: human

<400> SEQUENCE: 38

```
Met Ala Leu Val Leu Glu Ile Phe Thr Leu Leu Ala Ser Ile Cys Trp
1               5                   10                  15

Val Ser Ala Asn Ile Phe Glu Tyr Gln Val Asp Ala Gln Pro Leu Arg
            20                  25                  30

Pro Cys Glu Leu Gln Arg Glu Thr Ala Phe Leu Lys Gln Ala Asp Tyr
        35                  40                  45

Val Pro Gln Cys Ala Glu Asp Gly Ser Phe Gln Thr Val Gln Cys Gln
    50                  55                  60

Asn Asp Gly Arg Ser Cys Trp Cys Val Gly Ala Asn Gly Ser Glu Val
65                  70                  75                  80

Leu Gly Ser Arg Gln Pro Gly Arg Pro Val Ala Cys Leu Ser Phe Cys
                85                  90                  95

Gln Leu Gln Lys Gln Gln Ile Leu Leu Ser Gly Tyr Ile Asn Ser Thr
            100                 105                 110

Asp Thr Ser Tyr Leu Pro Gln Cys Gln Asp Ser Gly Asp Tyr Ala Pro
        115                 120                 125

Val Gln Cys Asp Val Gln His Val Gln Cys Trp Cys Val Asp Ala Glu
    130                 135                 140

Gly Met Glu Val Tyr Gly Thr Arg Gln Leu Gly Arg Pro Lys Arg Cys
145                 150                 155                 160

Pro Arg Ser Cys Glu Ile Arg Asn Arg Arg Leu Leu His Gly Val Gly
                165                 170                 175

Asp Lys Ser Pro Pro Gln Cys Ser Ala Glu Gly Glu Phe Met Pro Val
            180                 185                 190

Gln Cys Lys Phe Val Asn Thr Thr Asp Met Met Ile Phe Asp Leu Val
        195                 200                 205

His Ser Tyr Asn Arg Phe Pro Asp Ala Phe Val Thr Phe Ser Ser Phe
    210                 215                 220

Gln Arg Arg Phe Pro Glu Val Ser Gly Tyr Cys His Cys Ala Asp Ser
225                 230                 235                 240

Gln Gly Arg Glu Leu Ala Glu Thr Gly Leu Glu Leu Leu Leu Asp Glu
                245                 250                 255

Ile Tyr Asp Thr Ile Phe Ala Gly Leu Asp Leu Pro Ser Thr Phe Thr
            260                 265                 270
```

Glu Thr Thr Leu Tyr Arg Ile Leu Gln Arg Arg Phe Leu Ala Val Gln
            275                 280                 285
Ser Val Ile Ser Gly Arg Phe Arg Cys Pro Thr Lys Cys Glu Val Glu
            290                 295                 300
Arg Phe Thr Ala Thr Ser Phe Gly His Pro Tyr Val Pro Ser Cys Arg
305                 310                 315                 320
Arg Asn Gly Asp Tyr Gln Ala Val Gln Cys Gln Thr Glu Gly Pro Cys
            325                 330                 335
Trp Cys Val Asp Ala Gln Gly Lys Glu Met His Gly Thr Arg Gln Gln
            340                 345                 350
Gly Glu Pro Pro Ser Cys Ala Glu Gly Gln Ser Cys Ala Ser Glu Arg
            355                 360                 365
Gln Gln Ala Leu Ser Arg Leu Tyr Phe Gly Thr Ser Gly Tyr Phe Ser
            370                 375                 380
Gln His Asp Leu Phe Ser Ser Pro Glu Lys Arg Trp Ala Ser Pro Arg
385                 390                 395                 400
Val Ala Arg Phe Ala Thr Ser Cys Pro Pro Thr Ile Lys Glu Leu Phe
            405                 410                 415
Val Asp Ser Gly Leu Leu Arg Pro Met Val Glu Gly Gln Ser Gln Gln
            420                 425                 430
Phe Ser Val Ser Glu Asn Leu Leu Lys Glu Ala Ile Arg Ala Ile Phe
            435                 440                 445
Pro Ser Arg Gly Leu Ala Arg Leu Ala Leu Gln Phe Thr Thr Asn Pro
            450                 455                 460
Lys Arg Leu Gln Gln Asn Leu Phe Gly Gly Lys Phe Leu Val Asn Val
465                 470                 475                 480
Gly Gln Phe Asn Leu Ser Gly Ala Leu Gly Thr Arg Gly Thr Phe Asn
            485                 490                 495
Phe Ser Gln Phe Phe Gln Gln Leu Gly Leu Ala Ser Phe Leu Asn Gly
            500                 505                 510
Gly Arg Gln Glu Asp Leu Ala Lys Pro Leu Ser Val Gly Leu Asp Ser
            515                 520                 525
Asn Ser Ser Thr Gly Thr Pro Glu Ala Ala Lys Lys Asp Gly Thr Met
            530                 535                 540
Asn Lys Pro Thr Val Gly Ser Phe Gly Phe Glu Ile Asn Leu Gln Glu
545                 550                 555                 560
Asn Gln Asn Ala Leu Lys Phe Leu Ala Ser Leu Leu Glu Leu Pro Glu
            565                 570                 575
Phe Leu Leu Phe Leu Gln His Ala Ile Ser Val Pro Glu Asp Val Ala
            580                 585                 590
Arg Asp Leu Gly Asp Val Met Glu Thr Val Leu Asp Ser Gln Thr Cys
            595                 600                 605
Glu Gln Thr Pro Glu Arg Leu Phe Val Pro Ser Cys Thr Thr Glu Gly
            610                 615                 620
Ser Tyr Glu Asp Val Gln Cys Phe Ser Gly Glu Cys Trp Cys Val Asn
625                 630                 635                 640
Ser Trp Gly Lys Glu Leu Pro Gly Ser Arg Val Arg Asp Gly Gln Pro
            645                 650                 655
Arg Cys Pro Thr Asp Cys Glu Lys Gln Arg Ala Arg Met Gln Ser Leu
            660                 665                 670
Met Gly Ser Gln Pro Ala Gly Ser Thr Leu Phe Val Pro Ala Cys Thr
            675                 680                 685
Ser Glu Gly His Phe Leu Pro Val Gln Cys Phe Asn Ser Glu Cys Tyr

-continued

```
                690                 695                 700
Cys Val Asp Ala Glu Gly Gln Ala Ile Pro Gly Thr Arg Ser Ala Ile
705                 710                 715                 720

Gly Lys Pro Lys Lys Cys Pro Thr Pro Cys Gln Leu Gln Ser Glu Gln
                725                 730                 735

Ala Phe Leu Arg Thr Val Gln Ala Leu Leu Ser Asn Ser Ser Met Leu
                740                 745                 750

Pro Thr Leu Ser Asp Thr Tyr Ile Pro Gln Cys Ser Thr Asp Gly Gln
                755                 760                 765

Trp Arg Gln Val Gln Cys Asn Gly Pro Pro Glu Gln Val Phe Glu Leu
                770                 775                 780

Tyr Gln Arg Trp Glu Ala Gln Asn Lys Gly Gln Asp Leu Thr Pro Ala
785                 790                 795                 800

Lys Leu Leu Val Lys Ile Met Ser Tyr Arg Glu Ala Ala Ser Gly Asn
                805                 810                 815

Phe Ser Leu Phe Ile Gln Ser Leu Tyr Glu Ala Gly Gln Gln Asp Val
                820                 825                 830

Phe Pro Val Leu Ser Gln Tyr Pro Ser Leu Gln Asp Val Pro Leu Ala
                835                 840                 845

Ala Leu Glu Gly Lys Arg Pro Gln Pro Arg Glu Asn Ile Leu Leu Glu
850                 855                 860

Pro Tyr Leu Phe Trp Gln Ile Leu Asn Gly Gln Leu Ser Gln Tyr Pro
865                 870                 875                 880

Gly Ser Tyr Ser Asp Phe Ser Thr Pro Leu Ala His Phe Asp Leu Arg
                885                 890                 895

Asn Cys Trp Cys Val Asp Glu Ala Gly Gln Glu Leu Glu Gly Met Arg
                900                 905                 910

Ser Glu Pro Ser Lys Leu Pro Thr Cys Pro Gly Ser Cys Glu Glu Ala
                915                 920                 925

Lys Leu Arg Val Leu Gln Phe Ile Arg Glu Thr Glu Glu Ile Val Ser
                930                 935                 940

Ala Ser Asn Ser Ser Arg Phe Pro Leu Gly Glu Ser Phe Leu Val Ala
945                 950                 955                 960

Lys Gly Ile Arg Leu Arg Asn Glu Asp Leu Gly Leu Pro Pro Leu Phe
                965                 970                 975

Pro Pro Arg Glu Ala Phe Ala Glu Phe Leu Arg Gly Ser Asp Tyr Ala
                980                 985                 990

Ile Arg Leu Ala Ala Gln Ser Thr Leu Ser Phe Tyr Gln Arg Arg Arg
                995                 1000                1005

Phe Ser Pro Asp Asp Ser Ala Gly Ala Ser Ala Leu Leu Arg Ser
                1010                1015                1020

Gly Pro Tyr Met Pro Gln Cys Asp Ala Phe Gly Ser Trp Glu Pro
                1025                1030                1035

Val Gln Cys His Ala Gly Thr Gly His Cys Trp Cys Val Asp Glu
                1040                1045                1050

Lys Gly Gly Phe Ile Pro Gly Ser Leu Thr Ala Arg Ser Leu Gln
                1055                1060                1065

Ile Pro Gln Cys Pro Thr Thr Cys Glu Lys Ser Arg Thr Ser Gly
                1070                1075                1080

Leu Leu Ser Ser Trp Lys Gln Ala Arg Ser Gln Glu Asn Pro Ser
                1085                1090                1095

Pro Lys Asp Leu Phe Val Pro Ala Cys Leu Glu Thr Gly Glu Tyr
                1100                1105                1110
```

```
Ala Arg Leu Gln Ala Ser Gly Ala Gly Thr Trp Cys Val Asp Pro
1115                1120                1125

Ala Ser Gly Glu Glu Leu Arg Pro Gly Ser Ser Ser Ser Ala Gln
1130                1135                1140

Cys Pro Ser Leu Cys Asn Val Leu Lys Ser Gly Val Leu Ser Arg
1145                1150                1155

Arg Val Ser Pro Gly Tyr Val Pro Ala Cys Arg Ala Glu Asp Gly
1160                1165                1170

Gly Phe Ser Pro Val Gln Cys Asp Gln Ala Gln Gly Ser Cys Trp
1175                1180                1185

Cys Val Met Asp Ser Gly Glu Glu Val Pro Gly Thr Arg Val Thr
1190                1195                1200

Gly Gly Gln Pro Ala Cys Glu Ser Pro Arg Cys Pro Leu Pro Phe
1205                1210                1215

Asn Ala Ser Glu Val Val Gly Gly Thr Ile Leu Cys Glu Thr Ile
1220                1225                1230

Ser Gly Pro Thr Gly Ser Ala Met Gln Gln Cys Gln Leu Leu Cys
1235                1240                1245

Arg Gln Gly Ser Trp Ser Val Phe Pro Pro Gly Pro Leu Ile Cys
1250                1255                1260

Ser Leu Glu Ser Gly Arg Trp Glu Ser Gln Leu Pro Gln Pro Arg
1265                1270                1275

Ala Cys Gln Arg Pro Gln Leu Trp Gln Thr Ile Gln Thr Gln Gly
1280                1285                1290

His Phe Gln Leu Gln Leu Pro Pro Gly Lys Met Cys Ser Ala Asp
1295                1300                1305

Tyr Ala Gly Leu Leu Gln Thr Phe Gln Val Phe Ile Leu Asp Glu
1310                1315                1320

Leu Thr Ala Arg Gly Phe Cys Gln Ile Gln Val Lys Thr Phe Gly
1325                1330                1335

Thr Leu Val Ser Ile Pro Val Cys Asn Asn Ser Ser Val Gln Val
1340                1345                1350

Gly Cys Leu Thr Arg Glu Arg Leu Gly Val Asn Val Thr Trp Lys
1355                1360                1365

Ser Arg Leu Glu Asp Ile Pro Val Ala Ser Leu Pro Asp Leu His
1370                1375                1380

Asp Ile Glu Arg Ala Leu Val Gly Lys Asp Leu Leu Gly Arg Phe
1385                1390                1395

Thr Asp Leu Ile Gln Ser Gly Ser Phe Gln Leu His Leu Asp Ser
1400                1405                1410

Lys Thr Phe Pro Ala Glu Thr Ile Arg Phe Leu Gln Gly Asp His
1415                1420                1425

Phe Gly Thr Ser Pro Arg Thr Arg Phe Gly Cys Ser Glu Gly Phe
1430                1435                1440

Tyr Gln Val Leu Thr Ser Glu Ala Ser Gln Asp Gly Leu Gly Cys
1445                1450                1455

Val Lys Cys His Glu Gly Ser Tyr Ser Gly Asp Glu Glu Cys Ile
1460                1465                1470

Pro Cys Pro Val Gly Phe Tyr Gln Glu Gln Ala Gly Ser Leu Ala
1475                1480                1485

Cys Val Pro Cys Pro Val Gly Arg Thr Thr Ile Ser Ala Gly Ala
1490                1495                1500

Phe Ser Gln Thr His Cys Val Thr Asp Cys Gln Arg Asn Glu Ala
1505                1510                1515
```

-continued

```
Gly Leu Gln Cys Asp Gln Asn Gly Gln Tyr Arg Ala Ser Gln Lys
    1520                1525                1530
Asp Arg Gly Ser Gly Lys Ala Phe Cys Val Asp Gly Glu Gly Arg
    1535                1540                1545
Arg Leu Pro Trp Trp Glu Thr Glu Ala Pro Leu Glu Asp Ser Gln
    1550                1555                1560
Cys Leu Met Met Gln Lys Phe Glu Lys Val Pro Glu Ser Lys Val
    1565                1570                1575
Ile Phe Asp Ala Asn Ala Pro Val Ala Val Arg Ser Lys Val Pro
    1580                1585                1590
Asp Ser Glu Phe Pro Val Met Gln Cys Leu Thr Asp Cys Thr Glu
    1595                1600                1605
Asp Glu Ala Cys Ser Phe Phe Thr Val Ser Thr Thr Glu Pro Glu
    1610                1615                1620
Ile Ser Cys Asp Phe Tyr Ala Trp Thr Ser Asp Asn Val Ala Cys
    1625                1630                1635
Met Thr Ser Asp Gln Lys Arg Asp Ala Leu Gly Asn Ser Lys Ala
    1640                1645                1650
Thr Ser Phe Gly Ser Leu Arg Cys Gln Val Lys Val Arg Ser His
    1655                1660                1665
Gly Gln Asp Ser Pro Ala Val Tyr Leu Lys Lys Gly Gln Gly Ser
    1670                1675                1680
Thr Thr Thr Leu Gln Lys Arg Phe Glu Pro Thr Gly Phe Gln Asn
    1685                1690                1695
Met Leu Ser Gly Leu Tyr Asn Pro Ile Val Phe Ser Ala Ser Gly
    1700                1705                1710
Ala Asn Leu Thr Asp Ala His Leu Phe Cys Leu Leu Ala Cys Asp
    1715                1720                1725
Arg Asp Leu Cys Cys Asp Gly Phe Val Leu Thr Gln Val Gln Gly
    1730                1735                1740
Gly Ala Ile Ile Cys Gly Leu Leu Ser Ser Pro Ser Val Leu Leu
    1745                1750                1755
Cys Asn Val Lys Asp Trp Met Asp Pro Ser Glu Ala Trp Ala Asn
    1760                1765                1770
Ala Thr Cys Pro Gly Val Thr Tyr Asp Gln Glu Ser His Gln Val
    1775                1780                1785
Ile Leu Arg Leu Gly Asp Gln Glu Phe Ile Lys Ser Leu Thr Pro
    1790                1795                1800
Leu Glu Gly Thr Gln Asp Thr Phe Thr Asn Phe Gln Gln Val Tyr
    1805                1810                1815
Leu Trp Lys Asp Ser Asp Met Gly Ser Arg Pro Glu Ser Met Gly
    1820                1825                1830
Cys Arg Lys Asn Thr Val Pro Arg Pro Ala Ser Pro Thr Glu Ala
    1835                1840                1845
Gly Leu Thr Thr Glu Leu Phe Ser Pro Val Asp Leu Asn Gln Val
    1850                1855                1860
Ile Val Asn Gly Asn Gln Ser Leu Ser Ser Gln Lys His Trp Leu
    1865                1870                1875
Phe Lys His Leu Phe Ser Ala Gln Gln Ala Asn Leu Trp Cys Leu
    1880                1885                1890
Ser Arg Cys Val Gln Glu His Ser Phe Cys Gln Leu Ala Glu Ile
    1895                1900                1905
Thr Glu Ser Ala Ser Leu Tyr Phe Thr Cys Thr Leu Tyr Pro Glu
```

-continued

```
          1910                1915                1920

Ala Gln Val Cys Asp Asp Ile Met Glu Ser Asn Thr Gln Gly Cys
    1925                1930                1935

Arg Leu Ile Leu Pro Gln Met Pro Lys Ala Leu Phe Arg Lys Lys
    1940                1945                1950

Val Ile Leu Glu Asp Lys Val Lys Asn Phe Tyr Thr Arg Leu Pro
    1955                1960                1965

Phe Gln Lys Leu Met Gly Ile Ser Ile Arg Asn Lys Val Pro Met
    1970                1975                1980

Ser Glu Lys Ser Ile Ser Asn Gly Phe Phe Glu Cys Glu Arg Arg
    1985                1990                1995

Cys Asp Ala Asp Pro Cys Cys Thr Gly Phe Gly Phe Leu Asn Val
    2000                2005                2010

Ser Gln Leu Lys Gly Gly Glu Val Thr Cys Leu Thr Leu Asn Ser
    2015                2020                2025

Leu Gly Ile Gln Met Cys Ser Glu Glu Asn Gly Gly Ala Trp Arg
    2030                2035                2040

Ile Leu Asp Cys Gly Ser Pro Asp Ile Glu Val His Thr Tyr Pro
    2045                2050                2055

Phe Gly Trp Tyr Gln Lys Pro Ile Ala Gln Asn Asn Ala Pro Ser
    2060                2065                2070

Phe Cys Pro Leu Val Val Leu Pro Ser Leu Thr Glu Lys Val Ser
    2075                2080                2085

Leu Glu Ser Trp Gln Ser Leu Ala Leu Ser Ser Val Val Val Asp
    2090                2095                2100

Pro Ser Ile Arg His Phe Asp Val Ala His Val Ser Thr Ala Ala
    2105                2110                2115

Thr Ser Asn Phe Ser Ala Val Arg Asp Leu Cys Leu Ser Glu Cys
    2120                2125                2130

Ser Gln His Glu Ala Cys Leu Ile Thr Thr Leu Gln Thr Gln Leu
    2135                2140                2145

Gly Ala Val Arg Cys Met Phe Tyr Ala Asp Thr Gln Ser Cys Thr
    2150                2155                2160

His Ser Leu Gln Gly Arg Asn Cys Arg Leu Leu Leu Arg Glu Glu
    2165                2170                2175

Ala Thr His Ile Tyr Arg Lys Pro Gly Ile Ser Leu Leu Ser Tyr
    2180                2185                2190

Glu Ala Ser Val Pro Ser Val Pro Ile Ser Thr His Gly Arg Leu
    2195                2200                2205

Leu Gly Arg Ser Gln Ala Ile Gln Val Gly Thr Ser Trp Lys Gln
    2210                2215                2220

Val Asp Gln Phe Leu Gly Val Pro Tyr Ala Ala Pro Pro Leu Ala
    2225                2230                2235

Glu Arg His Phe Gln Ala Pro Glu Pro Leu Asn Trp Thr Gly Ser
    2240                2245                2250

Trp Asp Ala Ser Lys Pro Arg Ala Ser Cys Trp Gln Pro Gly Thr
    2255                2260                2265

Arg Thr Ser Thr Ser Pro Gly Val Ser Glu Asp Cys Leu Tyr Leu
    2270                2275                2280

Asn Val Phe Ile Pro Gln Asn Val Ala Pro Asn Ala Ser Val Leu
    2285                2290                2295

Val Phe Phe His Asn Thr Met Asp Arg Glu Glu Ser Glu Gly Trp
    2300                2305                2310
```

```
Pro Ala Ile Asp Gly Ser Phe Leu Ala Ala Val Gly Asn Leu Ile
2315                2320                2325

Val Val Thr Ala Ser Tyr Arg Val Gly Val Phe Gly Phe Leu Ser
2330                2335                2340

Ser Gly Ser Gly Glu Val Ser Gly Asn Trp Gly Leu Leu Asp Gln
2345                2350                2355

Val Ala Ala Leu Thr Trp Val Gln Thr His Ile Arg Gly Phe Gly
2360                2365                2370

Gly Asp Pro Arg Arg Val Ser Leu Ala Ala Asp Arg Gly Gly Ala
2375                2380                2385

Asp Val Ala Ser Ile His Leu Leu Thr Ala Arg Ala Thr Asn Ser
2390                2395                2400

Gln Leu Phe Arg Arg Ala Val Leu Met Gly Gly Ser Ala Leu Ser
2405                2410                2415

Pro Ala Ala Val Ile Ser His Glu Arg Ala Gln Gln Gln Ala Ile
2420                2425                2430

Ala Leu Ala Lys Glu Val Ser Cys Pro Met Ser Ser Ser Gln Glu
2435                2440                2445

Val Val Ser Cys Leu Arg Gln Lys Pro Ala Asn Val Leu Asn Asp
2450                2455                2460

Ala Gln Thr Lys Leu Leu Ala Val Ser Gly Pro Phe His Tyr Trp
2465                2470                2475

Gly Pro Val Ile Asp Gly His Phe Leu Arg Glu Pro Pro Ala Arg
2480                2485                2490

Ala Leu Lys Arg Ser Leu Trp Val Glu Val Asp Leu Leu Ile Gly
2495                2500                2505

Ser Ser Gln Asp Asp Gly Leu Ile Asn Arg Ala Lys Ala Val Lys
2510                2515                2520

Gln Phe Glu Glu Ser Arg Gly Arg Thr Ser Ser Lys Thr Ala Phe
2525                2530                2535

Tyr Gln Ala Leu Gln Asn Ser Leu Gly Gly Glu Asp Ser Asp Ala
2540                2545                2550

Arg Val Glu Ala Ala Ala Thr Trp Tyr Tyr Ser Leu Glu His Ser
2555                2560                2565

Thr Asp Asp Tyr Ala Ser Phe Ser Arg Ala Leu Glu Asn Ala Thr
2570                2575                2580

Arg Asp Tyr Phe Ile Ile Cys Pro Ile Ile Asp Met Ala Ser Ala
2585                2590                2595

Trp Ala Lys Arg Ala Arg Gly Asn Val Phe Met Tyr His Ala Pro
2600                2605                2610

Glu Asn Tyr Gly His Gly Ser Leu Glu Leu Leu Ala Asp Val Gln
2615                2620                2625

Phe Ala Leu Gly Leu Pro Phe Tyr Pro Ala Tyr Glu Gly Gln Phe
2630                2635                2640

Ser Leu Glu Glu Lys Ser Leu Ser Leu Lys Ile Met Gln Tyr Phe
2645                2650                2655

Ser His Phe Ile Arg Ser Gly Asn Pro Asn Tyr Pro Tyr Glu Phe
2660                2665                2670

Ser Arg Lys Val Pro Thr Phe Ala Thr Pro Trp Pro Asp Phe Val
2675                2680                2685

Pro Arg Ala Gly Gly Glu Asn Tyr Lys Glu Phe Ser Glu Leu Leu
2690                2695                2700

Pro Asn Arg Gln Gly Leu Lys Lys Ala Asp Cys Ser Phe Trp Ser
2705                2710                2715
```

```
Lys Tyr Ile Ser Ser Leu Lys Thr Ser Ala Asp Gly Ala Lys Gly
        2720                2725                2730

Gly Gln Ser Ala Glu Ser Glu Glu Glu Glu Leu Thr Ala Gly Ser
        2735                2740                2745

Gly Leu Arg Glu Asp Leu Leu Ser Leu Gln Glu Pro Gly Ser Lys
        2750                2755                2760

Thr Tyr Ser Lys
        2765

<210> SEQ ID NO 39
<211> LENGTH: 822
<212> TYPE: DNA
<213> ORGANISM: human

<400> SEQUENCE: 39
atgggcatcc tcagcgtaga cttgctgatc acactgcaaa ttctgccagt ttttttctcc      60
aactgcctct tcctggctct ctatgactcg gtcattctgc tcaagcacgt ggtgctgctg     120
ttgagccgct ccaagtccac tcgcggagag tggcggcgca tgctgaccct cagagggactg   180 cgctgcgtct ggaagagctt cctcctcgat gcctacaaac aggtgaaatt gggtgaggat    240
gcccccaatt ccagtgtggt gcatgtctcc agtacagaag gaggtgacaa cagtggcaat    300
ggtacccagg agaagatagc tgagggagcc acatgccacc ttcttgactt tgccagccct   360
gagcgcccac tagtggtcaa ctttggctca gccacttgac ctcctttcac gagccagctg   420
ccagccttcc gcaaactggt ggaagagttc tcctcagtgg ctgacttcct gctggtctac   480
attgatgagg ctcatccatc agatggctgg gcgataccgg gggactcctc tttgtctttt   540
gaggtgaaga agcaccagaa ccaggaagat cgatgtgcag cagcccagca gcttctggag   600
cgtttctcct tgccgcccca gtgccgagtt gtggctgacc gcatggacaa taacgccaac   660
atagcttacg gggtagcctt tgaacgtgtg tgcattgtgc agagacagaa aattgcttat    720
ctgggaggaa agggccccct ctcctacaac cttcaagaag tccggcattg gctggagaag   780
aatttcagca agagatgaaa gaaaactaga ttagctggtt aa                       822

<210> SEQ ID NO 40
<211> LENGTH: 273
<212> TYPE: PRT
<213> ORGANISM: human
<220> FEATURE:
<221> NAME/KEY: MISC_FEATURE
<222> LOCATION: (133)..(133)
<223> OTHER INFORMATION: Xaa is Selenocysteine
<220> FEATURE:
<221> NAME/KEY: MISC_FEATURE
<222> LOCATION: (266)..(266)
<223> OTHER INFORMATION: Xaa is Selenocysteine

<400> SEQUENCE: 40

Met Gly Ile Leu Ser Val Asp Leu Leu Ile Thr Leu Gln Ile Leu Pro
1               5                   10                  15

Val Phe Phe Ser Asn Cys Leu Phe Leu Ala Leu Tyr Asp Ser Val Ile
            20                  25                  30

Leu Leu Lys His Val Val Leu Leu Ser Arg Ser Lys Ser Thr Arg
        35                  40                  45

Gly Glu Trp Arg Arg Met Leu Thr Ser Glu Gly Leu Arg Cys Val Trp
    50                  55                  60

Lys Ser Phe Leu Leu Asp Ala Tyr Lys Gln Val Lys Leu Gly Glu Asp
65                  70                  75                  80
```

-continued

```
Ala Pro Asn Ser Ser Val Val His Val Ser Thr Glu Gly Gly Asp
            85                  90                  95

Asn Ser Gly Asn Gly Thr Gln Glu Lys Ile Ala Glu Gly Ala Thr Cys
            100                 105                 110

His Leu Leu Asp Phe Ala Ser Pro Glu Arg Pro Leu Val Val Asn Phe
            115                 120                 125

Gly Ser Ala Thr Xaa Pro Pro Phe Thr Ser Gln Leu Pro Ala Phe Arg
            130                 135                 140

Lys Leu Val Glu Glu Phe Ser Val Ala Asp Phe Leu Leu Val Tyr
145                 150                 155                 160

Ile Asp Glu Ala His Pro Ser Asp Gly Trp Ala Ile Pro Gly Asp Ser
                    165                 170                 175

Ser Leu Ser Phe Glu Val Lys Lys His Gln Asn Gln Glu Asp Arg Cys
                    180                 185                 190

Ala Ala Ala Gln Gln Leu Leu Glu Arg Phe Ser Leu Pro Pro Gln Cys
                    195                 200                 205

Arg Val Val Ala Asp Arg Met Asp Asn Asn Ala Asn Ile Ala Tyr Gly
                    210                 215                 220

Val Ala Phe Glu Arg Val Cys Ile Val Gln Arg Gln Lys Ile Ala Tyr
225                 230                 235                 240

Leu Gly Gly Lys Gly Pro Phe Ser Tyr Asn Leu Gln Glu Val Arg His
                    245                 250                 255

Trp Leu Glu Lys Asn Phe Ser Lys Arg Xaa Lys Lys Thr Arg Leu Ala
                    260                 265                 270

Gly
```

<210> SEQ ID NO 41
<211> LENGTH: 19
<212> TYPE: DNA
<213> ORGANISM: Artificial Sequence
<220> FEATURE:
<223> OTHER INFORMATION: artificial

<400> SEQUENCE: 41
aacaagaaat accgtgccc                                                19

<210> SEQ ID NO 42
<211> LENGTH: 22
<212> TYPE: DNA
<213> ORGANISM: Artificial Sequence
<220> FEATURE:
<223> OTHER INFORMATION: artificial

<400> SEQUENCE: 42
gtacgaacca gctcgttatt ag                                            22

<210> SEQ ID NO 43
<211> LENGTH: 20
<212> TYPE: DNA
<213> ORGANISM: Artificial Sequence
<220> FEATURE:
<223> OTHER INFORMATION: artificial

<400> SEQUENCE: 43
cactagcagt taatgctgcc                                               20

<210> SEQ ID NO 44
<211> LENGTH: 21
<212> TYPE: DNA
<213> ORGANISM: Artificial Sequence
<220> FEATURE:

```
<223> OTHER INFORMATION: artificial

<400> SEQUENCE: 44
tgctcaaatc aagaccaatc c                                          21

<210> SEQ ID NO 45
<211> LENGTH: 21
<212> TYPE: DNA
<213> ORGANISM: Artificial Sequence
<220> FEATURE:
<223> OTHER INFORMATION: artificial

<400> SEQUENCE: 45
gcgacagagc caaaatcaga g                                          21

<210> SEQ ID NO 46
<211> LENGTH: 20
<212> TYPE: DNA
<213> ORGANISM: Artificial Sequence
<220> FEATURE:
<223> OTHER INFORMATION: artificial

<400> SEQUENCE: 46
agtcagccaa gccagagaag                                            20

<210> SEQ ID NO 47
<211> LENGTH: 22
<212> TYPE: DNA
<213> ORGANISM: Artificial Sequence
<220> FEATURE:
<223> OTHER INFORMATION: artificial

<400> SEQUENCE: 47
gaaggcatgt atattgctga gg                                         22

<210> SEQ ID NO 48
<211> LENGTH: 21
<212> TYPE: DNA
<213> ORGANISM: Artificial Sequence
<220> FEATURE:
<223> OTHER INFORMATION: artificial

<400> SEQUENCE: 48
tgaactggga gtaggaagtt g                                          21

<210> SEQ ID NO 49
<211> LENGTH: 22
<212> TYPE: DNA
<213> ORGANISM: Artificial Sequence
<220> FEATURE:
<223> OTHER INFORMATION: artificial

<400> SEQUENCE: 49
gcttgatgaa actctgaaag tg                                         22

<210> SEQ ID NO 50
<211> LENGTH: 19
<212> TYPE: DNA
<213> ORGANISM: Artificial Sequence
<220> FEATURE:
<223> OTHER INFORMATION: artificial

<400> SEQUENCE: 50
agaactcctg gcagaatgg                                             19

<210> SEQ ID NO 51
```

```
<211> LENGTH: 19
<212> TYPE: DNA
<213> ORGANISM: Artificial Sequence
<220> FEATURE:
<223> OTHER INFORMATION: artificial

<400> SEQUENCE: 51
catcccagcc ccaattttc                                                    19

<210> SEQ ID NO 52
<211> LENGTH: 19
<212> TYPE: DNA
<213> ORGANISM: Artificial Sequence
<220> FEATURE:
<223> OTHER INFORMATION: artificial

<400> SEQUENCE: 52
aatactcctg tcgcctctc                                                    19

<210> SEQ ID NO 53
<211> LENGTH: 22
<212> TYPE: DNA
<213> ORGANISM: Artificial Sequence
<220> FEATURE:
<223> OTHER INFORMATION: artificial

<400> SEQUENCE: 53
cggcttcaga caaaaactca ag                                                22

<210> SEQ ID NO 54
<211> LENGTH: 19
<212> TYPE: DNA
<213> ORGANISM: Artificial Sequence
<220> FEATURE:
<223> OTHER INFORMATION: artificial

<400> SEQUENCE: 54
agaagggaca gcagcaaac                                                    19

<210> SEQ ID NO 55
<211> LENGTH: 22
<212> TYPE: DNA
<213> ORGANISM: Artificial Sequence
<220> FEATURE:
<223> OTHER INFORMATION: artificial

<400> SEQUENCE: 55
tttgagaaag agccattggg ag                                                22

<210> SEQ ID NO 56
<211> LENGTH: 21
<212> TYPE: DNA
<213> ORGANISM: Artificial Sequence
<220> FEATURE:
<223> OTHER INFORMATION: artificial

<400> SEQUENCE: 56
tagcagcaca taggcatcca c                                                 21

<210> SEQ ID NO 57
<211> LENGTH: 19
<212> TYPE: DNA
<213> ORGANISM: Artificial Sequence
<220> FEATURE:
<223> OTHER INFORMATION: artificial

<400> SEQUENCE: 57
```
ttcccttcgc tcagttctc                               19

<210> SEQ ID NO 58
<211> LENGTH: 19
<212> TYPE: DNA
<213> ORGANISM: Artificial Sequence
<220> FEATURE:
<223> OTHER INFORMATION: artificial

<400> SEQUENCE: 58
atgcctacag ttttgtgcc                               19

<210> SEQ ID NO 59
<211> LENGTH: 20
<212> TYPE: DNA
<213> ORGANISM: Artificial Sequence
<220> FEATURE:
<223> OTHER INFORMATION: artificial

<400> SEQUENCE: 59
atttcagagc agttggtgtt                              20

<210> SEQ ID NO 60
<211> LENGTH: 20
<212> TYPE: DNA
<213> ORGANISM: Artificial Sequence
<220> FEATURE:
<223> OTHER INFORMATION: artificial

<400> SEQUENCE: 60
gttacccaat tcatggaaga                              20

<210> SEQ ID NO 61
<211> LENGTH: 19
<212> TYPE: DNA
<213> ORGANISM: Artificial Sequence
<220> FEATURE:
<223> OTHER INFORMATION: artificial

<400> SEQUENCE: 61
aggcctcact gggtattct                               19

<210> SEQ ID NO 62
<211> LENGTH: 21
<212> TYPE: DNA
<213> ORGANISM: Artificial Sequence
<220> FEATURE:
<223> OTHER INFORMATION: artificial

<400> SEQUENCE: 62
tatcctgacc agccaatgtt c                            21

<210> SEQ ID NO 63
<211> LENGTH: 20
<212> TYPE: DNA
<213> ORGANISM: Artificial Sequence
<220> FEATURE:
<223> OTHER INFORMATION: artificial

<400> SEQUENCE: 63
cgcctgtgat ggataattcc                              20

<210> SEQ ID NO 64
<211> LENGTH: 21
<212> TYPE: DNA
<213> ORGANISM: Artificial Sequence
<220> FEATURE:

<223> OTHER INFORMATION: artificial

<400> SEQUENCE: 64
agcatctgtt ccatatcctg a                                          21

<210> SEQ ID NO 65
<211> LENGTH: 21
<212> TYPE: DNA
<213> ORGANISM: Artificial Sequence
<220> FEATURE:
<223> OTHER INFORMATION: artificial

<400> SEQUENCE: 65
gaaaacaagt gccattgcaa a                                          21

<210> SEQ ID NO 66
<211> LENGTH: 19
<212> TYPE: DNA
<213> ORGANISM: Artificial Sequence
<220> FEATURE:
<223> OTHER INFORMATION: artificial

<400> SEQUENCE: 66
gctaagctgt cagatattt                                             19

<210> SEQ ID NO 67
<211> LENGTH: 19
<212> TYPE: DNA
<213> ORGANISM: Artificial Sequence
<220> FEATURE:
<223> OTHER INFORMATION: artificial

<400> SEQUENCE: 67
cagcaggcca gaaatgaag                                             19

<210> SEQ ID NO 68
<211> LENGTH: 19
<212> TYPE: DNA
<213> ORGANISM: Artificial Sequence
<220> FEATURE:
<223> OTHER INFORMATION: artificial

<400> SEQUENCE: 68
cgtcaagtat gaccgcaag                                             19

<210> SEQ ID NO 69
<211> LENGTH: 20
<212> TYPE: DNA
<213> ORGANISM: Artificial Sequence
<220> FEATURE:
<223> OTHER INFORMATION: artificial

<400> SEQUENCE: 69
ctgccatcct caaccagatt                                            20

<210> SEQ ID NO 70
<211> LENGTH: 20
<212> TYPE: DNA
<213> ORGANISM: Artificial Sequence
<220> FEATURE:
<223> OTHER INFORMATION: artificial

<400> SEQUENCE: 70
aacgcctgga tttccttttt                                            20

<210> SEQ ID NO 71

```
<211> LENGTH: 20
<212> TYPE: DNA
<213> ORGANISM: Artificial Sequence
<220> FEATURE:
<223> OTHER INFORMATION: artificial

<400> SEQUENCE: 71
tactaggccc aaacccagtg                                               20

<210> SEQ ID NO 72
<211> LENGTH: 20
<212> TYPE: DNA
<213> ORGANISM: Artificial Sequence
<220> FEATURE:
<223> OTHER INFORMATION: artificial

<400> SEQUENCE: 72
cctggctttc cagtgacatt                                               20

<210> SEQ ID NO 73
<211> LENGTH: 22
<212> TYPE: DNA
<213> ORGANISM: Artificial Sequence
<220> FEATURE:
<223> OTHER INFORMATION: artificial

<400> SEQUENCE: 73
taagggagac cctggtgaga ag                                            22

<210> SEQ ID NO 74
<211> LENGTH: 20
<212> TYPE: DNA
<213> ORGANISM: Artificial Sequence
<220> FEATURE:
<223> OTHER INFORMATION: artificial

<400> SEQUENCE: 74
accccagctc tggttcatag                                               20

<210> SEQ ID NO 75
<211> LENGTH: 20
<212> TYPE: DNA
<213> ORGANISM: Artificial Sequence
<220> FEATURE:
<223> OTHER INFORMATION: artificial

<400> SEQUENCE: 75
gtgccggagt ggttatgagt                                               20

<210> SEQ ID NO 76
<211> LENGTH: 20
<212> TYPE: DNA
<213> ORGANISM: Artificial Sequence
<220> FEATURE:
<223> OTHER INFORMATION: artificial

<400> SEQUENCE: 76
tagctgcagg gtgacatctg                                               20

<210> SEQ ID NO 77
<211> LENGTH: 20
<212> TYPE: DNA
<213> ORGANISM: Artificial Sequence
<220> FEATURE:
<223> OTHER INFORMATION: artificial

<400> SEQUENCE: 77
```

```
tcccgttcag aagacagctt                                               20

<210> SEQ ID NO 78
<211> LENGTH: 21
<212> TYPE: DNA
<213> ORGANISM: Artificial Sequence
<220> FEATURE:
<223> OTHER INFORMATION: artificial

<400> SEQUENCE: 78
cacgagggca aagacaagga c                                             21

<210> SEQ ID NO 79
<211> LENGTH: 10
<212> TYPE: DNA
<213> ORGANISM: Artificial Sequence
<220> FEATURE:
<223> OTHER INFORMATION: artificial

<400> SEQUENCE: 79
aacaattggg                                                          10

<210> SEQ ID NO 80
<211> LENGTH: 10
<212> TYPE: DNA
<213> ORGANISM: Artificial Sequence
<220> FEATURE:
<223> OTHER INFORMATION: artificial

<400> SEQUENCE: 80
tttcacaaca                                                          10

<210> SEQ ID NO 81
<211> LENGTH: 10
<212> TYPE: DNA
<213> ORGANISM: Artificial Sequence
<220> FEATURE:
<223> OTHER INFORMATION: artificial

<400> SEQUENCE: 81
tatttactct                                                          10

<210> SEQ ID NO 82
<211> LENGTH: 10
<212> TYPE: DNA
<213> ORGANISM: Artificial Sequence
<220> FEATURE:
<223> OTHER INFORMATION: artificial

<400> SEQUENCE: 82
ttgtaaatta                                                          10

<210> SEQ ID NO 83
<211> LENGTH: 10
<212> TYPE: DNA
<213> ORGANISM: Artificial Sequence
<220> FEATURE:
<223> OTHER INFORMATION: artificial

<400> SEQUENCE: 83
ctgtaaatat                                                          10

<210> SEQ ID NO 84
<211> LENGTH: 10
<212> TYPE: DNA
<213> ORGANISM: Artificial Sequence
<220> FEATURE:
```

<223> OTHER INFORMATION: artificial

<400> SEQUENCE: 84
gataggtcgg                                                                    10

<210> SEQ ID NO 85
<211> LENGTH: 10
<212> TYPE: DNA
<213> ORGANISM: Artificial Sequence
<220> FEATURE:
<223> OTHER INFORMATION: artificial

<400> SEQUENCE: 85
agctgagcta                                                                    10

<210> SEQ ID NO 86
<211> LENGTH: 10
<212> TYPE: DNA
<213> ORGANISM: Artificial Sequence
<220> FEATURE:
<223> OTHER INFORMATION: artificial

<400> SEQUENCE: 86
taatgtattc                                                                    10

<210> SEQ ID NO 87
<211> LENGTH: 10
<212> TYPE: DNA
<213> ORGANISM: Artificial Sequence
<220> FEATURE:
<223> OTHER INFORMATION: artificial

<400> SEQUENCE: 87
gctttacttt                                                                    10

<210> SEQ ID NO 88
<211> LENGTH: 10
<212> TYPE: DNA
<213> ORGANISM: Artificial Sequence
<220> FEATURE:
<223> OTHER INFORMATION: artificial

<400> SEQUENCE: 88
taaatacttg                                                                    10

<210> SEQ ID NO 89
<211> LENGTH: 10
<212> TYPE: DNA
<213> ORGANISM: Artificial Sequence
<220> FEATURE:
<223> OTHER INFORMATION: artificial

<400> SEQUENCE: 89
gcgcatcaaa                                                                    10

<210> SEQ ID NO 90
<211> LENGTH: 10
<212> TYPE: DNA
<213> ORGANISM: Artificial Sequence
<220> FEATURE:
<223> OTHER INFORMATION: artificial

<400> SEQUENCE: 90
agcagggctc                                                                    10

<210> SEQ ID NO 91

```
<211> LENGTH: 10
<212> TYPE: DNA
<213> ORGANISM: Artificial Sequence
<220> FEATURE:
<223> OTHER INFORMATION: artificial

<400> SEQUENCE: 91
cagataagtt                                                              10

<210> SEQ ID NO 92
<211> LENGTH: 10
<212> TYPE: DNA
<213> ORGANISM: Artificial Sequence
<220> FEATURE:
<223> OTHER INFORMATION: artificial

<400> SEQUENCE: 92
cttcaatctt                                                              10

<210> SEQ ID NO 93
<211> LENGTH: 10
<212> TYPE: DNA
<213> ORGANISM: Artificial Sequence
<220> FEATURE:
<223> OTHER INFORMATION: artificial

<400> SEQUENCE: 93
gagaggaagg                                                              10

<210> SEQ ID NO 94
<211> LENGTH: 10
<212> TYPE: DNA
<213> ORGANISM: Artificial Sequence
<220> FEATURE:
<223> OTHER INFORMATION: artificial

<400> SEQUENCE: 94
tgatcaatat                                                              10

<210> SEQ ID NO 95
<211> LENGTH: 10
<212> TYPE: DNA
<213> ORGANISM: Artificial Sequence
<220> FEATURE:
<223> OTHER INFORMATION: artificial

<400> SEQUENCE: 95
ggtatgctgt                                                              10

<210> SEQ ID NO 96
<211> LENGTH: 10
<212> TYPE: DNA
<213> ORGANISM: Artificial Sequence
<220> FEATURE:
<223> OTHER INFORMATION: artificial

<400> SEQUENCE: 96
gatgaataaa                                                              10

<210> SEQ ID NO 97
<211> LENGTH: 10
<212> TYPE: DNA
<213> ORGANISM: Artificial Sequence
<220> FEATURE:
<223> OTHER INFORMATION: artificial

<400> SEQUENCE: 97
```

```
cggtgaagca                                                              10

<210> SEQ ID NO 98
<211> LENGTH: 10
<212> TYPE: DNA
<213> ORGANISM: Artificial Sequence
<220> FEATURE:
<223> OTHER INFORMATION: artificial

<400> SEQUENCE: 98
atgctaagag                                                              10
```